(12) United States Patent
Balasubramanian et al.

(10) Patent No.: US 7,985,759 B2
(45) Date of Patent: Jul. 26, 2011

(54) DIPEPTIDYL PEPTIDASE IV INHIBITORS AND PROCESSES FOR THEIR PREPARATION AND PHARMACEUTICAL COMPOSITIONS CONTAINING THEM

(75) Inventors: Gopalan Balasubramanian, Secundarabad (IN); Ravi Dhamjewar, Hyderabad (IN); Rasheed Mohammed, Hyderabad (IN); Sreedhara Swamy Keshavapura Hosamane, Mumbai (IN); Ishtiyaque Ahmad, Hyderabad (IN)

(73) Assignee: Matrix Laboratories Ltd., Seconderabad (IN)

( * ) Notice: Subject to any disclaimer, the term of this patent is extended or adjusted under 35 U.S.C. 154(b) by 323 days.

(21) Appl. No.: 12/295,930

(22) PCT Filed: Mar. 30, 2007

(86) PCT No.: PCT/IB2007/000830
§ 371 (c)(1),
(2), (4) Date: Oct. 3, 2008

(87) PCT Pub. No.: WO2007/113634
PCT Pub. Date: Oct. 11, 2007

(65) Prior Publication Data
US 2010/0160302 A1    Jun. 24, 2010

Related U.S. Application Data

(60) Provisional application No. 60/801,437, filed on May 18, 2006.

(30) Foreign Application Priority Data

Apr. 3, 2006   (IN) .............................. 610/CHE/2006

(51) Int. Cl.
*C07D 207/16*    (2006.01)
*C07D 209/48*    (2006.01)
*C07D 233/36*    (2006.01)
*A61K 31/4196*   (2006.01)

(52) U.S. Cl. ......... 514/325; 514/423; 548/528; 546/203
(58) Field of Classification Search .................. 548/528; 546/203; 514/325, 423
See application file for complete search history.

(56) References Cited

OTHER PUBLICATIONS

Wright et al., "cis-2,5-Dicyanopyrrolidine Inhibitors of Dipeptidyl Peptidase IV: Synthesis and in Vitro . . . " Journal of Medical Chemistry, 2006, vol. 49, No. 11, pp. 3068-3076.

*Primary Examiner* — Kahsay T Habte
(74) *Attorney, Agent, or Firm* — Ladas & Parry LLP

(57) ABSTRACT

The present invention relates to novel compounds representated by formula (I), where R, R1, R2, R3, X, Y, m, n are as defined. The present invention relates to compounds of the general formula I their derivatives, their analogs, their tautomeric forms, their stereoisomers, their diastereomers, their bioisosteres, their polymorphs, their pharmaceutically acceptable salts and pharmaceutically acceptable compositions containing them which are predominantly dipeptidyl peptidase IV inhibitors. The present invention also relates to the processes for the preparation of novel compounds of formula (I) and their use in treating type II diabetes and diabetic complications thereof and also for treating dislipidemia, hypercholesterolemia, obesity and hyperglycemia.

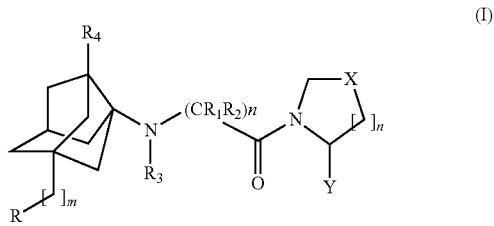

(I)

15 Claims, No Drawings

DIPEPTIDYL PEPTIDASE IV INHIBITORS AND PROCESSES FOR THEIR PREPARATION AND PHARMACEUTICAL COMPOSITIONS CONTAINING THEM

This application claims the benefit of Indian Application No. 610/CHE/2006 filed Apr. 3, 2006 and U.S. Provisional Application No. USA 60/801,437, filed May 18, 2006, both of which are hereby incorporated by reference.

FIELD OF INVENTION

The present invention relates to novel compounds represented by formula I, their derivatives, their analogs, their tautomeric forms, their stereoisomers, their bioisosters, their diastereomers, their polymorphs, their pharmaceutically acceptable salts, solvates and pharmaceutically acceptable compositions containing them, which are useful in treating type II diabetes and diabetic complications as well as for the treatment of dislipidemia, hypercholesterolemia, obesity, and hyperglycemia.

More specifically, the present invention relates to the compounds of formula I, which are predominantly serine protease inhibitors, particularly dipeptidyl peptidase inhibitors, more particularly dipeptidyl peptidase IV inhibitors, as well as to their derivatives, their analogs, their tautomeric forms, their stereoisomers, their bioisosters, their diastereomers, their polymorphs, their pharmaceutically acceptable salts, and solvates. Additionally, the present invention relates to pharmaceutically acceptable compositions containing the aforementioned compounds.

The compounds of the present invention are represented by formula I

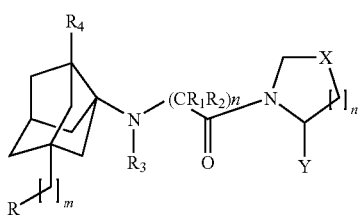

I its derivatives, analogs, tautomeric forms, stereoisomers, bioisosters, diastereomers, polymorphs, pharmaceutically acceptable salts and pharmaceutically acceptable solvates, wherein:

X=$CH_2$, CHF, $CF_2$, CHCl, CHOH, $CHOCH_3$, NH, $NCOCH_3$, CHPh, O, or S,

Y=CN, $R_1$ and $R_5$ are selected from hydrogen, $C_1$-$C_4$ alkyl, and hydroxy, $R_2$ is selected from hydrogen, $C_1$-$C_4$ alkyl, substituted alkyl, $C_{1-4}$ alkoxy $C_{1-4}$ alkyl, $C_{1-4}$ hydroxyalkyl, $R_5NHC_{1-4}$ alkyl, and $R_5NHC(NH)NHC_{1-4}$ alkyl, $R_3$ is selected from hydrogen and $C_1$-$C_4$ alkyl, $R_4$ is selected from hydrogen, $C_1$-$C_4$ alkyl, substituted alkyl, $C_1$-$C_4$ alkoxy, $C_1$-$C_4$ alkanoyloxy, hydroxy, amino, nitro, $C_2$-$C_6$ alkenyl, acyl, and halogen, n=1 or 2, m=0, 1, or 2, R=$R_{11}$, $R_{12}$, or $R_{13}$, in which $R_{11}$ comprises at least one of the groups selected from below a), b), or c), whereupon the optionally substituted cycloalkyl, heterocyclyl, and heteroaryl groups are linked to the nor-adamantyl moiety either directly or via a methylene or ethylene adjacent, either by C—C linkage or by C—N linkage.

a) A cycloalkyl group, which is optionally substituted by $C_1$-$C_4$ alkyl, dialkyl, or oxo, preferably a $C_4$-$C_7$ ring system, more preferably a $C_5$-$C_6$ ring system, which may be further functionalized or substituted with multiple degrees of substitution. Examples of possible cycloalkyl groups are cyclopentane, cyclohexane, cyclopentane dione, cyclohexane dione and the possible substitutions include $C_1$-$C_4$ alkyl, dialkyl, and oxo.

b) An optionally substituted heteroaryl group, preferably a 5 to 10 membered ring system, in which the heteroaryl ring is a monocyclic aromatic ring system or a bicyclic aromatic ring system comprising one, two, or more heteroatoms selected from nitrogen, sulfur, and oxygen. Possible heteroaryl groups include but not limited to tetrazole, triazole, pyrazole, imidazole, oxadiazole, pyridine, pyrimidine, indole, furan, benzofuran, benzimidazole, indazole, thiophene, and benzothiophene and the substitutions on the heteroaryl ring may be the same or different and are selected from $R_6$ and $R_7$, wherein $R_6$ is hydrogen, $C_1$-$C_4$ alkyl, $C_2$-$C_4$ alkenyl, hydroxy, hydroxy alkyl, alkylamino, haloalkyl, amino, acyl, $COOR_9$, or $COR_9$, and $R_7$ is selected from a group consisting of hydrogen, hydroxy, halogen, amino, nitro, $C_1$-$C_8$ alkyl, $C_2$-$C_4$ alkenyl, $COOR_9$, $CONR_8R_9$, $COR_9$, $NHCOOR_8$, $NHS(O)_2R_8$, $NHS(O)R_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $OSO_2R_8$, $OCONR_8R_9$, $SO_2R_8$, $SOR_8$, $SR_8$, $SO_2NR_8R_9$, and $S(O)_2OR_8$. When $R_6$ and $R_7$ are present on adjacent carbon atoms of the ring system, they may together form a six membered aromatic ring such as phenyl or a heterocyclic ring such as pyridine with further substitutions such as amino, hydroxy, alkyl, alkyl sulfonyl, alkyl thio, alkyl sulfinyl, carboxy, or oxo.

c) A heterocyclyl group optionally substituted by $C_1$-$C_3$ alkyl, dialkyl and oxo groups, wherein the heterocyclic ring system is a 4- to 10-membered mono- or bicyclic ring system with one or more heteroatoms selected from the group consisting of nitrogen, sulfur, and oxygen, wherein the heteroatoms can also be present as functional groups, such as N-oxides, sulfur oxides, and sulfur dioxides, wherein the heterocyclic ring system may contain one or two double bonds, and wherein the monocyclic heterocyclic ring may be optionally fused to a heteroaryl, aryl, or a cycloalkyl ring optionally substituted with $C_1$-$C_5$ alkyl, halogens, hydroxy, amino, nitro, haloalkyl, alkylamino, carboxy, NH(CO)$R_8$, $NHS(O)_2R_8$, $NHC(O)NHR_9$, $NHSOR_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, or $NHC(O)NHS(O)_2R_8$. Examples of such heterocyclic ring radicals include but are not limited to imidazolidinone, isothiazolidine-1,1-dioxide, pyrrolidine, pyrrolidinedione, oxopyrrolidine, isoxazolidinedione, isoindoledione, morpholine, thiomorpholine, thiomorpholine-1,1-dioxide, thiophene-1,1-dioxide, thiazolidinedione, piperidine, piperazine, tetrahydro pyrimidinone, [1,2]-thiazinane-1,1-dioxide, tetrahydro thiophene-1,1-dioxide, piperidinone, and tetrahydrothiopyran-1,1-dioxide.

$R_{12}$ is selected from hydrogen, halogen, haloalkyl, hydroxy, carboxy, nitro, amino, cyano, alkyl sulfinyl, alkylsulfonyl, alkylthio, amidinyl, alkoxy, alkoxy carbonylamino, ureido, thiureido, alkanoyl, alkanoyloxy, alkanoyl amino, carbamoyl, guanidyl, optionally substituted $C_1$-$C_8$ alkyl, and $C_2$-$C_6$ alkenyl.

$R_{13}$ is optionally substituted aryl, wherein the substituents may be the same or different and comprises at least one of the groups selected from a) hydrogen;

b) $C_1$-$C_8$ alkyl, $C_2$-$C_6$ alkenyl, halo, alkylhalo, alkoxy, alkylsulfonyl, alkylsulfinyl, alkoxy, alkanoyl, alkanoyloxy, acylamino, carbonylamino, guanidyl, nitro, amino, $COOR_9$, $R_8NHC(O)R_9$, $COR_9$, $CONR_8R_9$, $NHC(O)OR_8$, $NHC(O)R_8$, $NHC(O)NR_8R_9$, $NHC(O)NR_8R_9$, $NHS(O)_2R_8$, $NHS(O)R_8$, $NHS(O)_2NHR_8$, $NHS(O)_2NHC(O)R_8$, $NR_9COOR_9$, $NR_8COR_9$, $NR_9S(O)_2R_9$, $NR_8CONR_8R_9$, $NR_8C(S)NR_8R_9$, $NHC(O)NHS(O)_2R_8$, $S(O)_2R_8$, $SOR_8$, $SR_8$, $S(O)_2NR_8R_9$, $OCF_3$, $OS(O)_2R_8$, or $OC(O)NR_8R_9$.

c) Saturated, partially saturated, or unsaturated, mono- or bicyclic heterocyclic ring system optionally substituted by one or more groups selected from $C_1$-$C_3$ alkyl, $C_2$-$C_6$ alkenyl, dialkyl, and oxo, wherein the heterocyclic ring system is a 4- to 10-membered ring with one or more heteroatoms selected from the group consisting of nitrogen, sulfur, and oxygen, wherein the heteroatoms can also be present as functional groups, such as N-oxides, sulfur oxides, and sulfur dioxides. Examples of such heterocyclic ring radicals include, but are not limited to pyridine, pyrimidine, imidazolidinone, imidazolidinethione, indazole, indole, isoindole, quinazoline, quinoline, isoquinoline, cinnalone, isothiazolidine-1,1-dioxide, pyrrolidinone, 2-piperidinone, tetrahydropyrimidinone, azitidinone, and thiazane-1,1-dioxide.

The $R_8$, $R_9$, and $R_{10}$-groups, which are optionally substituted by halogen, hydroxy, alkoxy, cyano, nitro, alkyl, acyl, acyloxy, hydroxyalkyl, amino, alkylthio, or thioalkyl groups, may be the same or different and are individually selected from hydrogen, optionally substituted $C_1$-$C_8$ alkyl, aryl, arylalkyl, alkoxy carbonyl, and arylalkoxy carbonyl. When $R_8$ and $R_9$ are present together on a nitrogen atom they may form a 5- or 6-membered saturated, partially unsaturated, or unsaturated cyclic system containing carbon atoms, at least one nitrogen atom and optionally one or more other heteroatoms selected from oxygen, sulfur, and nitrogen.

The present invention also relates to a process for the preparation of compounds of formula I, their derivatives, their analogs, their tautomeric forms, their stereoisomers, their bioisosters, their diastereomers, their polymorphs, their pharmaceutically acceptable salts, and their solvates.

The present invention also relates to novel intermediates, processes for their preparation, their use in the preparation of compounds of formula I, and their derivatives, their analogs, their tautomeric forms, their stereoisomers, their bioisosters, their diastereomers, their polymorphs, their pharmaceutically acceptable salts, and their solvates.

BACKGROUND OF THE INVENTION

Diabetes is characterized by elevated levels of plasma glucose or hyperglycemia in the fasting state or after administration of glucose during an oral glucose tolerance test. There are two types of diabetes. Type 1 diabetes is usually diagnosed in children and young adults, and was previously known as juvenile diabetes. In type 1 diabetes, the body does not produce insulin. Type 2 diabetes is the most common form of diabetes. In type 2 diabetes, either the body does not produce enough insulin or the cells ignore the insulin. Patients with type 2 diabetes are at increased risk of macro vascular and micro vascular complications, including coronary artery disease, stroke, hypertension, nephropathy, peripheral vascular disease, neuropathy, and retinopathy.

A significant, rapidly growing fraction of the human population is affected by type 2 diabetes, a disease characterized by elevated blood glucose levels and relative insufficiency of insulin. Recently researches found that the activity of two potent stimulators of insulin secretion, GLP-1 and GIP, is rapidly abolished by the serine peptidase dipeptidyl peptidase IV (DPP-IV). DPP-IV is a member of a family of serine peptidases. CD26 or DPP-IV is a membrane-associated peptidase of 766 amino acids that is widely distributed in numerous tissues. DPP-4 also exists as a soluble circulating form in plasma and significant DPP-4-like activity is detectable in plasma from humans and rodents. The principal biological activity of CD26 (DPP-IV) is its enzymatic function. DPP-IV prefers substrates with an amino-terminal proline or alanine at position 2, but may also cleave substrates with non-preferred amino acids at position 2. The structure of GIP, GLP-1 and GLP-2 reveals a highly conserved alanine at position 2, rendering these peptides ideal putative substrates for the aminopeptidase dipeptidyl peptidase 4 (DPP-4). *Eur J Biochem.* 1993, 214(3), 829-35.

A glance at the available treatments for type 2 diabetes, which have not changed substantially in many years, makes clear that they all have their own limitations. There are many pharmacologic strategies to accomplish these goals. First of this series are alpha glucosidase inhibitors such as acarbose and miglitol, which function by interfering with the action of the alpha-glucosidases present in the small intestinal brush border. The consequence of this inhibition is a reduction in digestion and the consequent absorption of glucose into the systemic circulation. The reduction in glucose uptake allows the pancreatic beta-cells to regulate the insulin secretion more effectively. The advantage of the use of the alpha-glucosidase inhibitors is that they function locally in the intestine and have no major systemic action. Hypoglycemia does not usually occur with the use of alpha-glucosidase inhibitors but they are effective in reducing fasting plasma glucose (FPG) levels and levels of glycosylated hemoglobin ($HbA_{1c}$). The common adverse side effects of these inhibitors are abdominal bloating and discomfort, diarrhea, and flatulence.

The sulfonylureas and meglitinide classes of oral hypoglycemic drugs are referred to as endogenous insulin secretagogues because they induce the pancreatic release of endogenous insulin. Because these drugs can induce pronounced hypoglycemia, treatment is initiated with the lowest possible dose and carefully monitored until the dose results in a FPG of 110-140 mg/dL. Sulfonylureas function by binding to and inhibiting the pancreatic ATP-dependent potassium channel that is normally involved in glucose-mediated insulin secretion. Sulfonylureas have no significant effects on circulating triglycerides, lipoproteins, or cholesterol. The non-sulfonylurea insulin secretagogues are both fast acting and of short duration. However, meglitinides (non-sulfonylurea insulin secretagogues) do exert effects on potassium conductance. Like the sulfonylureas, the meglitinides have no direct effects on the circulating levels of plasma lipids.

The biguanides lower serum glucose levels by enhancing insulin-mediated suppression of hepatic glucose production and enhancing insulin-stimulated glucose uptake by skeletal muscle. Metformin is a member of this class and is currently the most widely prescribed insulin-sensitizing drug in clinical use. Metformin administration does not lead to increased insulin release from the pancreas and as such the risk of hypoglycemia is minimal. Because the major site of action for metformin is the liver its use can be contraindicated in patients with liver dysfunction. In adolescent females with type 2 diabetes, the use of metformin is highly recommended to reduce the incidence as well as the potential for polycystic ovarian syndrome. However the two biguanides, phenformin and metformin can induce lactic acidosis and nausea/diarrhea.

The peroxisome proliferator-activated nuclear receptor (PPAR) family has received particular scrutiny in the field of diabetes and as a result the thiazolidinediones have emerged as a therapeutic class. First generation thiazolidinediones were agonists of the PPAR gamma receptor and were able to reduce insulin resistance. One adverse effect associated with PPAR gamma receptor agonists is however weight gain. More recently molecules have been developed that activate PPAR alpha. This class is able to reduce triglyceride levels and is also able to improve insulin sensitivity and as a result dual PPAR alpha/PPAR gamma agonists have been developed with proposed beneficial effects over existing PPAR gamma- and alpha-preferential drugs in treatment of type 2 diabetes. But safety issues slowed down the entry of these drugs One of the exciting classes of agents in development are GLP-1 agonists. The primary metabolic responses to GLP-1 release from the enteroendocrine L-cells of the gut are inhibition of glucagon secretion and enhancement of glucose-dependent insulin release from the pancreas, both effects lead to decreased glycemic excursion. But the hormonal action of GLP-1 is rapidly terminated as a consequence of enzymatic cleavage by DPP IV. Recent clinical evidence has shown that either infusion of GLP-1 or inhibition of DPP IV can result in dramatic reductions in plasma glucose concentrations, reductions in $HbA_{1c}$, and improvement in pancreatic beta-cell function. Thus, both represent potential targets for the prevention of the hyperglycemia associated with diabetes and impaired insulin function. There are advantages and disadvantages with the current therapeutic approaches targeting GLP-1 action in diabetic patients. Current use of GLP-1 mimetics and/or GLP-1 receptor (GLP-1R) agonists focus on peptides or modified peptides and these must be given by injection, which leads to problems with the patient-compliance.

Another novel mechanism for the treatment of type 2 diabetes are Dipeptidyl peptidase-IV inhibitors. Dipeptidyl peptidase IV is a multifunctional protein involved in cleaving incretin hormones, hence serving to regulate glucose homeostasis and consequently viewed as a target for the management of Type 2 diabetes. The usefulness of Dipeptidyl peptidase IV in the treatment of Type 2 diabetes is based on the fact that Dipeptidyl peptidase IV in vivo readily inactivates GLP-1 and GIP. These are the incretins that are produced when food is consumed. These incretins stimulate production of insulin. Inhibition of Dipeptidyl peptidase IV leads to decreased inactivation of incretins, in turn increased efficacy of incretins in stimulating insulin production by pancreas. Therefore Dipeptidyl peptidase IV inhibition results in an increased level of serum insulin. An interesting observation is that incretins are produced only when food is consumed. So the Dipeptidyl peptidase IV inhibition is not expected to increase the level of insulin between meals which can lead to hypoglycemia. Inhibition of Dipeptidyl peptidase IV is therefore expected to increase insulin without increasing the risk of hypoglycemia. Investigational Dipeptidyl peptidase IV inhibitors offer an advantage over other novel therapies since they can be administered orally. Compliance in patients is much higher with orally delivered drugs than with those that require injection. Thus Dipeptidyl peptidase IV inhibitors are a promising new approach to treat type 2 diabetes, which function, at least in part, as indirect stimulators of insulin secretion. Mechanism and use of DPPIV inhibitors in various diseases is well explained in prior art patents like WO 2005/033106 and is herein incorporated by reference in its entirety.

PRIOR ART

International patent application WO 00/34241 discloses the compounds of the generic formula

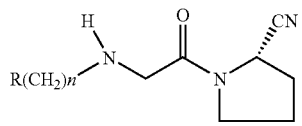

wherein R is substituted adamantyl.

International patent application WO 03/04498 discloses the compounds of the generic formula

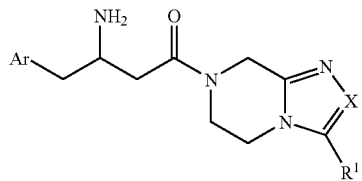

US-application US 2005/038020 discloses the compounds of generic formula

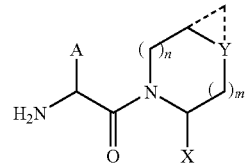

wherein A is an optionally substituted adamantyl group.

International patent application WO 2006/090244 discloses the compounds of formula

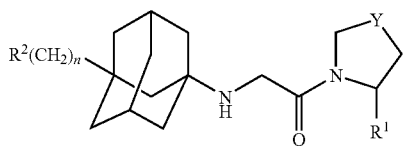

wherein n is 0, 1, 2, or 3.

R2 is substituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, $-NR_3R_4$, $-NH-S(O)m-R_3$, $-NH-CR_3R_4$, $C(O)-R_5$, $-C(O)O-R_3$, $-C(O)NR_3R_4$, $-S(O)m-$, $NR_3R_4$, nitro, cyano, formyl, acetyl, halogen, $-SR^a$, or a protecting group.

International patent application WO 2005/021536 discloses the compounds of formula

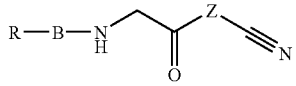

wherein one of the possible B substituents is adamantyl amine.

One of the representative examples is

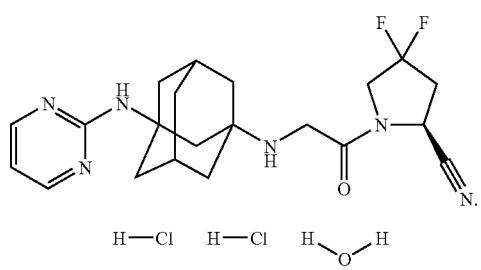

International patent application WO 2006/012395 discloses the compounds of formula

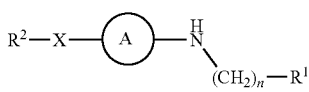

as peptidase inhibitors. One of the representative examples is

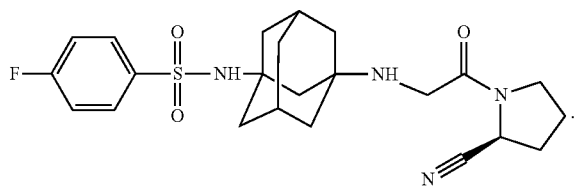

International patent application WO2005095339 discloses the compounds of formula

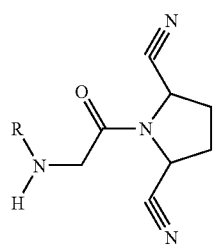

as DPPIV inhibitors.

US20050215784 discloses the compounds of formula

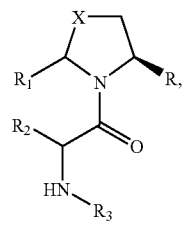

as DPPIV inhibitors.

Although there are a few DPPIV inhibitors in different stages of clinical trials such as the examples given above (LAF-237, MK-0431, BMS-477118, GSK23A), there is still a need for novel compounds in this area and the objective of the present invention is to provide novel nor-adamantyl cyano pyrrolidine compounds represented by formula I which have a DPPIV inhibitory activity as well as processes for their preparation.

SUMMARY OF THE INVENTION

The objective of the present invention is to provide novel compounds of formula I, having serine protease inhibiting activity, particularly dipeptidyl peptidase IV inhibiting activity for lowering blood glucose levels, lipid levels, cholesterol levels and reducing body weight, against type II diabetes and diabetic complications. The main objective of the present invention is therefore, to provide novel nor-adamantyl cyano pyrrolidine compounds represented by formula I, their derivatives, their analogs, their tautomeric forms, their stereoisomers, their bioisosteres, their diastereomers, their polymorphs, their pharmaceutically acceptable salts, solvates and pharmaceutically acceptable compositions containing them.

Another aspect of the present invention is to provide a process for the preparation of noradamantyl cyano pyrrolidine compounds represented by formula I, their derivatives, their analogs, their tautomeric forms, their stereoisomers, their bioisosters, their diastereomers, their polymorphs, their pharmaceutically acceptable salts, and their pharmaceutically acceptable solvates.

Another aspect of the present invention is to provide novel intermediates, processes for their preparation and use of these intermediates in processes for the preparation of said noradamantyl cyano pyrrolidine compounds represented by formula I and their derivatives, their analogs, their tautomeric forms, their stereoisomers, their polymorphs, their bioisosters, their diastereomers, their pharmaceutically acceptable salts, and solvates.

Another aspect of the present invention is to provide pharmaceutical compositions containing the compounds of the present invention represented by formula I, their derivatives, their analogs, their tautomeric forms, their stereoisomers, their bioisosters, their diastereomers, their polymorphs, their salts, solvates, or their mixtures in combination with suitable carriers, solvents, diluents and other media normally employed in preparing such compositions.

DETAILED DESCRIPTION OF THE INVENTION

The present invention is to provide compounds represented by formula I

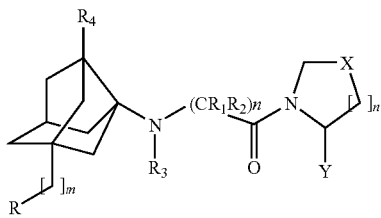

I their derivatives, their analogs, their tautomeric forms, their stereoisomers, their bioisosters, their diastereomers, their polymorphs, their pharmaceutically acceptable salts and their pharmaceutically acceptable solvates wherein X=$CH_2$, CHF, $CF_2$, CHCl, CHOH, $CHOCH_3$, NH, $NCOCH_3$, CHPh, O, or S,

Y=CN, $R_1$ and $R_5$ are selected from hydrogen, $C_1$-$C_4$ alkyl, and hydroxy, $R_2$ is selected from hydrogen, $C_1$-$C_4$ alkyl, substituted alkyl, $C_{1-4}$ alkoxy $C_{1-4}$ alkyl, $C_{1-4}$ hydroxyalkyl, $R_5NHC_{1-4}$ alkyl, and $R_5NHC(NH)NHC_{1-4}$ alkyl, $R_3$ is selected from hydrogen and $C_1$-$C_4$ alkyl, $R_4$ is selected from hydrogen, $C_1$-$C_4$ alkyl, substituted alkyl, $C_1$-$C_4$ alkoxy, $C_1$-$C_4$ alkanoyloxy, hydroxy, amino, nitro, $C_2$-$C_6$ alkenyl, acyl, and halogen, n=1 or 2, m=0, 1, or 2, R=$R_{11}$, $R_{12}$, or $R_{13}$, in which $R_{11}$ comprises at least one of the groups selected from a), b), or c), whereupon the optionally substituted cycloalkyl, heterocyclyl, and heteroaryl groups are linked to the noradamantyl moiety either directly or via a methylene or ethylene adjacent, either by C—C linkage or by C—N linkage a) A cycloalkyl group, which is optionally substituted by $C_1$-$C_4$ alkyl, dialkyl, or oxo, preferably a $C_4$-$C_7$ ring system, more preferably a $C_5$-$C_6$ ring system, which may be further functionalized or substituted with multiple degrees of substitution. Examples of possible cycloalkyl groups are cyclopentane, cyclohexane, cyclopentane dione, cyclohexane dione and the possible substitutions include $C_1$-$C_4$ alkyl, dialkyl, and oxo.

b) An optionally substituted heteroaryl group, preferably a 5 to 10 membered ring system, in which the heteroaryl ring is a monocyclic aromatic ring system or a bicyclic aromatic ring system comprising one, two, or more heteroatoms selected from nitrogen, sulfur, and oxygen. Possible heteroaryl groups include but are not limited to tetrazole, triazole, pyrazole, imidazole, oxadiazole, pyridine, pyrimidine, indole, furan, benzofuran, benzimidazole, indazole, thiophene, and benzothiophene and the substitutions on the heteroaryl ring may be the same or different and are selected from $R_6$ and $R_7$, wherein $R_6$ is hydrogen, $C_1$-$C_4$ alkyl, $C_2$-$C_4$ alkenyl, hydroxy, hydroxy alkyl, alkylamino, haloalkyl, amino, acyl, $COOR_9$, or $COR_9$, and $R_7$ is selected from a group consisting of hydrogen, hydroxy, halogen, amino, nitro, $C_1$-$C_8$ alkyl, $C_2$-$C_4$ alkenyl, $COOR_9$, $CONR_8R_9$, $COR_9$, $NHCOOR_8$, $NHS(O)_2R_8$, $NHS(O)R_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $OSO_2R_8$, $OCONR_8R_9$, $SO_2R_8$, $SOR_8$, $SR_8$, $SO_2NR_8R_9$, and $S(O)_2OR_8$. When $R_6$ and $R_7$ are present on adjacent carbon atoms of the ring system, they may together form a six membered aromatic ring such as phenyl or a heterocyclic ring such as pyridine with further substitutions such as amino, hydroxy, alkyl, alkyl sulfonyl, alkyl thio, alkyl sulfinyl, carboxy, or oxo.

Further preferred heteroaryl groups comprise

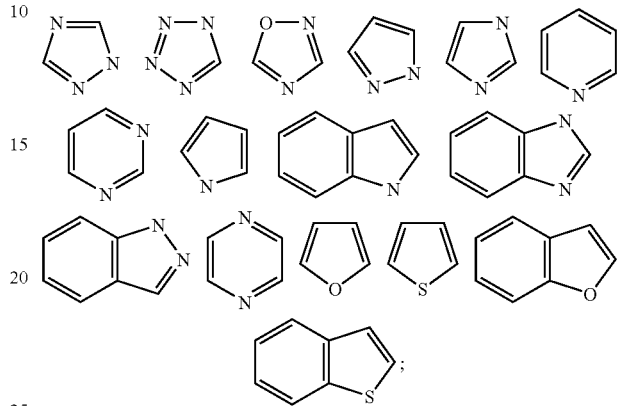

these examples do not limit the present invention.

c) A heterocyclyl group optionally substituted by $C_1$-$C_3$ alkyl, dialkyl and oxo groups, wherein the heterocyclic ring system is a 4- to 10-membered mono- or bicyclic ring system with one or more heteroatoms selected from the group consisting of nitrogen, sulfur, and oxygen, wherein the heteroatoms can also be present as functional groups, such as N-oxides, sulfur oxides, and sulfur dioxides, wherein the heterocyclic ring system may contain one or two double bonds, and wherein the monocyclic heterocyclic ring may be optionally fused to a heteroaryl, aryl, or a cycloalkyl ring optionally substituted with $C_1$-$C_5$ alkyl, halogens, hydroxy, amino, nitro, haloalkyl, alkylamino, carboxy, $NH(CO)R_8$, $NHS(O)_2R_8$, $NHC(O)NHR_9$, $NHSOR_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, or $NHC(O)NHS(O)_2R_8$. The possible substitutions of the heterocyclic ring systems include $C_1$-$C_3$ alkyl, dialkyl, and oxo groups. Examples of such heterocyclic ring radicals include but are not limited to imidazolidinone, isothiazolidine-1,1-dioxide, pyrrolidine, pyrrolidinedione, oxopyrrolidine, isoxazolidinedione, isoindoledione, morpholine, thiomorpholine, thiomorpholine-1,1-dioxide, thiophene-1,1-dioxide, thiazolidinedione, piperidine, piperazine, tetrahydro pyrimidinone, [1,2]-thiazinane-1,1-dioxide, tetrahydro thiophene-1,1-dioxide, piperidinone, and tetrahydrothiopyran-1,1-dioxide.

Further preferred heterocyclyl groups comprise

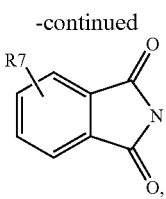

wherein $R_7$ is as described above and Z is $CH_2$, O, S, $SO_2$, NH, $NR_6$, or CH(OH). These examples do not limit the present invention.

$R_{12}$ is selected from hydrogen, halogen, haloalkyl, hydroxy, carboxy, nitro, amino, cyano, alkyl sulfinyl, alkylsulfonyl, alkylthio, amidinyl, alkoxy, alkoxy carbonylamino, ureido, thiureido, alkanoyl, alkanoyloxy, alkanoyl amino, carbamoyl, guanidyl, optionally substituted $C_1$-$C_8$ alkyl, and $C_2$-$C_6$ alkenyl.

$R_{13}$ is optionally substituted aryl, wherein the substituents may be the same or different and comprises at least one of the groups selected from
 a) hydrogen;
 b) $C_1$-$C_8$ alkyl, $C_2$-$C_6$ alkenyl, halo, alkylhalo, alkoxy, alkylsulfonyl, alkylsulfinyl, alkoxy, alkanoyl, alkanoyloxy, acylamino, carbonylamino, guanidyl, nitro, amino, $COOR_9$, $R_8NHC(O)R_9$, $COR_9$, $CONR_8R_9$, $NHC(O)OR_8$, $NHC(O)R_8$, $NHC(O)NR_8R_9$, $NHC(O)NR_8R_9$, $NHS(O)_2R_8$, $NHS(O)R_8$, $NHS(O)_2NHR_8$, $NHS(O)_2NHC(O)R_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $S(O)_2R_8$, $SOR_8$, $SR_8$, $S(O)_2NR_8R_9$, $OCF_3$, $OS(O)_2R_8$, or $OC(O)NR_8R_9$.
 c) Saturated, partially saturated, or unsaturated, mono- or bicyclic heterocyclic ring system optionally substituted by one or more groups selected from $C_1$-$C_3$ alkyl, $C_2$-$C_6$ alkenyl, dialkyl, and oxo, wherein the heterocyclic ring system is a 4- to 10-membered ring with one or more heteroatoms selected from the group consisting of nitrogen, sulfur, and oxygen, wherein the heteroatoms can also be present as functional groups, such as N-oxides, sulfur oxides, and sulfur dioxides. Examples of such heterocyclic ring radicals include, but are not limited to pyridine, pyrimidine, imidazolidinone, imidazolidinethione, indazole, indole, isoindole, quinazoline, quinoline, isoquinoline, cinnalone, isothiazolidine-1,1-dioxide, pyrrolidinone, 2-piperidinone, tetrahydropyrimidinone, azitidinone, and thiazane-1,1-dioxide.

Further preferred heterocyclyl groups comprise

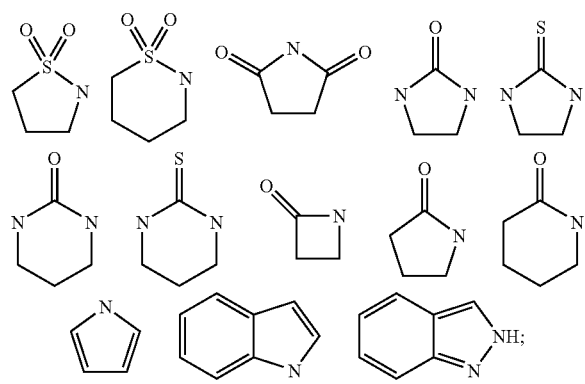

these examples do not limit the present invention.

The $R_8$, $R_9$, and $R_{10}$-groups, which are optionally substituted by halogen, hydroxy, alkoxy, cyano, nitro, alkyl, acyl, acyloxy, hydroxyalkyl, amino, alkylthio, or thioalkyl groups, may be the same or different and are individually selected from hydrogen, optionally substituted $C_1$-$C_8$ alkyl, aryl, arylalkyl, alkoxy carbonyl, and arylalkoxy carbonyl. When $R_8$ and $R_9$ are present together on a nitrogen atom they may form a 5- or 6-membered saturated, partially unsaturated, or unsaturated cyclic system containing carbon atoms, at least one nitrogen atom and optionally one or more other heteroatoms selected from oxygen, sulfur, and nitrogen.

Finally compounds of the invention are either obtained in free form or as a salt thereof, if salt forming groups are present. Compounds of the present invention may be converted into pharmaceutically acceptable salts by reacting them with appropriate acids or bases.

Certain compounds of the present invention of formula I may contain one or more chiral centers and the present invention incorporates the isolated stereoisomers, their mixtures, as well as the corresponding racemates.

Listed below are definitions of various terms used to describe this invention

The term "alkyl" refers to a saturated straight or branched aliphatic hydrocarbon chain that optionally may be substituted with multiple degrees of substitution. Examples of "alkyl" include but are not limited to methyl, ethyl, n-propyl, isopropyl, n-butyl, t-butyl, n-pentyl, and isobutyl. The substitutions may be selected from halogens, hydroxy, alkoxy, acyl, amino, and nitro. Unless specified differently, for example by the phrase "$C_x$-$C_y$ alkyl" which refers to an alkyl group with specified number of carbons, in the entire specification the term "alkyl group" refers to a $C_1$-$C_8$-group. A similar terminology applies to other preferred ranges as well.

The term "alkenyl" used herein, either alone or in combination with other radicals, denotes a straight or branched $C_2$-$C_6$ aliphatic hydrocarbon chain containing one or more carbon-to-carbon double bonds that may be optionally substituted with multiple degrees of substitution. The term "alkenyl" includes dienes and trienes of straight and branched chains and include groups such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, and 6-heptenyl The term "acyl" refers to a $C(O)R_a$-group, wherein $R_a$ is $C_1$-$C_4$ straight or branched alkyl or aryl.

The term "acylamino" used herein is represented by a —$NHC(O)R_a$-group, wherein $R_a$ is defined as above and examples are $CH_3CONH$, $C_2H_5CONH$, $C_3H_7CONH$, $C_6H_5CONH$.

The term "alkanoyloxy" refers to a —$OC(O)R_a$-group, wherein $R_a$ is $C_1$-$C_4$ straight or branched alkyl as defined above; examples are acetyloxy and propanyloxy.

The term "alkanoyl" refers to a —$C(O)R_a$-group, wherein $R_a$ is $C_1$-$C_4$ straight or branched alkyl as defined above; examples are acetyl and propanoyl.

The term "alkanoylamino" refers to a —NH—$C(O)R_a$-group, wherein $R_a$ is $C_1$-$C_4$ straight or branched alkyl as defined above; examples are $CH_3CONH$— and $C_2H_5CONH$—.

The term "alkoxy" refers to a —$OR_a$-group, wherein $R_a$ is alkyl as defined herein. Representative examples include but are not limited to methoxy and ethoxy.

The term "alkoxycarbonyl" refers to a —$C(O)OR_a$-group, wherein $R_a$ is alkyl as defined herein.

The term "Alkoxycarbonylamino" refers to a —NHC(O)$OR_a$-group where $R_a$ is alkyl as defined herein.

The term "alkylamino" refers to a —$N(R_a)_2$-group, wherein one $R_a$ is alkyl and the other $R_a$ is independently H or alkyl as defined herein.

The term "alkyl sulfinyl" refers to a —S(O)R$_a$-group, wherein R$_a$ is alkyl as defined herein.

The term "alkyl sulfonyl" refers to a —S(O)$_2$R$_a$-group, wherein R$_a$ is alkyl as defined herein The term "alkylthio" refer to a —SR$_a$-group, wherein R$_a$ is alkyl as defined herein. Representative examples include but are not limited to —S—CH$_3$, —S—CH$_2$CH$_3$.

The term "alkylhalo" refers to a R$_a$X-group, wherein R$_a$ is alkyl as defined above and X represents a halogen atom selected from fluorine, chlorine, bromine, and iodine.

The term "Halogen" refers to fluorine, chlorine, bromine, or iodine.

The term "hydroxyalkyl" refers to a R$_a$OH-group, wherein R$_a$ is alkyl as defined herein and representative examples include but are not limited to hydroxy methyl, hydroxy ethyl, and hydroxy propyl.

The term "aryl" refers to an aromatic ring system with five to ten carbon atoms, which may be monocyclic or bicyclic and unsaturated or partially saturated, and one or more carbons may optionally be replaced by one or more heteroatoms selected from N, O, and S. The term "aryl" includes ring(s) optionally substituted with multiple degrees of substitution and the substitutions may include alkyl, alkylene, Dialkyl, and oxo.

The term "aralkyl" refers to a Ar—R$_a$-group, wherein Ar and R$_a$ are as defined above.

The term "arylalkoxycarbonyl" refers to a —C(O)OR$_a$Ar-group, wherein Ar and R$_a$ are as defined above.

The term "heteroaryl" refers to a monocyclic aromatic ring system or a fused bicyclic aromatic ring system comprising two or more aromatic rings, preferably two rings. These heteroaryl rings contain one or more heteroatom, such as nitrogen, sulfur, and oxygen, wherein functional groups, such as N-oxides, sulfur oxides, and dioxides are permissible as heteroatom substitutions. The term "heteroaryl" includes optionally substituted ring systems. Examples of heteroaryl groups include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

The term "heterocyclyl" refers to a 3 to 15 membered ring that is either saturated or has one or more double bonds. These heterocyclic rings contain one or more heteroatoms such as nitrogen, sulfur, and/or oxygen atoms, wherein functional groups such as N-oxides, sulfur oxides, and dioxides are permissible heteroatom substitutions. Such ring may be optionally fused to one or more other heterocyclic ring(s), aryl ring(s) or cycloalkyl ring(s).

The term "stereoisomers" refers to certain compounds described herein that contain one or more chiral centres or may otherwise be capable of existing as multiple stereoisomers. Scope of the present invention includes pure stereoisomers, mixtures of stereoisomers such as purified enantiomers/diastereomers or enantiomerically/diastereomerically enriched mixtures, and racemates.

The term "bioisosteres" refers to compounds or groups that possess near molecular shapes and volumes, approximately the same distribution of electrons and which exhibit similar physical properties such as hydrophobicity. Bioisosteric compounds affect the same biochemically associated systems as agonist or antagonists and thereby produce biological properties that are related to each other.

The term "pharmaceutically acceptable salts" includes salts derived from inorganic bases such as Li, Na, K, Ca, Mg, Fe, Cu, Zn, Al, and Mn, salts of organic bases such as N,N'-diacetylethylenediamine, 2-dimethylaminoethanol, isopropylamine, morpholine, piperazine, piperidine, procaine, diethylamine, triethylamine, trimethylamine, tripropylamine, tromethamine, adamantyl amine, diethanolamine, ethylenediamine, N,N-benzyl phenylethylamine, choline hydroxide, dicyclohexylamine, metformin, benzylamine, phenylethylamine, dialkylamine, trialkylamine, thiamine, aminopyrimidine, aminopyridine, purine, pyrimidine, and spermidine, chiral bases like alkylphenylamine, glycinol, and phenyl glycinol, salts of natural amino acids such as glycine, alanine, valine, leucine, isoleucine, norleucine, tyrosine, cysteine, cystine, methionine, proline, hydroxy proline, histidine, ornithine, lysine, arginine, serine, threonine, and phenylalanine, unnatural amino acids such as D-isomers or substituted amino acids, salts of acidic amino acids such as aspartic acid and glutamic acid, guanidine, substituted guanidine wherein the substituents are selected from nitro, amino, alkyl, alkenyl, alkynyl, ammonium, or substituted ammonium salts. Salts may include acid addition salts such as sulphates, nitrates, phosphates, perchlorates, borates, hydrohalides selected from HCl, HBr, HI, acetates, tartrates, maleates, citrates, succinates, palmoates, methanesulfonates, benzoates, salicylates, hydroxynaphthoates, benzenesulfonates, ascorbates, glycerophosphates, and ketoglutarates.

The term "pharmaceutically acceptable solvates" refers adducts and co-crystallates, such as hydrates or solvates comprising other solvents, e.g. alcohols.

The term "compounds of the invention" or "present invention" refers to the compounds of the present invention represented by formula I as defined herein, their derivatives, their analogs, their tautomeric forms, their stereoisomers, their bioisosters, their diastereomers, their polymorphs, as well as their pharmaceutically acceptable salts and solvates.

The term "suitable pharmaceutically acceptable carriers" include solid fillers or diluents and sterile aqueous or organic solutions. The active ingredient will be present in such pharmaceutical compositions in amounts sufficient to provide the desired effect as described above. Thus, for oral administration, the compounds can be combined with a suitable solid, liquid carrier or diluent to form capsules, tablets, powders, syrups, solutions, suspensions etc. The pharmaceutical compositions may contain additional components such as flavourants, sweeteners, and excipients.

Preferred compounds of the present invention are represented by formula Ia and the generic structure given below. Additionally, preferred embodiments are represented by their derivatives, their analogs, their tautomeric forms, their stereoisomers, their bioisosters, their diastereomers, their polymorphs, their pharmaceutically acceptable salts and their pharmaceutically acceptable solvates.

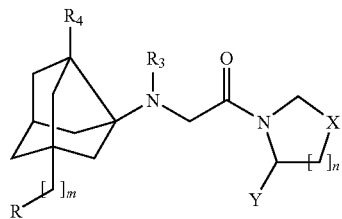

Ia wherein:
n=1 or 2
m=0, 1, or 2

X=CH$_2$, CHF, or S

Y=CN

R$_3$ is independently selected from hydrogen and C$_1$-C$_4$ alkyl

R$_4$ is hydrogen, C$_1$-C$_4$ alkyl, substituted alkyl, C$_1$-C$_4$ Alkoxy, alkanoyloxy, hydroxy, amino, nitro, C$_2$-C$_6$ alkenyl, acyl, or halogen R is R$_{11}$, R$_{12}$ or R$_{13}$ and R$_{11}$, R$_{12}$, R$_{13}$ are as defined above. Preferred compounds of the present invention comprise the following compounds:

(2S)-1-[1H-1,2,4-triazol-1-ylmethyl(tricyclo[3.3.1.0$^{3,7}$]non-3-ylamino)acetyl]pyrrolidine-2-carbonitrile (2S,4S)-4-fluoro-1-{N-[2-(1H-1,2,4-triazol-1-ylmethyl)hexahydro-2,5-methanopentalen-3a(1H)-yl]glycyl}pyrrolidine-2-carbonitrile (2S,4R)-4-fluoro-1-{N-[2-(1H-1,2,4-triazol-1-ylmethyl)hexahydro-2,5-methanopentalen-3a(1H)-yl]glycyl}pyrrolidine-2-carbonitrile (4R)-3-{N-[2-(1H-1,2,4-triazol-1-ylmethyl)hexahydro-2,5-methanopentalen-3a(1H)-yl]glycyl}-1,3-thiazolidine-4-carbonitrile (2S)-1-{N-[2-(1H-tetrazol-1-ylmethyl)hexahydro-2,5-methanopentalen-3a(1H)-yl]glycyl}pyrrolidine-2-carbonitrile (2S)-1-{N-[2-[(4-methylpiperazin-1-yl)methyl]hexahydro-2,5-methanopentalen-3a(1H)-yl]glycyl}pyrrolidine-2-carbonitrile (2S)-1-{N-[2-[(4-methylpiperazin-1-yl)methyl]hexahydro-2,5-methanopentalen-3a(1H)-yl]glycyl}pyrrolidine-2-carbonitrile hydrochloride salt (2S)-1-{N-[2-(thiomorpholin-4-ylmethyl)hexahydro-2,5-methanopentalen-3a(1H)-yl]glycyl}pyrrolidine-2-carbonitrile (2S)-1-{N-[2-(thiomorpholin-4-ylmethyl)hexahydro-2,5-methanopentalen-3a(1H)-yl]glycyl}pyrrolidine-2-carbonitrile hydrochloride salt (2S)-1-{N-[2-[(1,1-dioxidoisothiazolidin-2-yl)methyl]hexahydro-2,5-methanopentalen-3a(1H)-yl]glycyl}pyrrolidine-2-carbonitrile (2S)-1-{N-[2-[(2,4-dioxo-1,3-thiazolidin-3-yl)methyl]hexahydro-2,5-methanopentalen-3a(1H)-yl]glycyl}pyrrolidine-2-carbonitrile (2S)-1-{N-[2-[(1,3-dioxo-1,3-dihydro-2H-isoindol-2yl)methyl]hexahydro-2,5-methanopentalen-3a(1H)-yl]glycyl}pyrrolidine-2-carbonitrile ((2S)-1-{N-[2-(1,2,4-oxadiazol-3-ylmethyl)hexahydro-2,5-methanopentalen-3a(1H)-yl]glycyl}pyrrolidin-2-yl)acetonitrile (2S)-1-{N-[2-[4-(1,1-dioxidoisothiazolidin-2-yl)phenyl]hexahydro-2,5-methanopentalen-3a(1H)-yl]glycyl}pyrrolidine-2-carbonitrile (2S,4S)-1-{N-[2-[4-(1,1-dioxidoisothiazolidin-2-yl) phenyl]hexahydro-2,5-methanopentalen-3a(1H)-yl]glycyl}-4-fluoropyrrolidine-2-carbonitrile (2S,4R)-1-{N-[2-[4-(1,1-dioxidoisothiazolidin-2-yl)phenyl]hexahydro-2,5-methanopentalen-3a(1H)-yl]glycyl}-4-fluoropyrrolidine-2-carbonitrile (4R)-3-{N-[2-[4-(1,1-dioxidoisothiazolidin-2-yl)phenyl]hexahydro-2,5-methanopentalen-3a(1H)-yl]glycyl}-1,3-thiazolidine-4-carbonitrile (2S)-1-{N-[2-[4-(2-oxopyrrolidin-1-yl) phenyl]hexahydro-2,5-methanopentalen-3a(1H)-yl]glycyl}pyrrolidine-2-carbonitrile (2S,4S)-4-fluoro-1-{N-[2-[4-(2-oxopyrrolidin-1-1)phenyl]hexahydro-2,5-methanopentalen-3a(1H)-yl]glycyl}pyrrolidine-2-carbonitrile (4R)-3-{N-[2-[4-(2-oxopyrrolidin-1-yl)phenyl]hexahydro-2,5-methanopentalen-3a(1H)-yl]glycyl}-1,3-thiazolidine-4-carbonitrile (2S)-1-{N-[2-[4-(1H-pyrrol-1-yl)phenyl]hexahydro-2,5-methanopentalen-3a(1H)-yl]glycyl}pyrrolidine-2-carbonitrile (2S)-1-{N-[2-[4-(2-oxoimidazolidin-1-yl)phenyl]hexahydro-2,5-methanopentalen-3a(1H)-yl]glycyl}pyrrolidine-2-carbonitrile ((2S)-1-{N-[2-[4-(3-methyl-2-oxoimidazolidin-1-yl)phenyl]hexahydro-2,5-methanopentalen-3a(1H)-yl]glycyl}pyrrolidin-2-yl)acetonitrile (2S)-1-[(tricyclo[3.3.1.0$^{3,7}$]non-3-ylamino)acetyl]pyrrolidine-2-carbonitrile (2S)-1-[(tricyclo[3.3.1.0$^{3,7}$]non-3-ylamino)acetyl]pyrrolidine-2-carbonitrile hydrochloride salt (2S)-1-{[(1-hydroxytricyclo[3.3.1.0$^{3,7}$]non-3-yl)amino]acetyl}pyrrolidine-2-carbonitrile (2S)-1-{[(1-hydroxytricyclo[3.3.1.0$^{3,7}$]non-3-yl)amino]acetyl}pyrrolidine-2-carbonitrile hydrochloride salt (2S)-1-{[(1-methoxytricyclo[3.3.1.0$^{3,7}$]non-3-yl)amino]acetyl}pyrrolidine-2-carbonitrile (2S)-1-{[(1-methoxytricyclo[3.3.1.0$^{3,7}$]non-3-yl)amino]acetyl}pyrrolidine-2-carbonitrile hydrochloride salt (2S)-1-{[(1-ethoxytricyclo[3.3.1.0$^{3,7}$]non-3-yl)amino]acetyl}pyrrolidine-2-carbonitrile (2S)-1-{[(1-ethoxytricyclo[3.3.1.0$^{3,7}$]non-3-yl)amino]acetyl}pyrrolidine-2-carbonitrile hydrochloride salt (2S)-1-{[(1-aminotricyclo[3.3.1.0$^{3,7}$]non-3-yl) amino]acetyl}pyrrolidine-2-carbonitrile hydrochloride salt (2S)-1-[N-(2-fluorohexahydro-2,5-methanopentalen-3a(1H)-yl)glycyl]pyrrolidine-2-carbonitrile (2S)-1-[N-(2-fluorohexahydro-2,5-methanopentalen-3a(1H)-yl)glycyl]pyrrolidine-2-carbonitrile hydrochloride salt (2S)-1-{N-[2-(2-oxopyrrolidin-1-yl) hexahydro-2,5-methanopentalen-3a (1H)-yl]glycyl}pyrrolidine-2-carbonitrile (2S)-1-{N-[2-(2-oxopyrrolidin-1-yl) hexahydro-2,5-methanopentalen-3a (1H)-yl]glycyl}pyrrolidine-2-carbonitrile hydrochloride salt (2S)-1-{N-[2-(1,1-dioxidoisothiazolidin-2-yl)hexahydro-2,5-methanopentalen-3a (1H)-yl]glycyl}pyrrolidine-2-carbonitrile (2S)-1-{N-[2-(1,1-dioxidoisothiazolidin-2-yl) hexahydro-2,5-methanopentalen-3a (1H)-yl]glycyl}pyrrolidine-2-carbonitrile hydrochloride salt (2S)-1-[N-(2-phenylhexahydro-2,5-methanopentalen-3a (1H)-yl)glycyl]pyrrolidine-2-carbonitrile (2S)-1-[N-(2-phenylhexahydro-2,5-methanopentalen-3a (1H)-yl)glycyl]pyrrolidine-2-carbonitrile hydrochloride salt (2S)-1-{N-[2-(4-nitrophenyl)hexahydro-2,5-methanopentalen-3a(1H)-yl]glycyl}pyrrolidine-2-carbonitrile (2S)-1-{N-[2-(4-aminophenyl)hexahydro-2,5-methanopentalen-3a(1H)-yl]glycyl}pyrrolidine-2-carbonitrile Another aspect of the present invention provides processes for the preparation of the compounds of general formula I as described above.

Scheme I:

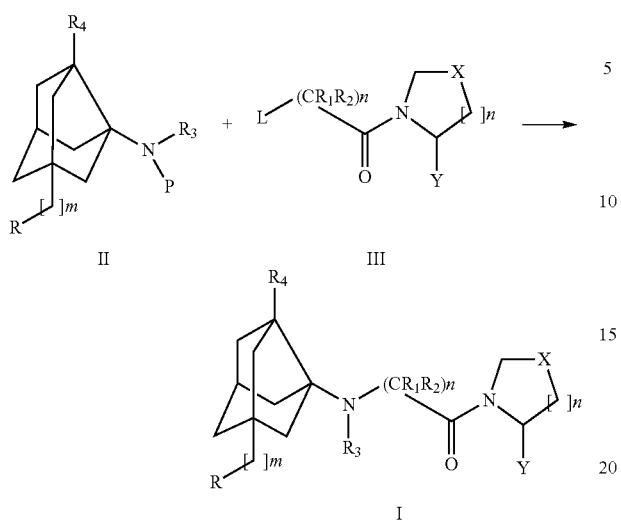

wherein
P is H or a protecting group
L is a leaving group selected from the group consisting of halogens, tosylates, mesylates, and triflates
R, $R_1$, $R_2$, $R_3$, $R_4$, n, m, X, and Y are as described above
Compounds of formula I are prepared by the following steps comprising:
  a. Coupling one equivalent of a compound of formula III with about 1 to 5 equivalents of an amine compound of formula II in its free form or as a salt or as a compound, wherein the amine is protected, in the presence of one or more bases, such as but are not limited to alkali metal hydrides like NaH and KH; organolithiums such as $CH_3Li$ and BuLi; alkoxides like NaOMe, NaOEt, and KOtBu; tertiary amines like triethylamine and DBU; carbonates like potassium carbonate, potassium bicarbonate, sodium carbonate, and cesium carbonate.
  b. Said coupling is carried at a temperature ranging from about −5° C. to about 120° C. in an inert solvent such as dichloromethane, dimethyl formamide, tetrahydrofuran, acetonitrile, DMSO etc.
  c. Said coupling is carried for 0.5 to 72 hours, preferably for 0.5 to 60 hours.
  d. Isolating the resulting compound of formula I.

The compounds of formula III can be prepared by methods found in the state of the art (WO 2003/002553, WO 00/034241, WO 98/19998, US 2005/0038020, *Bioorganic and Medicinal Chemistry Letters* 1996, 6, 1163-66, *Journal of Medicinal Chemistry* 2003, 46, 2774-2789)

Intermediate II can be obtained via a reaction sequence which is summarized in schemes II and III.

Scheme II:

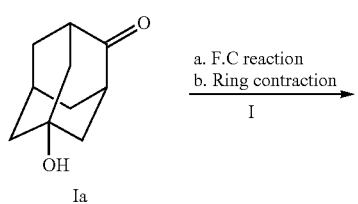

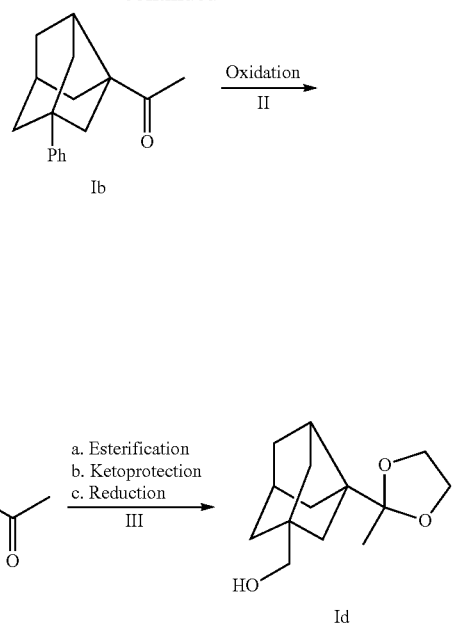

Scheme II is described in the following steps comprising:
  1a. Friedel Crafts reaction of benzene with 5-hydroxy adamantanone in presence of triflic acid over a period of about 1-4 h at reflux temperature to obtain 5-phenyl adamantan one.
  1b. Ring contraction of adamantanone to noradamantanone takes place in 2 steps first by converting to 2-methyl-5-phenyl adamantan-2-ol by Grignard reaction, wherein the Grignard reagent is selected from the group comprising methyl metal halides like $CH_3MgCl$, $CH_3MgBr$, $CH_3MgI$ followed by ring contraction in presence of an oxidizing agent in solvents like water, THF, benzene, or a combination of the said solvents followed by treatment with a base in a protic solvent such as water, alcohols to form Ib. Preferred alcohols are $C_1$-$C_4$ alcohols and the base is selected from alkalis like NaOH and KOH. The oxidising agent may be selected from chlorine monoxide, hypochlorites like NaOCl or lead tetraacetate in the presence of iodine.

II. The phenyl group of compound Ib is converted to a carboxylic acid group in the presence of an oxidizing agent like $NaIO_4/RuCl_3$ at ambient temperature to form Ic.

III. The carboxylic group of compound Ic is converted to its alkyl ester, the keto group is protected with an 1,2-diol such as 1,2-ethane diol or an 1,3-diol such as 1,3-propane diol in the presence of organic solvents like benzene or toluene at their reflux temperature using an acid catalyst such as p-TSA, CSA, and $BF_3$ etherate. In the next step, the ester is reduced to the alcohol by a reducing agent such as $LiAlH_4$, $NaBH_4$, and DIBAL-H in an inert solvent like THF, ether, or mixtures thereof at a temperature of about 0° C. to form Id.

Scheme III:

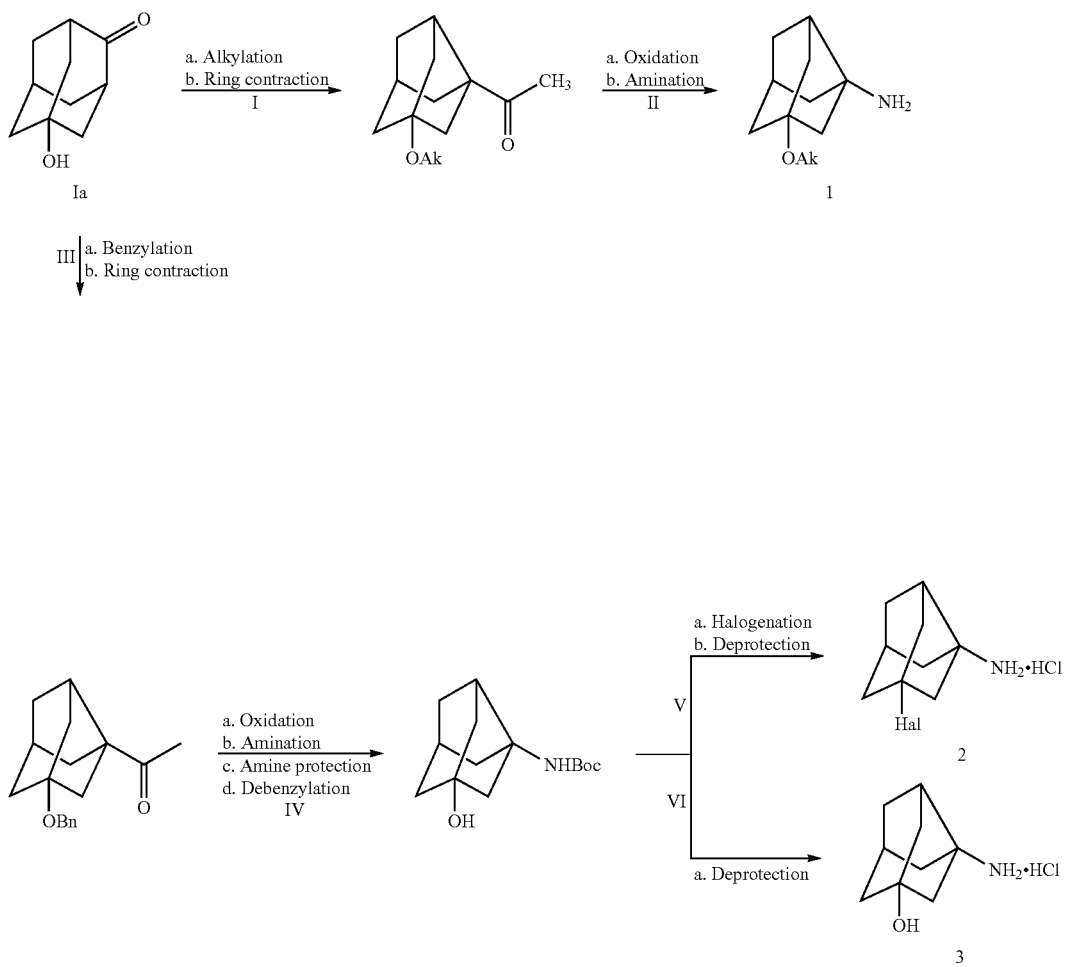

Scheme III is described in the following steps:

Ia. The hydroxy group of Ia, at 5$^{th}$ position is alkylated by an alkylating agent like alkyl halides (such as $CH_3I$, $CH_3Br$ or isopropyl bromide) using strong bases such as NaH, KH, or $NaOCH_3$ to form 5-hydroxy adamantanone; followed by ring contraction.

Ib. 5-alkoxy adamantanone is converted to 5-alkoxy noradamantyl ethanone by converting it to 2-methyl-5-alkoxy adamantan-2-ol by Grignard-reaction followed by ring contraction of adamantanone to noradamantane in the presence of an oxidizing agent in a solvent like water, THF, benzene, or a combination of such solvents followed by the treatment with a base in a protic solvent such as water, alcohols, or mixtures thereof to form 5-alkoxy noradamantyl ethanone.

IIa. The ethanone group in the compound obtained by step 1 is converted to a carboxylic acid by treatment with an oxidizing agent like hypobromites, hypochlorites (such as NaOBr, NaOCl), etc. at about 0° C. followed by an amination step.

IIb. Conversion of the acid to an amine-function by treatment with an azide like $NaN_3$ or $nBu_4NN_3$ under acidic conditions in the presence of solvents like $CHCl_3$, $CH_2Cl_2$, $CH_3CN$ at a temperature of about 35 to 50° C. to obtain alkoxy noradamantylamines (1).

IIIa. In another route, the hydroxyl group of compound Ia is benzylated by reaction with benzylhalides like benzylbromide in a solvent (e.g., THF, DMF, NMP) at about 0° C. for about 10-18 hrs to form benzyloxy adamantanone followed by ring contraction to form benzyloxy noradamantyl ethanone.

IV. The benzyloxy noradamantyl ethanone obtained in step III is converted to the corresponding acid by an oxidizing agent followed by an amination step (b). The amine thus formed is protected by conventional amine protecting groups like Boc, Cbz or Fmoc followed by debenzylation (d). The debenzylation is carried out in a $H_2$ atmosphere under Pd/C-catalysis in protic solvents like methanol, ethanol or IPA at room temperature for 1-3 hrs to form hydroxy noradamantyl amine, wherein the amine group is protected.

V. Halogenation of the hydroxyl group followed by deprotection of the amine of the compound obtained from step IVd yields a halosubstituted noradamantylamine in salt form 2.

VI. Deprotection of the amine of the compound obtained from IVd step yields a hydroxy-substituted noradamantylamine in salt form 3.

Thus obtained intermediate compounds 1, 2, 3 are reacted with chloroacetylcyano pyrrolidines to form the corresponding final compounds according to Scheme I

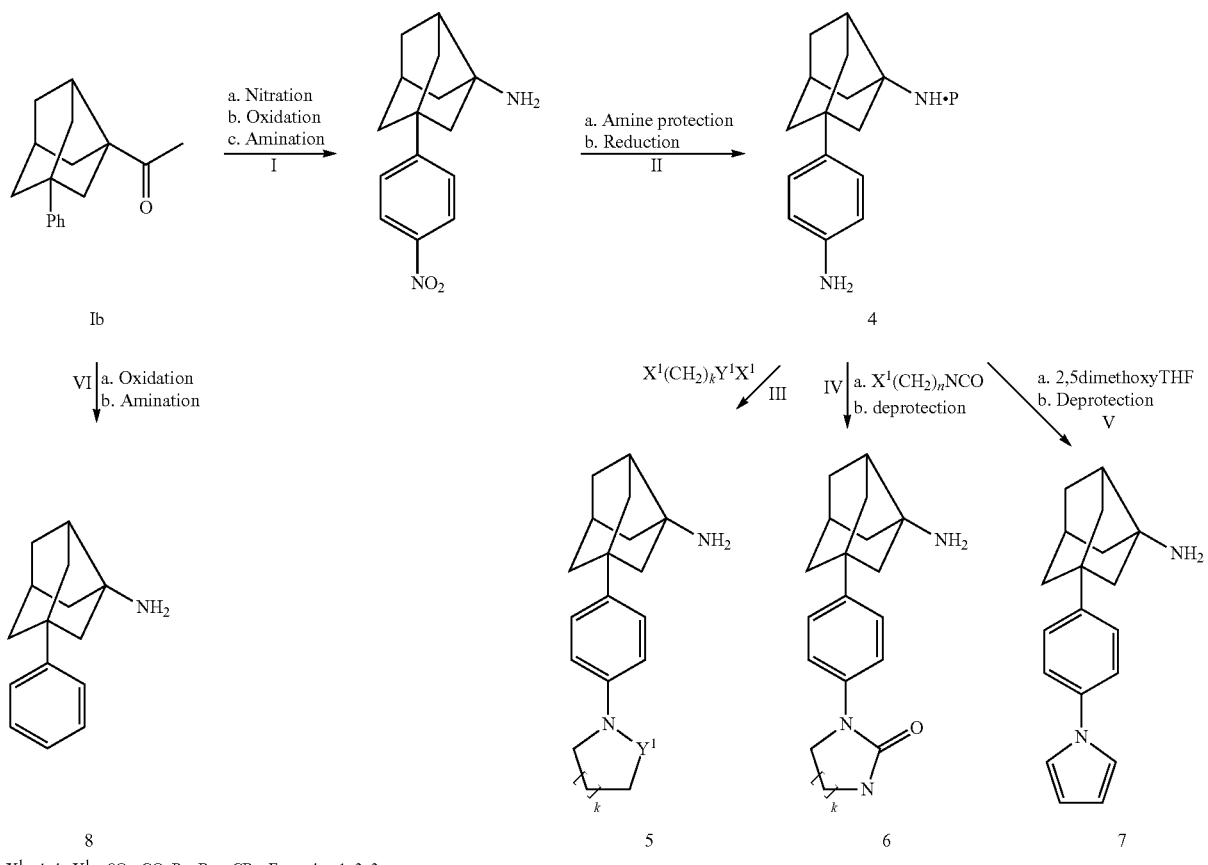

Scheme IV $X^1$ = halo; $Y^1$ = $SO_2$, CO; P = Boc, CBz, Fmoc; k = 1, 2, 3

Scheme IV is described by the following

Ia. The phenyl group of compound Ib (as obtained in scheme I) is nitrated by a nitrating mixture in a conventional procedure by $HNO_3/H_2SO_4$ at about 0° C.

Ib. The nitrophenyl noradamantyl ethanone obtained in step Ia is oxidized to convert the ethanone to the corresponding acid by an oxidizing agent followed by an amination step.

Ic. The conversion of the acid to the amine is carried out by treatment with an azide like $NaN_3$ or $n-Bu_4NN_3$ under acidic conditions in the presence of solvents like $CHCl_3$, $CH_2Cl_2$, or acetonitrile at a temperature of about 35 to 50° C.

IIa. The amine group in the compound obtained from step I is protected by a conventional amine protecting group like Boc, Cbz, or Fmoc.

IIb. The nitro group is reduced to an amine by reducing agents such as Pd/C, $Pd(OAc)_2$, Zn/ammonium formate, or $Fe/NH_4Cl$ etc. in the presence of solvents like esters (e.g., ethyl acetate), alcohols (e.g., methanol, ethanol), THF, water or a combination thereof to form the phenyl amino compound (4).

III. The phenyl amino compound (4) obtained by step II is reacted with $X^1(CH_2)_nY^1X^1$, wherein $X^1$ is a halo group selected from F, Cl, Br, I, $Y^1$ is $SO_2$ or CO, in the presence of an organic base like triethylamine or DBU and an inert solvent like THF, $CH_2Cl_2$, acetonitrile, or DMF followed by cyclization in the presence of alkali metal hydroxides such as LiOH, NaOH, or KOH in water with phase transfer catalyst such as tetraalkylammonium halides (e.g., tetrabutyl ammoniumiodide) and deprotection of the amine protecting group to get the corresponding heterocycle substituted phenyl noradamantyl amine compound (5).

IV. In another method compound (2) obtained from step II is reacted with $X_1(CH_2)NCO$ in the presence of organic bases like triethylamine or DBU, a solvent like THF, $CH_2Cl_2$, acetonitrile, DMF, or mixtures thereof; followed by cyclization to obtain the corresponding heterocycle substituted compound, which, by further amine deprotection, form the corresponding heterocycle substituted phenyl noradamantyl amine compounds (6).

V. In another method, the phenyl amino compound (2) obtained from step II is reacted with 2,5-dimethoxy tetrahydrofuran in glacial acetic acid at reflux temperature to form pyrrole substituted compounds, which, on further amine deprotection, form the corresponding pyrrole substituted phenyl noradamantyl amine compounds (7).

VIa. The ethanone group of the phenylnoradamantylethanone (Ib) (as obtained in scheme II) is converted to an acid-group by an oxidizing agent followed by an amination step.

VIb. Conversion of acid to amine by azides as described above, form the corresponding phenyl substituted noradamantylamine compounds (8).

The obtained intermediate amine compounds 4, 5, 6, 7, 8 are reacted with chloroacetylcyano pyrrolidines to form the corresponding final compounds according to Scheme I.

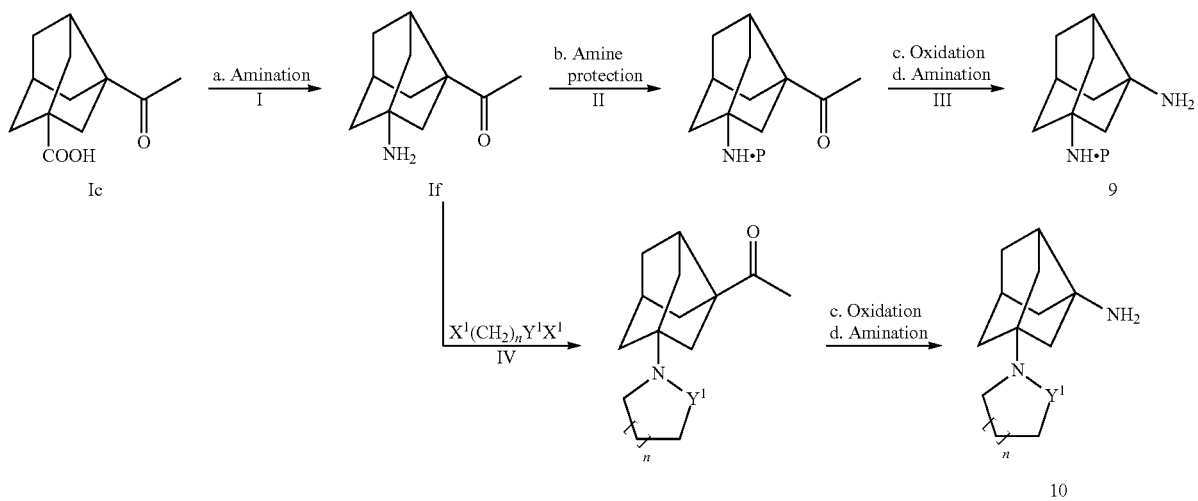

Scheme V is described by the following:

Ia. The carboxylic acid group of compound Ic (obtained via scheme II) is converted to the amine by treatment with an azide like NaN$_3$ in an acidic medium or with diphenylphosphorylazide in the presence of organic bases like triethylamine, solvents like benzene or toluene at reflux temperature.

IIb. The amine group of compound If obtained from step I, is protected with a conventional amine protecting group like Boc, Cbz, or Fmoc, followed by an oxidation step.

IIIc. The oxidation of the compound obtained by step II is carried out by oxidizing agents to obtain a carboxylic acid derivative.

IIId. This carboxylic acid group of the compound obtained from step Mc is converted to an amine by azide-treatment with e.g. NaN$_3$ in an acidic medium or with diphenylphosphorylazide in the presence of organic bases like triethylamine, in a solvent like benzene or toluene at reflux temperature followed by hydrolysis with a metal hydroxide such as KOH, NaOH, LiOH in water at room temperature to form the corresponding amine substituted noradamantylamine (9).

IV. The amino compound (If) obtained from step I is reacted with X$^1$(CH$_2$)$_n$Y$^1$X$^1$, wherein X$^1$ is halogen and Y$^1$ is —SO$_2$— or —CO— in the presence of organic bases like triethylamine and a solvent like THF or CH$_2$Cl$_2$ followed by cyclization using alkalimetal hydroxides in water with a phase transfer catalyst such as tetrabutylammonium iodide to get the corresponding heterocycle substituted compounds with an ethanone group, which, after oxidation and amination steps as described in IIIc and IIId, is converted to the corresponding heterocycle substituted noradamantylamines (10).

The obtained amine intermediate compounds 9, 10 are reacted with chloroacetylcyano pyrrolidines to form the corresponding final compounds according to Scheme I.

Scheme VI:

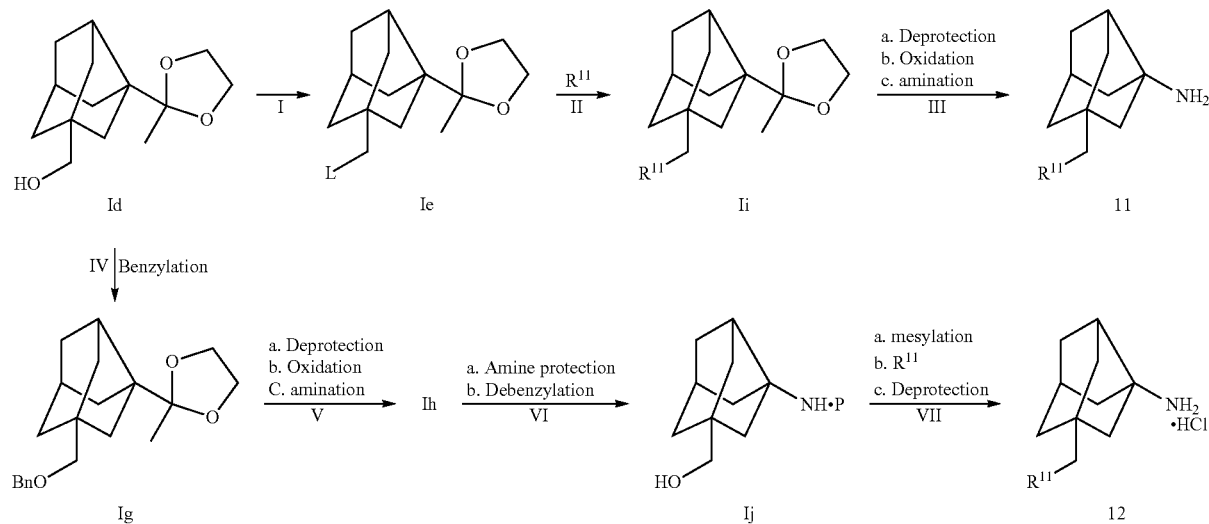

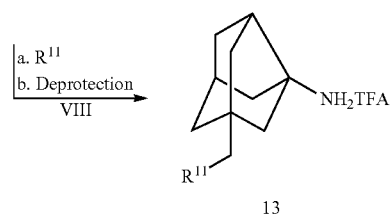

Scheme VI is described by the following:

I. To yield compound Ie, the hydroxyl group of compound Id is transformed into a leaving group L by e.g. messylation, tosylation, or halogenation in the presence of an organic base like triethylamine, N,N-diisopropyl-ethylamine, pyridine, NMP, or N-methylmorpholine at a temperature of about 0° C.

II. The leaving group L of Ie is replaced by $R^{11}$ group in the presence of a base and a solvent at a temperature of about 80-120° C. to form Ii. The bases are selected from alkali carbonates or bicarbonates like $Na_2CO_3$, $NaHCO_3$, $K_2CO_3$, or $KHCO_3$. The solvents are selected from dimethylformamide, DMSO, NMP, or similar.

IIIa. The protected keto group of compound II obtained from step II is deprotected by, e.g., reaction with p-TSA in acetone at reflux temperature to form an ethanone compound.

IIIb. The ethanone compound is oxidized to the corresponding carboxylic acid in the presence of an oxidizing agent, which may be selected from chlorine monoxide, hypochlorites like NaOCl or lead tetraacetate in the presence of iodine.

IIIc. The carboxylic acid is converted to an amine by reaction with an azide like $NaN_3$ under acidic conditions in the presence of solvents like $CHCl_3$, $CH_2Cl_2$, or acetonitrile at about 35 to 45° C. to form the $R^{11}$ substituted noradamantylamine (11).

IV. In another route, the hydroxyl group of Id as obtained from scheme II, is benzylated by reaction with benzylhalides like benzylbromide in solvents like THF, DMF, or NMP at about 0° C. for about 10-18 hrs to form the keto protected benzyloxy noradamantane (Ig).

Va. The protected keto group of compound Ig is deprotected to obtain the ethanone as described in step IIIa.

Vb. The ethanone group of the benzyloxy noradamantylethanone compound is oxidized to yield the carboxylic acid as described in step IIIb.

Vc. The carboxylic group of the compound obtained from step Vb is converted to an amine by reaction with diphenylphosphorylazide in the presence of organic bases like triethylamine, solvents like benzene, or toluene at reflux temperature followed by hydrolysis with metal hydroxides such as KOH, NaOH, or LiOH in water at room temperature to form benzyloxy noradamantylamine (Ih).

VIa. The amine group of the compound Ih obtained from step Vc is protected by conventional amine protecting groups as described earlier followed by a debenzylation step.

VIb. The debenzylation is carried out in the presence of $H_2$ atmosphere over Pd/C in protic solvents like methanol, ethanol, or IPA at room temperature for 1-3 hrs to form compound Ij.

VIIa. The hydroxyl group of compound Ij is mesylated, tosylated, or halogenated to form a leaving group in the presence of organic bases like triethylamine, N,N-diisopropyl ethylamine, pyridine, N-methyl-piperidine, or N-methylmorpholine at ambient temperature.

VIIb. The compound obtained from VIIa is reacted with a $R^{11}$ group in the presence of a base and a solvent at a temperature range of about 80-120° C. The bases are selected from alkali carbonates or bicarbonates like $Na_2CO_3$, $NaHCO_3$, $K_2CO_3$, and $KHCO_3$. Solvents are selected from DMF, DMSO, NMP etc.

VIIc. The protected amine group of the $R^{11}$ substituted compound obtained from step VIIb is deprotected by conventional methods, e.g. by treatment with dry HCl in solvents like EtOAc, ether, or 1,4-dioxane at a temperature between 0° C. and room temperature to form a $R^{11}$-substituted noradamantylamine as hydrochloride salt (12).

VIIIa. In another method, the hydroxyl group of Ij is reacted with the $R^{11}$ group in the presence of triphenylphosphine, diisopropylazodicarboxylate, and an organic solvent like benzene, toluene, or THF at a temperature from about 20° C. to about 110° C. for about 2-6 hours to form the $R^{11}$-substituted compound.

VIIIb. The protected amine group of the $R^{11}$-substituted compound obtained from step VIIIa is deprotected by treatment with trifluoroacetic acid in a solvent like $CH_2Cl_2$ or $CHCl_3$ at about 0° C. to form the $R^{11}$-substituted noradamantanamine as a TFA salt (13).

The obtained intermediate compounds 11, 12, 13 are reacted with chloroacetylcyano pyrrolidines to form the corresponding final compounds according to Scheme I.

Scheme VII:

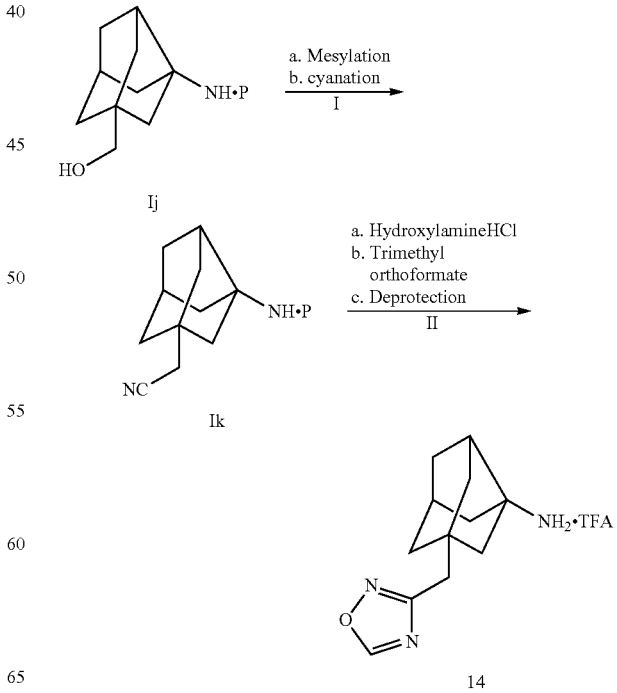

Scheme VII is described by the following:

Ia. To form a leaving group L, the hydroxy group of compound Ij is mesylated, tosylated, or halogenated in the presence of organic bases like triethylamine, N,N-diisopropyl ethylamine, pyridine, N-methyl-piperidine, or N-methyl-morpholine at an ambient temperature. The compound obtained from Ia is reacted with a cyanating agent like NaCN in the presence of an aprotic solvent like DMF at 100-110° C. for about 12-15 hrs to obtain a compound (Ik).

IIa. Compound Ik is reacted with hydroxylamine hydrochloride to form amidoxime, which upon reaction with trimethylorthoformate in the presence of a catalytic amount of camphor sulfonic acid. Final deprotection yields compound 14.

The obtained intermediate compound 14 is reacted with chloroacetylcyano pyrrolidines to form the corresponding final compounds according to Scheme I.

It is understood that in any of the above schemes any reactive group in the substrate molecule may be protected according to any conventional procedure known in the prior art.

Suitable protecting groups comprise tertiarybutyldimethylsilyl, methoxymethyl, triphenyl methyl, benzyloxycarbonyl, THP etc. for the protection of hydroxyl or phenolic hydroxy groups; N-Boc, N-Cbz, N-Fmoc, and benzophenoneimine for the protection of amino or anilino groups; acetal protection for aldehydes, ketal protection for ketones. The methods for the formation and removal of such protecting groups depend on the molecule to be protected which are known in the art.

Also as part of the invention, in carrying out the invention wherever there is a leaving group it may be selected from the group comprising halogens (like chlorine, bromine), o-toluene sulphonyl, o-methyl sulphonyl.

The stereoisomers of the compounds according to this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, or lactic acid wherever applicable or chiral bases such as brucine, cinchona alkaloids, or their derivatives.

The pharmaceutically acceptable salts can be prepared by reacting the compound of formula I with about 1 to 5 equivalents of bases such as alkalimetal hydroxides, alkalimetal alkoxides, calcium hydroxide, or magnesium hydroxide in protic or aprotic solvents like methanol, ethanol, propanol, IPA, ether, THF, dioxane etc. Alternatively, wherever applicable acid addition salts are prepared by treatment with acids such as hydrohalic acids like HCl, HBr; nitric acid, sulfuric acid, phosphoric acid, p-toluene sulphonic acid, methane sulphonic acid, acetic acid, or citric acid in solvents comprising at least one selected from ethyl acetate, ethers, alcohols, acetone, THF, dioxane, or mixtures thereof.

Different polymorphs of a compound of general formula I of the present invention may be prepared by crystallization of the compound of formula I under different conditions. For example making use of commonly used solvents or their mixtures for recrystallization, crystallization at different temperature ranges, different cooling techniques like very fast to very slow cooling during crystallization, by exposing the compound to ambient temperature, by heating or melting it followed by gradual cooling etc. The presence of polymorphs may be determined by one or more methods like solid probe NMR spectroscopy, DSC, TGA, Powder X-Ray diffraction or IR.

In another embodiment of the present invention, the compounds may be purified by using techniques such as crystallization from solvents such as pentane, diethylether, isopropyl ether, chloroform, dichloromethane, ethylacetate, acetone, methanol, ethanol, isopropanol, water, or their combinations, or compound I may be purified by column chromatography using alumina or silica gel and eluting the column with solvents such as hexane, petroleum ether, dichloromethane, chloroform, ethylacetate, acetone, methanol, or combinations thereof.

The present invention also provides pharmaceutical compositions containing the compounds as defined above, their derivatives, their analogs, their tautomeric forms, their stereoisomers, their bioisosters, their polymorphs, their enantiomers, their diastereomers, their pharmaceutically acceptable salts, or their pharmaceutically acceptable solvates in combination with suitable pharmaceutically acceptable carriers or diluents. The pharmaceutical compositions according to the present invention are useful as antidiabetics, hypolipidemics and antihypercholesterolemics.

Suitable pharmaceutically acceptable carriers include solid fillers, diluents, and sterile aqueous or organic solutions. The active ingredient will be present in such pharmaceutical compositions in amounts sufficient to provide the desired effect as described above. Thus, for oral administration, the compounds can be combined with a suitable solid or liquid carrier or a diluent to form e.g. capsules, tablets, powders, syrups, solutions, or suspensions. The pharmaceutical compositions, may, if desired, contain additional components such as flavourants, sweeteners, or excipients.

The route of administration may be oral, nasal, pulmonary, buccal, subdermal, intradermal, transdermal, or parenteral e.g. rectal, depot, subcutaneous, intravenous, intraurethral, intramuscular, intranasal, as an ophthalmic solution or an ointment, which effectively transports the active compound of the present invention which inhibits the DPPIV enzymatic activity to the appropriate or desired site of action. For oral administration, if a solid carrier is used, the preparation may be in form of tablet, or may be placed in a hard gelatin capsule in powder or pellet form, or it can be in form of a troche or a lozenge. If a liquid carrier is used, the preparation may be in the form of a syrup, emulsion, soft gelatin capsule, or a sterile injectable liquid such as an aqueous or non aqueous liquid suspension or solution. For nasal administration a liquid carrier, in particular an aqueous carrier, is used as an aerosol application. For parenteral application, suitable compositions are injectable solutions or suspensions, preferably aqueous solutions.

A further aspect of the present invention is the use of compounds of the invention as a pharmaceutical composition in a therapeutically effective amount for the treatment of metabolic disorders, blood glucose lowering, for the treatment of type II diabetes, for the treatment of impaired glucose tolerance, for the treatment of impaired fasting glucose, for the treatment of obesity, for the prevention of hyperglycemia, for the treatment of dislipidemia, hypercholesteromia, and hypolipidemia.

The compounds of the present invention are effective over a wide dosage range. For example in the treatment of humans, dosages may be about 0.05 to 1000 mg, and preferably about 0.1 to 500 mg per day. The exact dosage depends on the mode of administration, on the therapy required, the form in which the active ingredient is administered and the patient to be treated; the body weight of the subject to be treated and the preference and experience of the physician in charge. Here, the subject is considered as a human being.

The invention also encompasses prodrugs of compounds of the invention, which on administration undergo chemical conversion by metabolic processes before becoming active pharmacological substances. In general, such prodrugs will be functional derivatives of compounds of the invention, which are readily convertible in vivo into compounds of the invention.

The invention also encompasses the active metabolites of the compounds of the present invention.

Assay of Dipeptidyl Peptidase IV Activity

The inhibition of proteolytic activity of DPP-IV was assayed by following the hydrolysis of Ala-Pro-7-amino-4-trifluoromethylcoumarin (Ala-Pro-AFC) and fluorometric quantitation of the liberated AFC. Human recombinant DPP-IV (expressed in insect Sf9 cells) was used for the assay. Test compounds were dissolved in dimethyl sulfoxide (DMSO). Generally, the enzyme (about 20 ng/ml in 100 mM Tris-HCl buffer, pH 8.0) was preincubated in the absence (1% DMSO) and presence of various concentrations of the test compounds for 15 min at 37° C. The reaction was initiated by the addition of 20 μM Ala-Pro-AFC and further incubated for 30 min at 37° C. The AFC liberated was measured in a spectrofluorometer with excitation and emission wavelengths set at 400 nm and 510 nm, respectively. Results are expressed as percent inhibition of enzyme activity. A reference standard (a known inhibitor of DPP-IV) was always included in the assay.

The compounds of the present invention were found to inhibit DPPIV induced fluorescence with inhibitory constants in a range of about 0.5 nM to 500 nM. In a preferred range, the compounds of the present invention inhibited DPPIV induced fluorescence with inhibitory constants of about 0.1 nM to 300 nM and in a more preferred range the compounds of the present invention inhibited DPPIV induced fluorescence with inhibitory constants of about 1 nM to 120 nM.

As shown in the Table below, the examples exerted potent inhibition of DPP-IV.

| Compound | $IC_{50}$ value in nM |
| --- | --- |
| Example 1 | 8.1 |
| Example 2 | 2.8 |
| Example 3 | >300 |
| Example 4 | 7 |
| Example 5 | 11 |
| Example 6 | 100 |
| Example 7 | 30 |
| Example 8 | 22 |
| Example 9 | 31.2 |
| Example 10 | ~30 |
| Example 11 | 20 |
| Example 12 | 5 |
| Example 13 | 300 |
| Example 14 | 6.4 |
| Example 15 | 4 |
| Example 16 | 0.95 |
| Example 17 | 8.7 |
| Example 18 | ~30 |
| Example 19 | 15.4 |
| Example 20 | 30 |
| Example 21 | 64.5 |
| Example 22 | 30 |
| Example 23 | 11.9 |
| Example 24 | 100 |
| Example 25 | 100 |
| Example 26 | 21.8 |
| Example 27 | 30 |

-continued

| Compound | $IC_{50}$ value in nM |
| --- | --- |
| Example 28 | 30 |
| Example 29 | ~30 |
| Example 30 | ~32.4 |
| Example 31 | 21.0 |
| Example 32 | 53.6 |

The following examples are provided to enable one skilled in the art to practice the invention and are merely illustrative of the invention but do not limit the scope of the invention.

Preparation I 1-(1-Phenyltricyclo[3.3.1.0$^{3,7}$]non-3-yl)ethanone

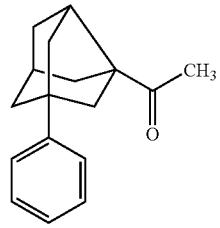

Step I: Adamantanone (12 g, 80 mmol) was added under stirring to nitric acid (98%, 100 mL) at ice bath temperature over a period of 15 minutes. The reaction mixture was stirred at room temperature for 72 h and then heated to 60° C., for 2 h until most of the nitrogen dioxide evaporated. Excess nitric acid was distilled off under reduced pressure. The light yellow oil solidified upon cooling ($NO_3$ adduct of the hydroxyketone). Water (40 mL) and conc. $H_2SO_4$ (98%, 15 mL) were added. The resulting clear yellow solution was heated on the steam bath in a hood (nitrous fumes) for 1 h. The solution was then cooled and extracted with a 2:1 mixture of n-hexane and diethylether to remove unreacted adamantanone (1.0 g). The acid layer was neutralized with 30% aq. NaOH solution, and while warm, extracted with chloroform. The extracts were combined, washed with brine solution, and concentrated in vacuum. The crude product was dissolved in $CH_2Cl_2$ (15 mL) and hexane was added until no more precipitate was formed. The solid material was isolated by filtration and dried to get 5-hydroxy-adamantan-2-one. Yield: 9.0 g (70%). Solid; M.R: 278.8-300° C. (decomposes) m/z (M+1) 167; $^1$H NMR (CDCl$_3$) 300 MHz δ 2.70-2.55 (m, 2H), 2.36-2.32 (m, 1H), 2.11-1.93 (m, 10H). $^{13}$C NMR (CDCl$_3$) 75 MHz δ 217.0, 66.7, 46.7, 46.6, 44.7 (2C), 43.8, 37.9 (2C), 29.5.

Step II: To a stirred solution of compound 5-hydroxyadamantan-2-one (10.0 g, 60.2 mmol) in benzene (180 mL) was added trifluoromethanesulfonic acid (5.3 mL, 60.2 mmol) over a period of 30 minutes at r.t. After stirring the reaction mixture for 5 minutes at r.t, it was refluxed for 4 h. The reaction mixture was cooled to 0° C. and sat. aq. NaHCO$_3$ (76 mL) was added over a period of 30 minutes. Two layers were separated, the aqueous layer was extracted with ether and the combined layer was washed with water and brine, dried over anhydrous Na$_2$SO$_4$, and the solvent was evaporated under reduced pressure to obtain 5-Phenyladamantan-2-one (10.5 g) as a white solid in 80% yield. M.R: 53.8-60.9° C. m/z (M+1) 227; IR (cm$^{-1}$): 2921, 2853, 1717, 1446, 1060, 758, 698. $^1$H NMR (CDCl$_3$) 300 MHz δ 7.37-7.30 (m, 4H), 7.26-

7.19 (m, 1H), 2.70-2.63 (m, 2H), 2.30-2.0 (m, 11H). $^{13}$C NMR (CDCl$_3$) 75 MHz δ 217.8, 147.8, 128.3 (2C), 126.1, 124.6 (2C), 46.9 (2C), 44.3 (2C), 41.9, 35.9, 38.4 (2C), 28.0.

Step III: Freshly prepared methylmagnesium iodide in ether (1 M, 85 mL), was added through a canola to 5-phenyladamantan-2-one (9.6 g, 42.5 mmol) obtained in step II, in THF (85 mL) at 0° C. After stirring at 0° C. for 0.5 h, the reaction mixture was quenched by adding sat. aq. NH$_4$Cl solution. The organic layer was separated and the aqueous layer was extracted with diisopropylether. The combined organic layers were washed with water and brine, dried over anhydrous Na$_2$SO$_4$, and the solvent was removed under reduced pressure to obtain 2-methyl-5-phenyl-adamantan-2-ol (9.9 g) as an off-white solid in 97% yield. M.R: 98-100.4° C. m/z (M+23) 265; $^1$H NMR (CDCl$_3$) 300 MHz δ 7.42-7.28 (m, 4H), 7.24-7.18 (m, 1H), 2.47-2.26 (m, 2H), 2.14-2.09 (m, 3H), 1.96-1.70 (m, 6H), 1.61-1.57 (m, 2H), 1.42 (s, 3H). $^{13}$C NMR (CDCl$_3$) 75 MHz δ 150.0, 128.1 (2C), 125.7, 124.8 (2C), 73.3, 44.0 (2C), 40.5 (2C), 39.6 (2C), 35.9, 32.0, 27.6.

Step IV: 2-Methyl-5-phenyl-adamantan-2-ol (20 g, 82.6 mmol) obtained in step III, (86 g, 355.4 mmol), dissolved in a mixture of AcOH (76.3 mL) and THF (360 mL) was added dropwise via an addition funnel to the ice bath cooled NaOCl (4%, 3.5 L) solution over a period of 15 minutes. Solid n-Bu$_4$NI (13.1 g, 35.6 mmol) was added and the reaction mixture was stirred for 1.5 h. The two layers were separated, the aqueous layer was extracted with diisopropylether and the combined organic layer was washed with water and brine, dried over Na$_2$SO$_4$, and the solvent was removed under reduced pressure. The residue was dissolved in methanol (165 mL), KOH (39.8 g, 300 mmol) was added, and the mixture was refluxed for 1 h. The solvent was evaporated under reduced pressure and the crude product was purified by column chromatography to yield compound 1-(1-phenyltricyclo[3.3.1.0$^{3,7}$]non-3-yl)ethanone (50.0 g) in 59% yield as viscous liquid. m/z (M+1) 241; IR (cm$^{-1}$): 2924, 2867, 1697, 1445, 1356, 1223, 757, 699. $^1$H NMR (CDCl$_3$) 300 MHz δ 7.38-7.19 (m, 5H), 2.86-2.80 (m, 1H), 2.59-2.50 (m, 1H), 2.32-2.25 (m, 1H), 2.23 (s, 3H), 2.10-1.99 (m, 4H), 1.90-1.79 (m, 4H), 1.78-1.71 (m, 1H). $^{13}$C NMR (CDCl$_3$) 75 MHz δ, 211.7, 146.7, 128.2 (2C), 125.7 (2C), 124.7, 61.9, 50.2, 49.0, 47.9, 45.7, 42.4, 42.3, 37.6, 26.4.

Preparation 2

[3-(2-Methyl-1,3-dioxolan-2-yl)tricyclo[3.3.1.0$^{3,7}$]non-1-yl]methyl methanesulfonate

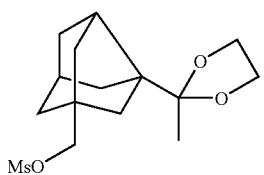

Step I: To a stirred mixture of 1-(1-Phenyltricyclo[3.3.1.0$^{3,7}$]non-3-yl)ethanone (8.0 g, 33.3 mmol) as obtained in preparation 1, carbontetrachloride (66 mL), acetonitrile (66 mL) and water (100 mL), cooled to 0° C., was added sodiumperiodate (31.9 g, 149 mmol) and ruthenium (III) chloride hydrate (0.44 g, 1.7 mmol). The reaction mixture was gradually warmed to ambient temperature and stirred for 2 h. The reaction mixture was diluted with diisopropylether (100 mL) and stirred for 15 minutes to precipitate black RuO$_2$. The reaction mixture was then filtered through a pad of celite and the organic layer was extracted with 1N NaOH solution (3×25 mL). The organic layer was dried over Na$_2$SO$_4$ and the solvent was evaporated under vacuum to obtain unreacted starting material (3.04 g 12.67 mmol). The aqueous layer was acidified with conc. HCl and extracted with EtOAc. The combined organic layers were washed with brine, dried over Na$_2$SO$_4$, and the solvent was removed under reduced pressure to obtain 3-acetyltricyclo[3.3.1.0$^{3,7}$]nonane-1-carboxylic acid (4.0 g) as off-white solid in 57% yield. M.R: 90-95.0° C. m/z (M+1) 209. IR cm$^{-1}$ 2935, 1694, 1413, 1357, 974, 746. $^1$H NMR (CDCl$_3$) 300 MHz δ 2.77-2.73 (m, 1H), 2.54-2.48 (m, 1H), 2.44-2.34 (m, 1H), 2.20 (s, 3H), 2.18-2.09 (m, 1H), 7.38-7.19 (m, 5H), 2.86-2.80 (m, 1H), 2.59-2.50 (m, 1H), 2.32-2.25 (m, 1H), 2.23 (s, 3H), 2.18-2.09 (m, 1H), 2.06-1.74 (m, 7H), 1.73-1.61 (m, 1H). $^{13}$C NMR (CDCl$_3$) 75 MHz δ 211.0, 181.3, 61.5, 50.3, 47.9, 45.9, 45.6, 42.6, 41.9, 36.8, 35.6, 26.4.

Step II: To 3-acetyltricyclo[3.3.1.0$^{3,7}$]nonane-1-carboxylic acid (2.4 g, 11.4 mmol) obtained in step I, in MeOH (48 mL) cooled to ice bath temperature, was added acetyl chloride (1.64 mL, 22.8 mmol). The reaction mixture was gradually warmed to room temperature and stirred for 2 h. The volatiles were removed under reduced pressure and the crude product was purified by column chromatography to obtain methyl 3-acetyltricyclo[3.3.1.0$^{3,7}$]nonane-1-carboxylate (2.4 g) in 93% yield as viscous liquid. m/z (M+1) 223. IR cm$^{-1}$ 2953, 1728, 1698, 1461, 1234, 1078, 755. $^1$H NMR (CDCl$_3$) 300 MHz δ 3.66 (s, 3H), 2.75-2.70 (m, 1H), 2.53-2.46 (m, 1H), 2.40-2.32 (m, 1H), 2.19 (s, 3H), 2.15-2.05 (m, 1H), 2.03-1.60 (m, 8H). $^{13}$C NMR (CDCl$_3$) 75 MHz δ 210.9, 175.3, 61.4, 53.4, 51.6, 50.5, 48.0, 45.9, 45.6, 42.6, 41.9, 36.8, 35.9, 26.4.

Step III: A mixture of methyl 3-acetyltricyclo[3.3.1.0$^{3,7}$]nonane-1-carboxylate (2.0 g, 8.9 mmol) obtained in step II, 1,2-ethanediol (8.9 mL), p-TSA (47 mg, 5 mol %) and benzene (36 mL) was refluxed using a Dean-Stark apparatus for 1 h. The reaction mixture was cooled to room temperature, 10% aq. NaHCO$_3$ (36 mL) was added, and the two layers were separated. The aqueous layer was extracted with EtOAc. The combined organic layers were washed with brine, dried over Na$_2$SO$_4$, and the solvent was evaporated under reduced pressure to obtain methyl 3-(2-methyl-1,3-dioxolan-2-yl)tricyclo[3.3.1.0$^{3,7}$]nonane-1-carboxylate (2.2 g) in 93% yield as viscous liquid. m/z (M+1) 267. IR cm$^{-1}$ 2954, 1731, 1698, 1460, 1236, 1046, 752. $^1$H NMR (CDCl$_3$) 300 MHz δ 4.07-3.94 (m, 4H), 3.66 (s 3-H), 2.44-2.36 (m 2-H), 2.27-2.18 (m, 1H), 2.12-2.02 (m, 1H), 1.94-1.81 (m, 8-H), 1.30 (s, 3H).

Step IV: Methyl 3-(2-methyl-1,3-dioxolan-2-yl)tricyclo[3.3.1.0$^{3,7}$]nonane-1-carboxylate (2.3 g, 8.64 mmol) obtained in step III, in THF (15 mL) was added slowly under N$_2$ atmosphere through a dropping funnel to a suspension of LiAlH$_4$ (0.32 g, 8.64 mmol) in ether (15 mL) at ice bath temperature. The reaction mixture was stirred for 30 minutes before being quenched by addition of sat. aq. NH$_4$Cl solution (9 mL), followed by 1N NaOH solution (9 mL) and the reaction mixture was stirred at room temperature for 15 minutes before it was filtered through a pad of celite. The organic layer was washed with brine, dried over Na$_2$SO$_4$ and the solvent was evaporated under reduced pressure to obtain [3-(2-Methyl-1,3-dioxolan-2-yl)tricyclo[3.3.1.0$^{3,7}$]non-1-yl]methanol (1.9 g) in 94% yield as viscous liquid. m/z (M+1) 269; IR cm$^{-1}$ 3436, 2936, 1634, 1459, 1373, 1309, 1047, 757. $^1$H NMR (CDCl$_3$) 300 MHz δ 4.15-3.80 (m, 4H), 3.53 (s 3H), 2.50-2.30 (m 2H), 1.90-1.30 (m, 10H), 1.29 (s, 3H).

Step V: To a solution of [3-(2-Methyl-1,3-dioxolan-2-yl)tricyclo[3.3.1.0$^{3,7}$]non-1-yl]methanol (2.0 g, 8.47 mmol)

obtained in step IV, in THF (35 mL) at ice bath temperature, was sequentially added triethylamine (3.5 mL, 25.4 mmol), DMAP (52 mg, 0.42 mmol), and methanesulfonyl chloride (0.97 mL, 12.7 mmol). After stirring the reaction mixture at the same temperature for 0.5 h, it was diluted with water and extracted with EtOAc. The combined organic layers were washed with brine, dried over $Na_2SO_4$ and the solvent was removed under reduced pressure. The crude product was purified by column chromatography to obtain title compound [3-(2-Methyl-1,3-dioxolan-2-yl) tricyclo[3.3.1.0$^{3,7}$]non-1-yl]methyl methane sulfonate (2.4 g) in 90% yield as viscous liquid. m/z (M+1) 317. IR cm$^{-1}$ 2954, 1461, 1356, 1216, 1174, 1048, 756. $^1$H NMR (CDCl$_3$) 300 MHz δ 4.15-3.90 (m, 4H), 3.00 (s 3H), 2.44-2.36 (m 2H), 1.89-1.79 (m, 2H), 1.78-1.42 (m, 8H), 1.29 (s, 3H). $^{13}$C NMR (CDCl$_3$) 75 MHz δ 112.1, 76.3, 64.95, 64.9, 57.3, 46.6, 45.3, 44.9, 44.5, 42.9, 39.8, 36.9, 36.7, 36.3, 20.

Preparation 3

{3-[(tert-butoxy carbonyl)amino]tricyclo[3.3.1.0$^{3,7}$]non-1-yl}methyl methanesulfonate

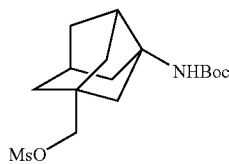

Step I: To a suspension of NaH (60% dispersed in nujol, 3.36 g, 21 mmol) in THF (84 mL) cooled to ice bath temperature was added a solution of [3-(2-Methyl-1,3-dioxolan-2-yl)tricycle[3.3.1.0$^{3,7}$]non-1-yl]methanol (10.0 g, 42.0 mmol) (as obtained in preparation 2 step IV) in THF (84 mL) via a syringe over a period of 30 minutes. After stirring the reaction mixture for 30 minutes at room temperature, nBu$_4$NI (0.37 g, 1.0 mmol) was sequentially added; followed by benzylbromide (5.0 mL, 42.0 mmol). The reaction mixture was warmed to room temperature and stirred for 16 h until TLC revealed completion of the reaction. After cooling the reaction mixture to ice bath temperature, excess NaH was quenched by adding sat. aq NH$_4$Cl solution. The two layers were separated and the aqueous layer was extracted with EtOAc. The combined organic layers were washed with brine, dried over anhydrous Na$_2$SO$_4$, and the solvent was evaporated under reduced pressure to obtain a crude reaction mass, which was purified by column chromatography to yield 2-[1-(benzyloxymethyl)tricyclo[3.3.1.0$^{3,7}$]non-3-yl]-2-methyl-1,3-dioxolane (11.0 g) as viscous liquid in 80% yield. m/z (M+1) 329; $^1$H NMR (CDCl$_3$) 300 MHz δ 7.38-7.22 (m, 5H), 4.50 (s, 2H), 4.02-3.92 (m, 4H), 3.24 (s, 2H), 2.38-2.30 (m, 2H), 1.88-1.71 (m, 2H), 1.70-1.60 (m, 4H), 1.55-1.39 (m, 4H), 1.27 (s, 3H).

Step II: A mixture of 2-[1-(benzyloxymethyl)tricyclo[3.3.1.0$^{3,7}$]non-3-yl]-2-methyl-1,3-dioxolane (2.6 g, 7.9 mmol), p-toluenesulfonic acid (0.3 g, 1.6 mmol), and acetone (31.6 mL) was refluxed for 4 h. The volatiles were removed under vacuum and the residue was diluted with EtOAc, washed with 10% aq. NaHCO$_3$ and brine, dried over Na$_2$SO$_4$, and the solvent was evaporated under reduced pressure to obtain 1-{1-[(benzyloxy)methyl]tricyclo[3.3.1.0$^{3,7}$]non-3-yl}ethanone (2.1 g) as a viscous liquid in 93% yield. m/z (M+1) 285; $^1$H NMR (CDCl$_3$) 300 MHz δ 7.40-7.22 (m, 5H), 4.50 (s, 2H), 3.27 (s, 2H), 2.70-2.62 (m, 1H), 2.47-2.40 (m, 1H), 2.16 (s, 2H), 2.0-1.90 (m, 2H), 1.81-1.56 (m, 7H), 1.50 (dd, J=3.0, 11.0 Hz, 1H).

Step III: To a mixture of NaOH (30.6 g, 765 mmol), H$_2$O (255 mL) and 1,4 dioxane (51 mL) at ice bath temperature was added Br$_2$ (15.2 mL, 285.6 mmol) and stirred for 15 minutes. This hypobromite solution was added dropwise to a stirred solution of 1-{1-[(benzyloxy)methyl]tricyclo[3.3.1.0$^{3,7}$]non-3-yl}ethanone (14.5 g, 51.0 mmol) in 1,4-dioxane (51 mL) at ice bath temperature. The reaction mixture was gradually warmed to r.t. and stirred for 1 h. The reaction mixture was cooled to ice bath temperature and quenched by adding AcOH (46.7 mL, 765 mmol). The reaction mixture was diluted with water, extracted with EtOAc, the combined organic layers were washed with brine, dried over Na$_2$SO$_4$, and the solvent was removed under reduced pressure to obtain 1-[(benzyloxy)methyl]tricyclo[3.3.1.0$^{3,7}$]nonane-3-carboxylic acid (8.0 g) as white solid in 55% yield. m/z (M−1), 285; $^1$H NMR (CDCl$_3$) 300 MHz δ 7.40-7.22 (m, 5H), 4.50 (s, 2H), 3.27 (s, 2H), 2.70-2.62 (m, 1H), 3.47-3.38 (m, 1H), 2.16 (s, 2H), 2.12-1.98 (m, 2H), 1.90-1.55 (m, 7H), 1.50 (dd, J=3.0, 11.0 Hz, 1H).

Step IV: To a stirred mixture of 1-[(benzyloxy)methyl]tricyclo[3.3.1.0$^{3,7}$]nonane-3-carboxylic acid (1.8 g, 6.3 mmol) obtained in step III, triethylamine (2.6 mL, 18.9 mmol) and toluene (25 mL) at ice bath temperature was added diphenylphosphoryl azide (1.5 mL, 6.93 mmol). The reaction mixture was warmed to r.t, stirred for one hour, and then refluxed for 4 h. Upon completion of the reaction, the reaction mixture was transferred to a separatory funnel and washed with water. The organic layer was stirred with aq. KOH solution (50% w/v, 12.6 mL), and nBu$_4$NI (120 mg, 0.32 mmol) for 2 h. The reaction mixture was cooled to ice bath temperature, acidified with 2N KHSO$_4$ to pH 2, extracted with ether, the aqueous layer was basified with aq. NaOH solution (50% w/v) and extracted with chloroform. The combined organic layers were dried over anhydrous Na$_2$SO$_4$ and the solvent was evaporated under reduced pressure to obtain 1-[(benzyloxy)methyl]tricyclo[3.3.1.0$^{3,7}$]nonan-3-amine (0.82 g) as viscous liquid in 51% yield. m/z (M+1) 258; $^1$H NMR (CDCl$_3$) 300 MHz δ 7.37-7.24 (m, 5H), 4.50 (s, 2H), 3.24 (s, 2H), 2.37-2.29 (m, 1H), 2.0-1.81 (m, 3H), 1.78-1.70 (m, 1H), 1.70-1.45 (m, 7H), 1.40 (dd, J=2.9, 10.7 Hz, 1H).

Step V: To a stirred solution of 1-[(benzyloxy)methyl]tricyclo[3.3.1.0$^{3,7}$]nonan-3-amine (0.82 g, 3.2 mmol) obtained in step IV in dichloromethane (13 mL) at ice bath temperature was added Et$_3$N (0.67 mL, 4.8 mmol) and ditertiary butyldicarbonate (0.77 g, 3.5 mmol). After stirring the reaction mixture at room temperature for 1 h, the volatiles were removed under reduced pressure and the crude product was purified by column chromatography to obtain tert-butyl [1-(benzyloxy methyl)tricyclo[3.3.1.0$^{3,7}$]non-3-yl]carbamate as a viscous liquid (1.0 g) in 88% yield. m/z (M+1) 358; $^1$H NMR (CDCl$_3$) 300 MHz δ 7.37-7.24 (m, 5H), 4.49 (s, 2H), 3.25 (s, 2H), 2.48-2.38 (m, 1H), 2.37-2.30 (m, 1H), 2.10-1.87 (m, 2H), 1.82-1.67 (m, 2H), 1.67-1.39 (m, 6H), 1.44 (s, 9H).

Step VI: To a stirred mixture of tert-butyl [1-(benzyloxymethyl)tricyclo[3.3.1.0$^{3,7}$]non-3-yl]carbamate (1.0 g, 2.8 mmol) obtained in step V in MeOH (11 mL), Pd/C (10%, 0.2 g) was added. The H$_2$ pressure was then applied with the balloon for 2 h. The reaction mixture was filtered through a pad of celite and the filtrate was concentrated under reduced pressure to obtain tert-butyl [1-(hydroxymethyl)tricyclo[3.3.1.0$^{3,7}$]non-3-yl]carbamate as a viscous liquid (0.7 g) in 95% yield. m/z (M+1) 268; $^1$H NMR (CDCl$_3$) 300 MHz δ 4.74 (s (br), 1H), 3.45 (s, 2H), 2.50-2.40 (m, 1H), 2.40-2.33 (m, 1H), 2.05-1.87 (m, 4H), 1.80 (dd, J=2.4, 10.3 Hz, 1H), 1.65 (dd, J=3.0, 10.0 Hz, 1H), 1.54-1.40 (m, 3H), 1.45 (s, 9H), 1.37 (dd, J=3.1, 10.0 Hz, 1H).

Step VII: To a stirred solution of tert-butyl [1-(hydroxymethyl)tricyclo[3.3.1.0$^{3,7}$]non-3-yl]carbamate (0.65 g, 2.45 mmol) obtained in step VI in THF (10 mL) at ice bath temperature, was sequentially added Et$_3$N (1.0 mL, 7.35 mmol), DMAP (20 mg, 0.16 mmol), and methanesulfonyl chloride (0.29 mL, 3.7 mmol). After stirring the reaction at the same temperature for 0.5 h, it was diluted with water and extracted with EtOAc. The combined organic layers were washed with brine, dried over Na$_2$SO$_4$, and the solvent was removed under reduced pressure. The crude product was purified by column chromatography to obtain title compound {3-[(tert-butoxycarbonyl)amino]tricyclo[3.3.1.0$^{3,7}$]non-1-yl}methyl methane sulfonate as a viscous liquid (0.84 g) in 100% yield. m/z (M+1) 358; $^1$H NMR (CDCl$_3$) 300 MHz δ 4.76 (s (br), 1H), 4.02 (s, 2H), 3.01 (s, 2H), 2.99 (s, 3H), 2.54-2.44 (m, 1H), 2.42-2.35 (m, 1H), 2.20-1.87 (m, 4H), 1.82 (dd, J=2.2, 10.5 Hz, 1H), 1.76-1.58 (m, 4H), 1.57-1.48 (m, 1H), 1.45 (s, 9H).

Preparation 4

Benzyl[2-(4-aminophenyl)hexahydro-2,5-methanopentalene-3a(1H)-yl]carbamate

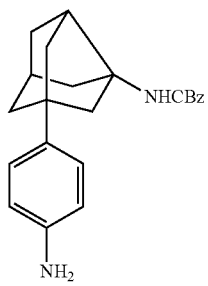

Step I: Nitration mixture (1 mL) [the nitration mixture was prepared by mixing of 10.5 g of nitric acid (d 1.375 at 22° C.), 180.0 g of conc. sulphuric acid (d 1.84 at 22° C.), and 16 g of H$_2$O) was added drop wise to a stirred solution of 1-(1-phenyltricyclo[3.3.1.0$^{3,7}$]non-3-yl)ethanone (240 mg, 1.0 mmol) obtained in preparation 1, in nitromethane (4 mL) at 0° C. After stirring for 2 h, the reaction mixture was poured into ice cold water and extracted with EtOAc, the combined organic layers were washed with brine and dried over Na$_2$SO$_4$. The solvent was evaporated under reduced pressure and the crude product was purified by column chromatography to obtain 1-[1-(4-nitrophenyl)tricyclo[3.3.1.0$^{3,7}$]non-3-yl]ethanone as an off-white solid (250 mg) in 88% yield. M.R: 61.3-66.6° C. m/z (M+1) 286; IR cm$^{-1}$ 2953, 1697, 1598, 1519, 1217, 1110, 852, 768. $^1$H NMR (CDCl$_3$) 300 MHz δ 8.17 (d, J=8.7 Hz, 2H), 7.43 (d, J=8.7 Hz, 2H), 2.87-2.80 (m, 1H), 2.61-2.55 (m, 1H), 2.34-2.26 (m, 1H), 2.23 (s, 3H), 2.13-1.98 (m, 4H), 1.90-1.71 (m, 5H).

Step II: To a stirred solution of NaOH (6.3 g, 158.0 mmol), H$_2$O (54.0 mL) and 1,4 dioxane (7 mL) at ice bath temperature was added Br$_2$ (3.2 mL, 59.0 mmol) and stirred for 5 minutes. The formed hypobromite solution was added dropwise to a stirred solution of 1-[1-(4-nitrophenyl)tricyclo[3.3.1.0$^{3,7}$]non-3-yl]ethanone (3.0 g, 10.53 mmol) obtained in step I, in 1,4-dioxane (14 mL) at ice bath temperature. The reaction mixture was gradually warmed to r.t. and after 1 h, it was cooled to ice bath temperature and acidified with conc. HCl, diluted with water, and extracted with EtOAc. The combined organic layer was washed with brine, dried over Na$_2$SO$_4$, and the solvent was removed under reduced pressure to obtain 1-(4-nitrophenyl)tricyclo[3.3.1.0$^{3,7}$]nonane-3-carboxylic acid (2.27 g) in 75% yield as off-white solid; M.R: 145-150° C. m/z (M−1) 286; IR cm$^{-1}$ 3437, 2945, 1693, 1596, 1511, 1408, 1352, 946, 839, 749. $^1$H NMR (CDCl$_3$) 300 MHz δ 8.16 (d, J=8.8 Hz, 2H), 7.42 (d, J=8.8 Hz, 2H), 2.96-2.88 (m, 1H), 2.59-2.52 (m, 1H), 2.44-2.33 (m, 1H), 2.23-2.03 (m, 4H), 2.02-1.68 (m, 5H).

Step III: To the stirred solution of 1-(4-nitrophenyl)tricyclo[3.3.1.0$^{3,7}$]nonane-3-carboxylic acid (3.0 g, 10.45 mmol) obtained in step II, in CHCl$_3$ (21 mL) was added conc. H$_2$SO$_4$ (4.2 mL, 78.9 mmol) then solid NaN$_3$ was added in portions, so that the temperature of the reaction did not rise above 40° C. The reaction mixture was warmed to 45° C. and after stirring for 2 h it was cooled again to ice bath temperature, diluted with water and extracted with EtOAc. The aqueous layer was basified with 50% NaOH solution and extracted with CHCl$_3$. The combined organic layer was washed with brine, dried over Na$_2$SO$_4$, and the solvent was removed under reduced pressure to obtain 1-(4-nitrophenyl)tricyclo[3.3.1.0$^{3,7}$]nonan-3-amine as an off-white solid (2.0 g) in 74% yield. M.R: 201.0-205.9° C. m/z (M+1) 259; IR cm$^{-1}$ 3435, 2941, 1643, 1596, 1518, 1400, 1349, 1013, 750. $^1$H NMR (CDCl$_3$) 300 MHz δ 8.14 (d, J=8.8 Hz, 2H), 7.39 (d, J=8.8 Hz, 2H), 3.70-3.60 (d (br), 2H), 2.62-2.50 (m, 2H), 2.38-2.23 (m, 3H), 2.15-2.0 (m, 3H), 1.95-1.60 (m, 4H).

Step IV: To a stirred mixture of 1-(4-nitrophenyl)tricyclo[3.3.1.0$^{3,7}$]nonan-3-amine (2.0 g, 8.0 mmol) obtained in step III, K$_2$CO$_3$ (3.5 g, 24 mmol) in THF (80 mL), cooled to ice-bath temperature was added benzylchloroformate (50% w/v in Toluene, 2.2 mL, 12 mmol). After stirring the reaction mixture at r.t for 2 h, it was diluted with water and extracted with EtOAc. The combined organic layers were washed with brine, dried over Na$_2$SO$_4$, and the solvent was removed under reduced pressure to obtain benzyl[2-(4-nitrophenyl)hexahydro-2,5-methanopentalen-3a(1H)-yl]carbamate as an off-white solid (2.1 g) in 70% yield. M.R: 104.1-105.9° C.; m/z (M+1) 393; IR cm$^{-1}$ 3440, 2952, 1714, 1518, 1349, 1216, 757; $^1$H NMR (CDCl$_3$) 300 MHz δ 8.12 (d, J=8.8 Hz, 2H), 7.50-7.27 (m, 7H), 5.20-5.0 (s (br), 2H), 2.65-2.55 (m, 1H), 2.50-1.55 (m, 11H). $^{13}$C NMR (CDCl$_3$) 75 MHz δ 155.1, 154.2, 146.1, 136.4, 131.1, 128.5 (2C), 128.1 (2C), 126.6 (2C), 123.4 (2C), 66.3, 64.4, 49.2 48.0, 47.5, 43.8, 42.1, 40.8, 37.0.

Step V: To a stirred solution of benzyl[2-(4-nitrophenyl)hexahydro-2,5-methanopentalen-3a(1H)-yl]carbamate (1.0 g, 2.55 mmol) as obtained in step IV in a 1:2:4 mixture of water, THF, and ethanol respectively (10 mL) was added solid NH$_4$Cl (0.5 g, 9.3 mmol) and Fe powder (0.5 g, 9.0 mmol). The reaction mixture was heated to reflux for 2 h. The reaction mixture was cooled to room temperature and filtered through a small pad of celite. The filtrate was evaporated under reduced pressure and the residue was diluted with water and extracted with EtOAc. The combined organic layer was washed with brine, dried over anhydrous Na$_2$SO$_4$ and the solvent was evaporated under reduced pressure to obtain benzyl[2-(4-aminophenyl) hexahydro-2,5-methanopentalene-3a (1H)-yl]carbamate as off-white solid (0.75 g) in 81% yield. m/z (M+1) 363; IR cm$^{-1}$ 3441, 2950, 1715, 1517, 1346, 1216, 756. $^1$H NMR (CDCl$_3$) 300 MHz δ 7.45-7.05 (m, 9H), 5.20-5.0 (s (br), 2H), 2.65-2.50 (m, 1H), 2.50-2.40 (m, 1H), 2.36-1.57 (m, 10H).

Preparation 5

(2S,4S)-1-(chloroacetyl)-4-fluoropyrrolidine-2-carbonitrile

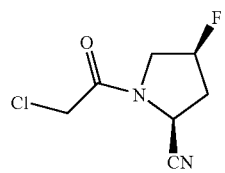

Step I: To a stirred solution of (2S,4R)-4-hydroxypyrrolidine-2-carboxylic acid (13.1 g, 0.1 mol) in methanol (400 mL) cooled to 0° C. was added acetyl chloride (14.3 mL, 0.2 mol) over a period of 30 min. The reaction mixture was warmed to room temperature and stirred for 2 h. The volatiles were removed under reduced pressure and the residue was triturated with ether several times to get methyl (2S,4R)-4-hydroxypyrrolidine-2-carboxylate hydrochloride salt as a white powder (14.5 g) in 100% yield. m/z (M+1) 145; $^1$H NMR (DMSO-d$_6$) 300 MHz δ 5.7-5.5 (s (br), 1H), 4.55-4.35 (m, 2H), 3.76 (s, 3H), 3.35 (d, J=12 Hz 1H), 3.10 (d, J=12 Hz 1H), 2.25-2.0 (m, 2H).

Step II: To a stirred suspension of the hydrochloride salt obtained in step I (14.5 g, 0.1 mol) in CH$_2$Cl$_2$ (400 mL) cooled to 0° C. was added Et$_3$N (28 mL, 0.2 mol), DMAP (0.61 g, 5 mmol), and Boc anhydride (27.5 mL, 0.12 mol). The reaction mixture was gradually warmed to room temperature and stirred for 2 h. The solvent was then removed under vacuum and ether was added to the residual solid. The solid was filtered through a sintered funnel and washed thoroughly with ether. The filtrate was evaporated under reduced pressure. The residue was dissolved in CH$_2$Cl$_2$ and washed with sat. NaCl and sat. NaHCO$_3$ followed by drying over anhydrous Na$_2$SO$_4$. The solvent was evaporated under reduced pressure to obtain light yellow oil which solidified under high vacuum. The resulting solid was triturated several times with hexanes. The solid was dried under high vacuum yielding 1-tert-butyl 2-methyl (2S,4R)-4-hydroxypyrrolidine-1,2-dicarboxylate as a white solid (24.5 g) in 100% yield. (M+1) 245; $^1$H NMR (CDCl$_3$) 300 MHz δ 4.54-4.37 (m, 2H), 3.75 (s, 3H), 3.70-3.40 (m, 2H), 2.48-2.21 (m, 2H), 2.13-2.0 (m, 1H), 1.46 (s, 3H), 1.41 (s, 6H).

Step III: To a stirred solution of compound obtained in step II (24.5 g, 0.1 mol) in 1,2-dichloroethane (300 mL) cooled to −10° C. was added diethylaminosulfur trifluoride (19.7 mL, 0.15 mol) over a period of 30 minutes. The reaction mixture was stirred at this temperature for 1 h then at room temperature for 16 h. The reaction mixture was quenched by adding mixture of crushed ice (300 g) and solid NaHCO$_3$ (25.2 g, 0.3 mol). The two layers were separated and the aqueous layer was extracted with dichloromethane. The combined organic layer was washed with brine, dried over anhydrous Na$_2$SO$_4$, and the solvent was removed under reduced pressure to obtain 1-tert-butyl 2-methyl (2S,4S)-4-fluoropyrrolidine-1,2-dicarboxylate as a viscous liquid (24.7 g) in 100% yield. [α]$_D$ −53.3, (c, 1.0, CHCl$_3$). m/z (M+1) 248; $^1$H NMR (CDCl$_3$) 300 MHz δ 5.20 (ddd, J=3.8, 3.8, 49.1 Hz, 1H), 4.55 (d, J=9.5 Hz, ½H), 4.42 (d, J=8.9 Hz, ½H), 3.90-3.55 (m, 2H), 3.75 (s, 3H), 2.55-2.20 (m, 2H), 1.46 (s, 3H), 1.41 (s, 6H).

Step IV: To the stirred solution of 1-tert-butyl-2-methyl (2S,4S)-4-fluoropyrrolidine-1,2-dicarboxylate (24.7 g, 0.1 mol) obtained in step III in THF (200 mL) cooled to 0° C. was added a solution of LiOH (3.6 g, 0.15 mol) in water (200 mL) over a period of 30 min. The reaction mixture was warmed to room temperature and stirred for 12 h until the TLC reveals completion of the reaction. The reaction mixture was diluted with water, ether, and two layers were separated. The aqueous layer was acidified with conc. HCl and extracted with EtOAc. The combined organic layer was washed with water and brine, dried over anhydrous Na$_2$SO$_4$, and the solvent was evaporated under reduced pressure to obtain (2S,4S)-1-(tert-butoxycarbonyl)-4-fluoropyrrolidine-2-carboxylic acid as an off white solid (21 g) in 90% yield. [α]$_D$, −65.7 (c, 1.0, CHCl$_3$); m/z (M−1) 232; $^1$H NMR (CDCl$_3$) 300 MHz δ 5.22 (ddd, J=3.8, 3.8, 52.3 Hz, 1H), 4.60-4.40 (m, 1H), 3.95-3.50 (m, 2H), 2.78-2.15 (m, 2H), 1.6-1.35 (m, 9H).

Step V: To a stirred solution of acid obtained in step IV (17.3 g, 0.074 mol) in acetonitrile (220 mL) at room temperature was added pyridine (6.6 mL, 0.082 mol), Boc anhydride (20 mL, 0.089 mol). After 1 h, solid NH$_4$HCO$_3$ (9.4 g, 0.12 mol) was added and the reaction mixture was stirred for 12 h. The reaction mixture was diluted with EtOAc and washed with a mixture (1:1 by v/v) of brine and 1N HCl. The organic layer was dried over anhydrous Na$_2$SO$_4$ and the solvent was removed under vacuum to obtain tert-butyl (2S,4S)-2-(aminocarbonyl)-4-fluoropyrrolidine-1-carboxylate (17 g) as a viscous liquid. The product was used for the next reaction without further purification. m/z (M+1) 233; $^1$H NMR (CDCl$_3$) 300 MHz δ 6.70-6.60 (s (br), ½H), 6.30-6.10 (s (br), ½H), 5.50-5.40 (s (br), 1H), 5.22 (ddd, J=3.4, 3.4, 52.0 Hz, 1H), 4.50-4.30 (m, 1H), 3.95-3.50 (m, 2H), 2.90-2.10 (m, 2H), 1.48 (s, 9H).

Step VI: To a stirred solution of the amide obtained in the previous step (17.9 g, 0.077 mol) in EtOAc (35 mL) at 0° C. was added dry HCl in EtOAc (4 N, 225 mL) over a period of 30 min. After stirring at 0° C. for 1 h the volatiles were removed under reduced pressure and the residue was triturated with ether several times to obtain (2S,4S)-4-fluoro pyrrolidine-2-carboxamide, hydrochloride salt as an off-white powder (12 g) in 92% yield. m/z (M+1) 133; $^1$H NMR (DMSO-d$_6$) 300 MHz δ 10.60-10.30 (s (br), ½H), 8.90-8.60 (s (br), ½H), 8.10 (s (br), 1H), 7.72 (s (br), 1H), 5.38 (ddd, J=3.7, 3.7, 52.4 Hz, 1H), 4.32 (d, J=10.5 Hz 1H), 4.28 (d, J=10.4 Hz 1H), 3.64-3.29 (m, 2H), 2.73-2.50 (m, 1H), 2.41-2.24 (m, 1H).

Step VII: To a stirred suspension of hydrochloride salt as obtained in step VI (12 g, 0.071 mol) in dichloromethane (140 mL) cooled to 0° C. was added Et$_3$N (30 mL, 0.213 mol), chloroacetyl chloride (8.1 mL, 0.107 mol). The reaction mixture was gradually warmed to r.t. and stirred for 1 h. The reaction mass was filtered through a sintered funnel, washed the salt bed with ether and the filtrate was evaporated under vacuum to obtain a crude product (2S,4S)-1-(chloroacetyl)-4-fluoropyrrolidine-2-carboxamide (14.8 g) as a viscous liquid in 3:1 mixture of rotomers. m/z (M+1) 209; $^1$H NMR (DMSO-d$_6$) 300 MHz δ 7.26 (s (br), ½H), 7.04 (s (br), ½H), 5.34 (d, J=52.5 Hz, 0.8H), 5.25 (d, J=53.0 Hz, 0.2H), 4.58-4.30 (m, 3H), 3.90-3.50 (m, 2H), 2.60-2.20 (m, 2H).

Step VIII: To a stirred solution of the compound obtained in step VII (14.7 g, 0.07 mol) in dry THF (140 mL) under N$_2$ atmosphere at 0° C. was added trifluoroacetic anhydride (15 mL, 0.107 mol). The reaction mixture was gradually warmed to r.t. and stirred for 1 h. Water was added and the two layers were separated. The aqueous layer was extracted with EtOAc and the combined organic layer was washed with brine, dried over anhydrous $Na_2SO_4$. The solvent was evaporated under reduced pressure to obtain crude product, which was purified by column chromatography to yield (2S,4S)-1-(chloroacetyl)-4-fluoropyrrolidine-2-carbonitrile as a tan solid (8.7 g) in 64% yield (3:1 mixture of two rotomers). $[\alpha]_D$, −51.0 (c, 1.0, $CHCl_3$); IR $cm^{-1}$ 3031, 3007, 2962, 2241, 1679, 1407, 1280, 12225, 1076, 860; m/z (M+1), 191; $^1H$ NMR ($CDCl_3$) 300 MHz δ 5.45 (ddd, J=3.4, 3.4, 51.3 Hz, 0.8H), 5.37 (ddd, J=3.4, 3.4, 51.0 Hz, 0.2H), 5.06 (d, J=8.9 Hz, 0.2H), 4.95 (d, 9.3 Hz, 0.8H), 4.30-3.55 (m, 2H), 4.06 (s, 2H), 2.65-2.55 (m, 1H), 2.50-2.25 (m, 1H).

Preparation 6

(2S,4R)-1-(2-chloroacetyl)-4-fluoropyrrolidine-2-carbonitrile

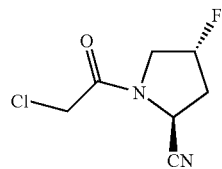

The compound (2S,4R)-1-(2-chloroacetyl)-4-fluoropyrrolidine-2-carbonitrile is synthesized from (2S,4S)-4-hydroxypyrrolidine-2-carboxylic acid using the same sequence of steps and procedures as outlined above for (2S,4S)-1-(2-chloroacetyl)-4-fluoropyrrolidine-2-carbonitrile starting from (2S,4R)-4-hydroxypyrrolidine-2-carboxylic acid. (2S,4R)-1-(2-chloroacetyl)-4-fluoropyrrolidine-2-carbonitrile: Solid, 4:1 mixture of two rotomers; m/z (M+1) 191; $^1H$ NMR ($CDCl_3$) 300 MHz δ 5.38 (d (br), J=51.3 Hz, 0.8H), 5.33 (d (t), J=51.0 Hz, 0.2H), 5.02 (d, J=8.5 Hz, 0.2H), 4.72 (d, 8.5 Hz, 0.8H), 4.40-3.30 (m, 2H), 4.06 (s, 2H), 3.0-2.65 (m, 1H), 2.62-2.40 (m, 1H).

Preparation 7

(4R)-3-(chloroacetyl)-1,3-thiazolidine-4-carbonitrile

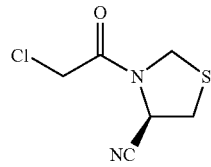

Step I: To a stirred solution of 40% aq. formaldehyde (40 mL) at 0° C. was added in portions solid L-cystein (12.1 g, 0.1 mol) over a period of 30 minutes. The reaction mixture was stirred for 4 h, after which the reaction mixture was filtered through a sintered funnel. The solids were washed with absolute ethanol then with diethyl ether. The solids were dried under high vacuum to obtain (4R)-1,3-thiazolidine-4-carboxylic acid (12.5 g) in 94% yield. M.R, 215-217° C.; m/z (M+1) 134; IR $cm^{-1}$ 3429, 3049, 2357, 1629, 1463, 1383, 1343, 1014, 862; $^1H$ NMR ($D_2O$) 300 MHz δ 4.40-4.30 (m, 2H), 4.30-4.22 (m, 1H), 3.40-3.18 (m, 2H).

Step II: To a stirred mixture of the compound obtained in step I (13.3 g, 0.1 mol) in acetonitrile (400 mL) cooled to 0° C., was added pyridine (20.1 mL, 0.22 mol) and Boc-anhydride (58 mL, 0.24 mol). After stirring the reaction mixture for 1 h at room temperature, solid $NH_4HCO_3$ (11.8 g, 0.15 mol) was added and the reaction mixture was stirred for another 2 h. The reaction mixture was partitioned between ethylacetate and 1:1 mixture of 2N HCl and brine solution. The aqueous layer was extracted with ethylacetate, the combined organic layers were dried over anhydrous $Na_2SO_4$, and the solvent was evaporated under reduced pressure to obtain tert-butyl (4R)-4-(aminocarbonyl)-1,3-thiazolidine-3-carboxylate (23 g) as a gummy liquid quantitatively. The product was used in the next reaction without further purification. m/z (M+1) 233; IR $cm^{-1}$ 3334, 2978, 2932, 1682, 1392, 1163, 763; $^1H$ NMR ($CDCl_3$) 300 MHz δ 5.70-5.50 (s (br), 1H), 4.80-4.60 (m, 2H), 4.48-4.30 (m, 1H), 3.50-3.10 (m, 2H).

Step III: To a stirred solution of tert-butyl (4R)-4-(aminocarbonyl)-1,3-thiazolidine-3-carboxylate (23 g, 0.1 mol) in ethylacetate (50 mL) at 0° C. was added dry HCl in ethylacetate (3.5 N, 250 mL). The resulting mixture was stirred at room temperature for 2 h, the volatiles were removed under reduced pressure and the residue was triturated with ethylacetate several times to obtain (4R)-1,3-thiazolidine-4-carboxamide hydrochloride salt as an off-white powder (16.5 g) quantitatively. M.R, 201.8-203.9° C.; m/z (M+1), 133; IR $cm^{-1}$ 3387, 3250, 3189, 2857, 1706, 1675, 1612, 1371, 1123, 894; $^1H$ NMR (DMSO-$d_6$) 300 MHz δ 10.30-9.60 (s (br), ½H), 8.10 (s (br), ½H), 7.77 (s (br), 1H), 4.40 (t, J=7.0 Hz, 1H), 4.31 (d, J=9.6 Hz, 1H), 4.25 (d, J=9.6 Hz, 1H), 3.50-3.30 (m, 1H), 3.15 (dd, J=7.0, 11.7 Hz, 1H).

Step IV: To a stirred suspension of the hydrochloride salt obtained in step III (16.5 g, 0.1 mol) in dichloromethane (200 mL) cooled to 0° C. were added $Et_3N$ (41 mL, 0.3 mol) and chloroacetyl chloride (8.8 mL, 0.11 mol). The reaction mixture was slowly warmed to room temperature and stirred for 1 h. The reaction mass was filtered through a sintered funnel, the salt bed was washed with ether, and the filtrate was evaporated under vacuum to obtain the crude product (4R)-3-(chloroacetyl)-1,3-thiazolidine-4-carboxamide (20.8 g) as viscous liquid, which was used in the next step without further purification. m/z (M+1) 209; IR $cm^{-1}$ 3418, 2925, 1736, 1667, 1416, 1219, 771; $^1H$ NMR ($CDCl_3$) 300 MHz δ 6.60-6.30 (s (br), ½H), 6.0-5.65 (s (br), ½H), 5.02 (dd, J=3.6, 6.9 Hz, 0.8H), 4.88-4.75 (m, 0.4H), 4.70 (d, J=8.8 Hz, 0.8H), 4.62 (d, J=8.8 Hz, 0.8H), 4.51 (d, J=10.0 Hz, 0.2H), 4.16 (s, 1.6H), 4.11 (s, 0.4H), 3.56 (dd, J=3.4, 11.8 Hz, 0.8H), 3.44 (dd, J=4.7, 8.0 Hz, 0.4H), 3.15 (dd, J=7.1, 11.8 Hz, 0.8H), 1.28 (s, 1.6H), 1.25 (s, 7.4H).

Step V: To a stirred solution of the compound obtained in step IV (20.7 g, 0.1 mol) in dry THF (200 mL) under $N_2$ atmosphere at 0° C. was added trifluoroacetic anhydride (21 mL, 0.15 mol). The reaction mixture was gradually warmed to room temperature and stirred for 1 h. The reaction mixture was diluted with water and the two layers were separated. The aqueous layer was extracted with EtOAc and the combined organic layers were washed with brine and dried over anhydrous $Na_2SO_4$. The solvent was evaporated under reduced pressure and the residue was purified by column chromatography to yield (4R)-3-(chloroacetyl)-1,3-thiazolidine-4-carbonitrile (10.0 g) as off-white solid in 53% yield. $[\alpha]_D$, −147.24 (c, 0.5, $CHCl_3$); M.R, 85.9-87.3° C.; m/z (M+1) 191; IR $cm^{-1}$ 2982, 2936, 2245, 1679, 1666, 1393, 1284, 1261, 984, 788; $^1$H NMR (CDCl$_3$) 300 MHz δ 5.29 (t, J=4.3 Hz), 4.72 (d, J=8.8 Hz, 1H), 4.66 (d, J=8.8 Hz, 1H), 3.45-3.30 (m, 2H).

Preparation 8 tert-Butyl(3-aminotricyclo[3.3.1.0.$^{3,7}$]non-1-yl)carbamate

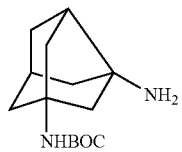

Step I: To a solution of the carboxylic acid obtained in preparation 2 step I (2.7 g, 12.9 mmol) in toluene (52 mL) at ice bath temperature Et$_3$N (5.8 mL, 38.7 mmol) and diphenylphosphoryl azide (3.3 mL, 15.5 mmol) were added. The reaction mixture was gradually warmed to room temperature, stirred for one hour, and refluxed for 4 h. Upon cooling to room temperature, the reaction mixture was transferred to a separatory funnel and washed once with water. The organic layer was transferred to an RB flask cooled to ice bath temperature and aq. KOH solution (50% w/v, 26 mL) and nBu$_4$NI (476 mg, 1.29 mmol) were added. The mixture was stirred at room temperature for 2 h. Upon completion of the reaction, the reaction mixture was cooled to ice bath temperature, acidified to pH 2 with conc. HCl, extracted once with ether, the aqueous layer was basified with aq. NaOH solution (50% w/v), and extracted with chloroform. The combined organic layers were dried over anhydrous Na$_2$SO$_4$ and the solvent was evaporated under reduced pressure to obtain the amino compound 1-(1-aminotricyclo[3.3.1.0$^{3,7}$]non-3-yl]ethanone as a viscous liquid (1.3 g) in 56% yield. m/z (M+1) 180; $^1$H NMR (CDCl$_3$) 300 MHz δ 2.68-2.61 (m, 1H), 2.49-2.43 (m, 1H), 2.17 (s, 3H), 2.05 (ddd, J=2.3, 2.3, 10.6 Hz, 1H), 1.95-1.78 (m, 3H), 1.78-1.43 (m, 6H).

Step II: To a stirred solution of the amino compound obtained in step I (1.3 g, 7.26 mmol) in dichloromethane (29 mL) at ice bath temperature Et$_3$N (2 mL, 14.5 mmol), Boc anhydride (2.1 mL, 8.7 mmol), and DMAP (44 mg, 0.36 mmol) were added. After stirring for 1 h at r.t, the solvent was removed under reduce pressure and the crude reaction mass was purified by column chromatography to obtain tert-butyl (3-acetyl tricyclo[3.3.1.0$^{3,7}$]non-1-yl)carbamate (1.8 g) as a viscous liquid in 90% yield. m/z (M+1) 280; $^1$H NMR (CDCl$_3$) 300 MHz δ 4.73 (s (br), 1H), 2.72-2.64 (m, 1H), 2.17 (s, 3H), 2.10-1.78 (m, 8H), 1.78-1.1.68 (m, 2H), 1.43 (s, 9H).

Step III: To a mixture of NaOH (1.32 g, 33.0 mmol), H$_2$O (8.8 mL), and 1,4 dioxane (2 mL) at ice bath temperature was added Br$_2$ (0.6 mL, 12.3 mmol) and stirred for 5 minutes. The resulting hypobromite solution was added dropwise to a stirred solution of the compound obtained in step II (0.6 g, 2.2 mmol) in 1,4-dioxane (2.4 mL) at around 10° C. The reaction mixture was gradually warmed to r.t, stirred for 1 h, then cooled to 0° C. and quenched by adding acetic acid (2 mL, 36.3 mmol). The mixture was diluted with water and extracted in EtOAc. The combined organic layer was washed with brine, dried over Na$_2$SO$_4$ and the solvent was removed under reduced pressure to obtain 1-[(tert-butoxycarbonyl) amino]tricyclo[3.3.1.0$^{3,7}$]nonane-3-carboxylic acid (0.54 g) as a viscous liquid in 87% yield. m/z (M−1) 280; $^1$H NMR (CDCl$_3$) 300 MHz δ 4.75 (s (br), 1H), 2.78-2.60 (m, 1H), 2.47-2.40 (m, 1H), 2.33-2.22 (m, 1H), 2.18-1.72 (m, 8H), 1.62-1.53 (m, 1H), 1.43 (s, 9H).

Step IV: To a solution of the acid (0.55 g, 1.95 mmol) obtained in step III in toluene (8 mL) at ice bath temperature Et$_3$N (1.2 mL, 8.8 mmol) and diphenylphosphoryl azide (0.5 mL, 2.3 mmol) were added. The reaction mixture was gradually warmed to r.t., stirred for one hour, and then refluxed for 4 h. Upon cooling to room temperature, the reaction mixture was transferred to a separatory funnel and washed once with water. The organic layer was transferred to a RB flask cooled to ice bath temperature and an aq. KOH solution (50% w/v, 4 mL) and nBu$_4$NI (10 mg, 0.02 mmol) were added. The reaction mixture was stirred at room temperature for 2 h. Upon completion of the reaction, the reaction mixture was cooled to ice bath temperature, acidified to pH 2 with conc. HCl, extracted once with ether, and the aqueous layer was basified with aq. NaOH solution (50% w/v) and extracted with chloroform. The combined organic layers were dried over anhydrous Na$_2$SO$_4$ and the solvent was evaporated under reduced pressure to obtain the title compound tert-butyl(3-aminotricyclo[3.3.1.0.$^{3,7}$]non-1-yl)carbamate as a viscous liquid (0.3 g) in 60% yield. m/z (M+1) 253; $^1$H NMR (CDCl$_3$) 300 MHz δ 2.35-2.28 (m, 1H), 2.20-1.80 (m, 5H), 1.78-1.53 (m, 5H), 1.52-1.47 (m, 1H), 1.43 (s, 9H).

Preparation 9

1-(3-aminotricyclo[3.3.1.0$^{3,7}$]non-1-yl)pyrrolidin-2-one

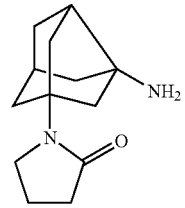

Step I: To a stirred solution of the compound obtained by preparation 8 step I (0.9 g, 5.0 mmol) in THF (20 mL) at 0° C., Et$_3$N (2.1 mL, 15 mmol) and 4-chloro butyroyl chloride (1.02 g, 7.5 mmol) were added. After stirring the reaction mixture at room temperature for 1 h, an aqueous solution of NaOH (50%, 10 mL) was added drop-wise followed by addition of n-Bu$_4$NI (182 mg, 10 mol %). After stirring the reaction mixture for 16 h, it was diluted with water and extracted in EtOAc. The combined organic layers were washed with brine, dried over Na$_2$SO$_4$, and the solvent was removed under reduced pressure. The crude product was purified by column chromatography to obtain 1-(3-acetyltricyclo[3.3.1.0$^{3,7}$]non-1-yl)pyrrolidin-2-one as viscous liquid (1.0 g) in 81% yield. m/z (M+1) 248; $^1$H NMR. (CDCl$_3$) 300 MHz δ 3.42 (t, J=6.5 Hz, 2H), 2.72-2.66 (m, 1H), 2.51-2.40 (m, 2H), 2.32 (t, J=7.8 Hz, 2H), 2.28-2.12 (m, 2H), 2.18 (s, 3H), 2.10-1.87 (m, 5H), 1.81-1.69 (m, 2H), 1.67-1.60 (m, 2H).

Step II: To a stirred mixture of NaOH (2.4 g, 60.6 mmol), H$_2$O (16 mL) and 1,4 dioxane (4 mL) at ice bath temperature was added Br$_2$ (1.13 mL, 22.6 mmol) and stirred for 5 minutes. The resulting hypobromite solution was added dropwise to a stirred solution of the compound obtained in step I (1.0 g, 4.04 mmol) in 1,4-dioxane (18 mL) at 10° C. The temperature of the reaction was brought to room temperature and the reaction mixture was stirred for 1 h. Then it was cooled to ice bath temperature and quenched by adding acetic acid (3.9 mL, 65.7 mmol). The reaction mixture was diluted with water, extracted with EtOAc, and the combined organic layers were washed with brine and dried over $Na_2SO_4$. The solvent was removed under reduced pressure to obtain 1-(2-oxopyrrolidin-1-yl)tricyclo[3.3.1.0$^{3,7}$]nonane-3-carboxylic acid as a viscous liquid (1.3 g) in 100% yield. m/z (M+1) 250; $^1$H NMR (CDCl$_3$) 300 MHz δ 3.42 (t, J=7.0 Hz, 2H), 2.78-2.71 (m, 1H), 2.47-2.23 (m, 6H), 2.08-1.90 (m, 6H), 1.85-1.72 (m, 2H), 1.62 (dd, J=2.4, 11.0 Hz, 1H).

Step III: To a stirred solution of the acid obtained in step II (0.5 g, 2.0 mmol) in CHCl$_3$ (21 mL) at room temperature was added conc. H$_2$SO$_4$ (1.0 mL, 20 mmol) followed by NaN$_3$ (0.39 g, 6.0 mmol) in portions over a period of 30 min., so that the temperature of the reaction did not rise above 40° C. The reaction was warmed to 45° C. and stirred for 2 h, then cooled to ice bath temperature, diluted with water and extracted with EtOAc. The aqueous layer was basified by adding 50% NaOH solution and extracted with CHCl$_3$. The combined organic layer was washed with brine, dried over Na$_2$SO$_4$ and the solvent was removed under reduced pressure to obtain 1-(3-aminotricyclo[3.3.1.0$^{3,7}$]non-1-yl) pyrrolidin-2-one as an off-white solid (0.25 g) in 74% yield. m/z (M+1) 221; $^1$H NMR (CDCl$_3$) 300 MHz δ 3.41 (t, J=7.0 Hz, 2H), 2.46 (dd, J=2.4, 10.3 Hz, 1H), 2.38-2.28 (m, 1H), 2.30 (t, J=8.3 Hz, 2H), 2.16-1.82 (m, 9H), 1.78 (dd J=2.6, 10.8 Hz, 1H), 1.66-1.58 (m, 1H), 1.51 (dd, J=2.5, 10.8 Hz, 1H).

Preparation 10

1-(1,1-dioxidoisothiazolidin-2-yl)tricyclo[3.3.1.0$^{3,7}$]nonan-3-amine

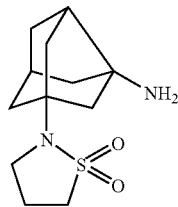

Step I: To a stirred solution of the compound obtained from the preparation 8 step I (1.0 g, 5.6 mmol) in THF (23 mL) at 0° C. was added Et$_3$N (1.2 mL, 8.4 mmol), followed by the addition of 4-chlorobutyrylchloride (1.02 g, 7.5 mmol). After stirring the reaction mixture at r.t for 1 h, an aqueous NaOH solution (50% w/v, 11 mL) was added; followed by the addition of n-Bu$_4$NI (182 mg, 0.56 mmol). The reaction mixture was stirred for 16 h, diluted with water, and extracted with EtOAc. The combined organic layer was washed with brine, dried over Na$_2$SO$_4$, and the solvent was removed under reduced pressure. The crude product was purified by column chromatography to obtain 1-[1-(1,1-di oxido isothiazolidin-2-yl)tricyclo[3.3.1.0$^{3,7}$]non-3-yl]ethanone as a viscous liquid (1.0 g) in 61% yield. m/z (M+1) 284; $^1$H NMR (CDCl$_3$) 300 MHz δ 3.37 (t, J=6.6 Hz, 2H), 3.16 (t, J=7.5 Hz, 2H), 2.76-2.69 (m, 1H), 2.53-2.47 (m, 1H), 2.39-2.26 (m, 3H), 2.18 (s, 3H), 2.22-2.07 (m, 4H), 2.20 (dd, J=3.2, 11.0 Hz, 1H), 1.96-1.89 (m, 1H), 1.78-1.69 (m, 2H), 1.61 (dd, J=2.7, 11.0 Hz, 1H).

Step II: To a stirred mixture of NaOH (2.1 g, 53.0 mmol), H$_2$O (14 mL), and 1,4 dioxane (4 mL) at ice bath temperature was added Br$_2$ (1.0 mL, 19.8 mmol) and the mixture was stirred for 5 minutes. Thus formed hypobromite solution was added drop-wise to a stirred solution of the compound obtained in step I (1.0 g, 3.53 mmol) in 1,4-dioxane (7 mL) at 10° C. The temperature of the reaction was gradually brought to room temperature and the reaction was stirred for 1 h, then it was cooled to ice bath temperature and quenched by adding AcOH (3.9 mL, 65.7 mmol). The reaction mixture was diluted with water and extracted with EtOAc. The combined organic layer was washed with brine, dried over Na$_2$SO$_4$, and the solvent was removed under reduced pressure to obtain 1-(1,1-dioxido iso thiazolidin-2-yl)tricyclo[3.3.1.0$^{3,7}$]nonane-3-carboxylic acid as a viscous liquid (0.9 g) in 90% yield. m/z (M+1) 286; $^1$H NMR (CDCl$_3$) 300 MHz δ 3.37 (t, J=6.6 Hz, 2H), 3.16 (t, J=7.8 Hz, 2H), 2.84-2.76 (m, 1H), 2.52-2.41 (m, 2H), 2.38-2.26 (m, 2H), 2.25-1.98 (m, 6H), 1.85-1.72 (m, 2H), 1.61 (dd, J=2.2, 11.3 Hz, 1H).

Step III: To a stirred solution of the acid obtained in step II (0.29 g, 1.0 mmol) in CHCl$_3$ (5 mL) at room temperature was added conc. H$_2$SO$_4$ (0.53 mL, 10 mmol) followed by the addition NaN$_3$ (0.2 g, 3.0 mmol) in portions over a period of 30 min; while maintaining the temperature below 40° C. The reaction mixture was warmed to 45° C. and stirred for 2 h. The reaction mixture was cooled to ice bath temperature, diluted with water and extracted with EtOAc. The aqueous layer was basified by adding a 50% NaOH solution and extracted with CHCl$_3$. The combined organic layer was washed with brine, dried over Na$_2$SO$_4$ and the solvent was removed under reduced pressure to obtain 1-(1,1-dioxidoisothiazolidin-2-yl)tricyclo[3.3.1.0$^{3,7}$]nonan-3-amine as a viscous liquid (0.17 g) in 66% yield. m/z (M+1) 257; $^1$H NMR (CDCl$_3$) 300 MHz δ 3.36 (t, J=6.6 Hz, 2H), 3.15 (t, J=7.5 Hz, 2H), 2.40-2.24 (m, 4H), 2.18 (dd, J=3.0, 10.4 Hz, 1H), 2.13-1.83 (m, 6H), 1.76 (dd, (J=2.4, 10.8 Hz, 1H), 1.65-1.58 (m, 1H), 1.48 (dd, J=2.4, 10.8 Hz, 1H).

Preparation 11 tert-butyl (1-hydroxytricyclo[3.3.1.0$^{3,7}$]non-3-yl) carbamate

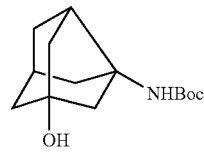

Step I: To a suspension of NaH (60% dispersed in nujol, 1.92 g, 80 mmol) in THF (80 mL) cooled to ice bath temperature was added 4-hydroxyadamantanone (6.64 g, 40 mmol) dissolved in THF (80 mL) via a syringe over a period of 15 minutes. After stirring the reaction mixture for 30 min., nBu$_4$NI (1.4 g, 4 mmol) was added followed by the addition of benzylbromide (5.26 mL). The reaction mixture was warmed to room temperature and stirred for 16 h until TLC revealed disappearance of hydroxyadamantanone. Excess NaH was quenched by adding sat. aq NH$_4$Cl solution to the ice cooled reaction mixture. The two layers were separated and the aqueous layer was extracted with EtOAc. The combined organic layer was washed with brine, dried over anhydrous Na$_2$SO$_4$, and the solvent was evaporated under reduced pressure to obtain a crude reaction mass which was purified by column chromatography to obtain 5-(benzyloxy)adamantan-2-one as a gummy liquid (7.93 g) in 77% yield. m/z (M+1), 257; $^1$H NMR (CDCl$_3$) 300 MHz δ 7.60-7.20 (m, 5H), 4.51 (s, 2H), 2.72-2.63 (m, 2H), 2.40-2.36 (m, 1H), 2.35-1.92 (m, 10H).

Step II: Freshly prepared methylmagnesium iodide in ether (0.5M, 114 mL), was added through a canula to the compound obtained in step I (7.3 g, 28.5 mmol) in THF (57 mL) at 0° C. After stirring it for 0.5 h, the reaction mixture was quenched by adding sat. aq. NH$_4$Cl solution. The organic layer was separated and the aqueous layer was extracted with isopropyl ether. The combined organic layer was washed with water and brine, dried over anhydrous Na$_2$SO$_4$, and the solvent was removed under reduced pressure to obtain 5-(benzyloxy)-2-methyl adamantan-2-ol as a gummy liquid (4:6 mixture of α and β isomers) (7.5 g) in 95% yield. m/z (M+1), 273; $^1$H NMR (CDCl$_3$) 300 MHz δ 7.42-7.20 (m, 5H), 4.51 (s, 0.8H), 4.48 (s, 1.2H), 2.40-1.30 (m, 13H), 1.40 (s, 1.2H), 1.35 (s, 1.8H).

Step III: The compound obtained in step II (7.5 g, 27.5 mmol) was dissolved in a mixture of AcOH ((5.5 mL) and THF (28 mL) and added drop-wise through an additional funnel to the ice cold solution of NaOCl (4%, 275 mL) over a period of 15 minutes. n-Bu$_4$NI (210 mg, 2 mol %) was added and the reaction mixture was stirred for 1.5 h. The reaction mixture was poured into a separation funnel and two layers were separated. The aqueous layer was extracted in diisopropylether and the combined organic layer was washed with water and brine, dried over Na$_2$SO$_4$, and the solvent was removed under reduced pressure. The crude product was refluxed with methanolic KOH solution (3.0 g KOH in 55 mL MeOH) for 1 h. The solvent was evaporated under reduced pressure and the product was purified by column chromatography to obtain methylketone 1-[1-(benzyloxy)tricyclo[3.3.1.0$^{3,7}$]non-3-yl]ethanone as a gummy liquid (4.84 g) in 65% yield. m/z (M+1), 271; 1H NMR (CDCl$_3$) 300 MHz δ 7.40-7.20 (m, 5H), 4.52 (s, 2H), 2.70-2.64 (m, 1H), 2.58-2.52 (m, 1H), 2.33-2.27 (m, 1H), 2.18 (s, 3H), 2.11-1.88 (m, 5H), 1.78-1.58 (m, 4H).

Step IV: To a mixture of NaOH (10.8 g, 270 mmol), H$_2$O (72 mL) and 1,4-dioxane (20 mL) at ice bath temperature was added Br$_2$ (5.2 mL, 100.8 mmol) and stirred for 5 minutes. This hypobromite solution was added drop-wise to a solution of the compound obtained from step III (4.84 g, 18 mmol) in 1,4-dioxane (18 mL) kept at ice bath temperature. The reaction mixture was gradually warmed to room temperature and stirred for 1 h, after which it was cooled to ice bath temperature and quenched by adding AcOH (3.9 mL, 65.7 mmol), diluted with water, and extracted in EtOAc. The combined organic layer was washed with brine, dried over Na$_2$SO$_4$, and the solvent was removed under reduced pressure to obtain 1-(benzyloxy)tricyclo[3.3.1.0$^{3,7}$]nonane-3-carboxylic acid as a gummy liquid (4.1 g) in 83% yield. m/z (M+1), 273; $^1$H NMR (CDCl$_3$) 300 MHz δ 7.40-7.20 (m, 5H), 4.52 (s, 2H), 2.78-2.70 (m, 1H), 2.58-2.48 (m, 1H), 2.45-2.37 (m, 1H), 2.18-1.50 (m, 9H).

Step V: To a solution of the acid obtained from step IV (1.36 g, 5 mmol) in toluene (20 mL) at ice bath temperature was added Et$_3$N (2.1 mL, 15 mmol) and diphenylphosphoryl azide (DPPA, 1.3 mL, 6 mmol). The reaction mixture was slowly warmed to room temperature and stirred for one hour, after which the temperature was risen to reflux for 4 h. Upon cooling to room temperature, it was transferred to a separatory funnel and washed once with water. The organic layer was transferred back to the RB flask cooled to ice bath temperature and aq. KOH solution (50% w/v, 10 mL) and nBu$_4$NI (92 mg, 0.25 mmol) were added. The reaction mixture was stirred at room temperature for 2 h. Upon completion of the reaction, the reaction mixture was cooled to ice bath temperature, acidified to pH 2 with conc, HCl, extracted once with ether, and the aqueous layer was basified with aq. NaOH solution (50% w/v), and extracted with chloroform. The combined organic layer was dried over anhydrous Na$_2$SO$_4$ and the solvent was evaporated under reduced pressure to obtain pure amine 1-(benzyloxy)tricyclo[3.3.1.0$^{3,7}$]nonan-3-amine as a gummy liquid (614 mg) in 80% yield. m/z (M+1), 244; 1H NMR (CDCl$_3$) 300 MHz δ 2.40-2.20 (m, 5H), 2.70-2.48 (m 3H), 2.40 (s (br), 1H), 2.27-2.16 (m, 1H), 2.10-1.40 (m, 9H).

Step VI: To a solution of the amino compound obtained from step V (590 mg, 2.4 mmol) in dichloromethane (10 mL) at ice bath temperature was added Et$_3$N (0.5 mL, 3.6 mmol) followed by addition of Boc anhydride (654 mg, 3.0 mmol). The reaction mixture was stirred at room temperature for 1 h. The solvent was removed under reduce pressure and the crude reaction mass was purified by column chromatography using EtOAc/hexanes as eluent to obtain the Boc derivative of tert-butyl (1-benzyloxytricyclo[3.3.1.0$^{3,7}$]non-3-yl)carbamate as a gummy liquid (740 mg) in 90% yield. m/z (M+1), 343; $^1$H NMR (CDCl$_3$) 300 MHz δ 7.40-7.20 (m, 5H), 4.80-4.70 (s (br), 1H), 4.51 (s, 2H), 2.50-2.25 (m, 4H), 2.0-1.75 (m, 6H), 1.65-1.50 (m, 2H), 1.46 (s, 9H).

Step VII: A mixture of the compound obtained from step VI (730 g, 2.1 mmol) and Pd(OH)$_2$/C (20% wet, 150 mg) in MeOH (9 mL) was stirred under H$_2$ atmosphere at room temperature for 2 h. The reaction mixture was filtered through a pad of celite and the filtrate was concentrated under reduced pressure to obtain tert-butyl (1-hydroxy tricyclo[3.3.1.0$^{3,7}$] non-3-yl)carbamate as an off-white solid (520 mg) in 97% yield. m/z (M+1), 254; $^1$H NMR (CDCl$_3$) 300 MHz δ 4.72 (s (br), 1H), 2.48-2.35 (m, 2H), 2.32-2.18 (m, 2H), 1.93-1.70 (m, 6H), 1.55-1.35 (m, 2H), 1.45 (s, 9H).

Example 1

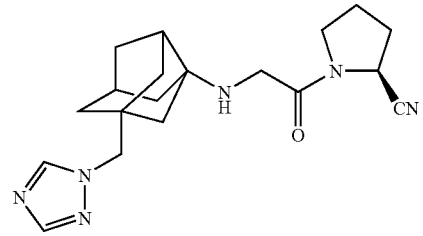

Step I: A stirred mixture of [3-(2-Methyl-1,3-dioxolan-2-yl)tricyclo[3.3.1.0$^{3,7}$]non-1-yl]methyl methanesulfonate (2.4 g, 7.5 mmol) [as obtained from preparation 2], K$_2$CO$_3$ (4.5 g, 34.2 mmol), and 1,2,4-triazole (1.5 g, 22.5 mmol) in DMF (30 mL) was heated to 110° C. for 5 h. The reaction mixture was cooled to room temperature, diluted with water, and extracted with ethylacetate. The combined organic layer was washed with brine, dried over Na$_2$SO$_4$, and the solvent was removed under reduced pressure. The crude product was purified by column chromatography to obtain 1-{[3-(2-Methyl-1,3-dioxolan-2-yl)tricyclo[3.3.1.0$^{3,7}$]non-1-yl]methyl}-1H-1,2,4-triazole (1.82 g) as a viscous liquid in 85% yield. m/z (M+1) 290; IR cm$^{-1}$ 2932, 1668, 1506, 1441, 1373, 1311, 1211, 1140, 1047, 876, 753. $^1$H NMR (CDCl$_3$) 300 MHz δ 7.99 (s, 1H), 7.93 (s, 1H), 4.07 (s, 2H), 4.03-3.92 (m, 4H), 2.42-2.32 (m, 2H), 1.86-1.79 (m, 1H), 1.74-1.65 (m, 2H), 1.52-1.37 (m, 8H), 1.26 (s, 3H).

Step II: A stirred solution of 1-{[3-(2-Methyl-1,3-dioxolan-2-yl)tricyclo[3.3.1.0$^{3,7}$]non-1-yl]methyl}-1H-1,2,4-triazole (2.6 g, 9.09 mmol) obtained from Step I and p-toluenesulfonic acid (0.16 g) in acetone (36 mL) was refluxed for 4 h. The volatiles were reduced under reduced pressure and the residue was diluted with ethylacetate, washed with 10% aq. NaHCO$_3$ and brine, dried over Na$_2$SO$_4$, and the solvent was evaporated under reduced pressure to obtain 1-[1-(1H-1,2,4-triazol-1-ylmethyl)tricyclo[3.3.1.0$^{3,7}$]non-3-yl]ethanone (2.2 g, 86% yield) as a viscous liquid. m/z (M+1) 246; $^1$H NMR (CDCl$_3$) 300 MHz δ 7.99 (s, 1H), 7.93 (s, 1H), 4.10 (s, 2H), 2.75-2.65 (m, 1H), 2.49-2.42 (m, 1H), 2.16 (s, 3H), 2.0-1.45 (m, 10H). $^{13}$C NMR (CDCl$_3$) 75 MHz δ 211.0, 151.6, 143.6, 61.6, 56.9, 48.2, 45.9, 45.7, 42.6, 41.9, 37.3, 36.6, 26.3.

Step III: To a stirred solution of NaOH (1.75 g, 43.8 mmol), H$_2$O (14.6 mL) and 1,4 dioxane (2 mL) at ice bath temperature was added Br$_2$ (0.8 mL, 16.4 mmol) and the mixture was stirred for 5 minutes. The resulting hypobromite solution was added drop-wise to a stirred solution of 1-[1-(1H-1,2,4-triazol-1-ylmethyl)tricyclo[3.3.1.0$^{3,7}$]non-3-yl]ethanone (0.7 g, 2.92 mmol) in 1,4-dioxane (4 mL) at ice bath temperature. The reaction mixture was gradually warmed to room temperature and stirred for 1 h. Then it was cooled to ice bath temperature and quenched by adding AcOH (3.9 mL, 65.7 mmol). The crude reaction mixture was diluted with water and extracted with EtOAc. The combined organic layer was washed with brine, dried over Na$_2$SO$_4$, and the solvent was removed under reduced pressure to obtain 1-(1H-1,2,4-triazol-1-ylmethyl)tricyclo[3.3.1.0$^{3,7}$]nonane-3-carboxylic acid (0.54 g) in 75% yield as an off-white solid. M.R: 230-235° C. m/z (M+1) 248. IR cm$^{-1}$ 3436, 3102, 2924, 2511, 1937, 1689, 1523, 1308, 1137, 979, 732. $^1$H NMR (CD$_3$OD) 300 MHz δ 8.43 (s, 1H), 7.9 (s, 1H), 4.17 (s, 2H), 2.70-2.62 (m, 1H), 2.40-2.33 (m, 1H), 2.06-1.95 (m, 2H), 1.84-1.1.43 (m, 8H).

Step IV: To a stirred suspension of 1-(1H-1,2,4-triazol-1-ylmethyl)tricyclo[3.3.1.0$^{3,7}$]nonane-3-carboxylic acid (0.13 g, 0.52 mmol) obtained in step III, in CHCl$_3$ (2.6 mL) was added conc. H$_2$SO$_4$ (0.25 mL, 5.2 mmol). To this homogenous solution NaN$_3$ (0.1 g, 1.56 mmol) was added in portions over a period of 30 minutes, while keeping the temperature of the reaction below 40° C. After stirring the reaction mixture for 2 h at r.t., the reaction mixture was cooled to ice bath temperature, diluted with water and extracted with EtOAc. The aqueous layer was basified by adding 50% aq. NaOH solution and extraction with CHCl$_3$. The combined organic layer was washed with brine, dried over Na$_2$SO$_4$ and the solvent was removed under reduced pressure to obtain 1-(1H-1,2,4-triazol-1-ylmethyl)tricyclo[3.3.1.0$^{3,7}$]nonan-3-amine (0.08 g) as a viscous liquid in 70% yield. m/z (M+1) 219; $^1$H NMR (CDCl$_3$) 300 MHz δ 7.98 (s, 1H), 7.93 (s, 1H), 4.07 (s, 2H), 2.38-2.30 (m, 1H), 2.06-1.98 (m, 1H), 1.96-1.80 (m, 2H), 1.72-1.57 (m, 4H), 1.55-1.36 (m, 4H).

Step V: To a stirred mixture of 1-(1H-1,2,4-triazol-1-ylmethyl)tricyclo[3.3.1.0$^{3,7}$]nonan-3-amine (0.06 g, 0.38 mmol) and K$_2$CO$_3$ (0.13 g, 0.96 mmol) in DMSO (1 mL) at an ice bath temperature was added compound (2S)-1-(chloroacetyl)pyrrolidine-2-carbonitrile (0.07 g, 0.32 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain the triazole derivative of (2S)-1-[1H-1,2,4-triazol-1-ylmethyl (tricyclo[3.3.1.0$^{3,7}$]non-3-ylamino) acetyl]pyrrolidine-2-carbonitrile (0.07 g) in 60% yield as an off-white solid, M.R: 230-235° C. m/z (M+1) 355. IR cm$^{-1}$ 3429, 2929, 2224, 1658, 1511, 1426, 1330, 1276, 1141, 1018, 747. $^1$H NMR (CDCl$_3$) 300 MHz δ 8.0 (s, 1H), 7.9 (s, 1H), 4.78 (bd, J=6.3 Hz, 1H), 4.09 (s, 2H), 3.65-3.35 (m, 4H), 2.40-2.05 (m, 8H), 1.80-1.62 (m, 4H), 1.58-1.32 (m, 4H).

Example 2

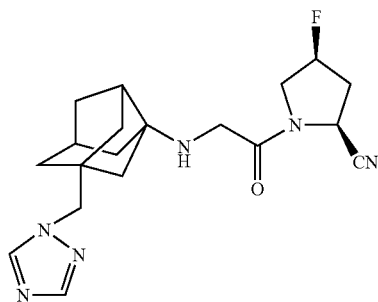

To a stirred mixture of the triazole amine as obtained in step IV in example 1 (0.65 g, 3 mmol) and K$_2$CO$_3$ (1.24 g, 9 mmol) in DMSO (12 mL) at ice bath temperature was added (2S, 4S)-1-(chloroacetyl)-4-fluoropyrrolidine-2-carbonitrile (0.57 g, 3 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S,4S)-4-fluoro-1-{N-[2-(1H-1,2,4-triazol-1-ylmethyl)hexahydro-2,5-methanopentalen-3a(1H)-yl]glycyl}pyrrolidine-2-carbonitrile as an off-white powder (0.4 g) in 36% yield. IR cm$^{-1}$ 3444, 2951, 1672, 1518, 1416, 1301, 1135, 935; m/z (M+1) 373; $^1$H NMR (CDCl$_3$) 300 MHz δ 8.0 (s, 1H), 7.92 (s, 1H), 5.44 (ddd, J=3.4, 3.4, 51.2 Hz, 0.8H), 5.35 (ddd, J=3.4, 3.4, 51.3 Hz, 0.2H), 5.04 (t, J=8.8 Hz, 0.2H), 4.95 (d, 9.2 Hz, 0.8H), 4.10 (s, 2H), 4.05-3.51 (m, 2.4H), 3.4 (s (br), 1.6H), 2.82-2.62 (m, 1H), 2.45-2.16 (m, 5H), 1.91-1.69 (m, 4H), 1.57-1.38 (m, 4H).

Example 3

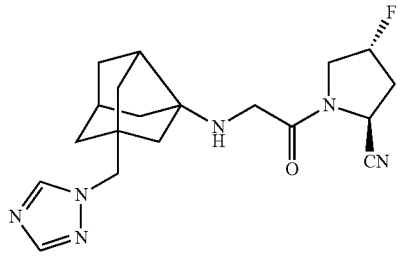

To a stirred mixture of the triazole amine as obtained in step IV in example 1 (0.4 g, 1.83 mmol) and K$_2$CO$_3$ (0.4 g, 2.8 mmol) in DMSO (4 mL) at ice bath temperature was added (2S,4R)-1-(chloroacetyl)-4-fluoropyrrolidine-2-carbonitrile (0.35 g, 1.83 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S,4R)-4-fluoro-1-{N-[2-(1H-1, 2,4-triazol-1-ylmethyl)hexahydro-2,5-methanopentalen-3a (1H)-yl]glycyl}pyrrolidine-2-carbonitrile as a gummy liquid (0.21 g) as a mixture of two rotamers in 25% yield. m/z (M+1), 373; $^1$H NMR (CDCl$_3$) 300 MHz δ 8.0 (s, 1H), 7.92 (s, 1H), 5.35 (d (br), J=51.5 Hz, 0.8H), 5.30 (d (br), J=51.3 Hz, 0.2H), 4.97 (t, J=8.4 Hz, 0.2H), 4.80 (t, 8.4 Hz, 0.8H), 4.20-3.32 (m, 4H), 4.10 (s, 2H), 2.87-2.40 (m, 1H), 2.40-2.33 (m, 1H), 2.25-2.15 (m, 1H), 1.98-1.38 (m, 11H).

Example 4

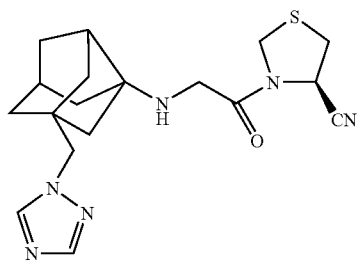

To a stirred mixture of the triazole amine as obtained in step IV example 1 (0.27 g, 1.05 mmol) and K$_2$CO$_3$ (0.58 g, 4.2 mmol) in DMSO (4 mL) at ice bath temperature was added (4R)-3-(chloroacetyl)-1,3-thiazolidine-4-carbonitrile (0.2 g, 1.05 mmol). The reaction mixture was gradually warmed to room temperature and stirred for 3 h. Upon completion of the reaction (by TLC), the reaction mixture was diluted with EtOAc and washed with water and brine, dried over Na$_2$SO$_4$, and the solvent was removed under reduced pressure. The crude product was purified by column chromatography to obtain (4R)-3-{N-[2-(1H-1,2,4-triazol-1-ylmethyl)hexahydro-2,5-methanopentalen-3a(1H)-yl]glycyl}-1,3-thiazolidine-4-carbonitrile as a light yellow solid (0.18 g) in 46% yield. m/z (M+1) 373; $^1$H NMR (CDCl$_3$) 300 MHz δ 7.99 (s, 1H), 7.92 (s, 1H), 5.32 (t, J=4.1 Hz, 1H), 4.70-4.55 (m, 2H), 4.08 (s, 2H), 3.62-3.48 (m, 2H), 3.40-3.26 (m, 2H), 2.42-2.35 (m, 1H), 2.25-2.15 (m, 1H), 1.90-1.39 (m, 10H).

Example 5

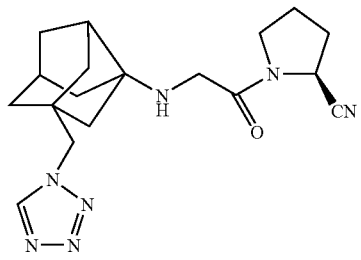

Step I: A mixture of {3-[(tert-butoxy carbonyl)amino]tricyclo[3.3.1.0$^{3,7}$]non-1-yl}methyl methanesulfonates as obtained in preparation 3 (0.8 g, 2.3 mmol), K$_2$CO$_3$ (0.95 g, 6.9 mmol), tetrazole (0.24 g, 3.45 mmol), and DMF (10.0 mL) was heated to 110° C. for 12 h. The reaction mixture was cooled to room temperature, diluted with water, and extracted with EtOAc. The combined organic layer was washed with brine, dried over Na$_2$SO$_4$, and the solvent was removed under reduced pressure. The crude product was purified by column chromatography to obtain tert-butyl [1-(1H-tetrazol-1-ylmethyl)tricyclo[3.3.1.0$^{3,7}$]non-3-yl]carbamate as a viscous liquid (0.2 g) in 27% yield. m/z (M+1) 320; $^1$H NMR (CDCl$_3$) 300 MHz δ 8.48 (s, 1H), 4.72 (s (br), 1H), 4.56 (s, 2H), 2.52-2.43 (m, 1H), 2.37-2.30 (m, 1H), 2.20-1.80 (m, 4H), 1.72 (ddd, J=2.7, 12.3, 15.4 Hz, 2H), 1.56-1.38 (m, 4H), 1.44 (s, 9H).

Step II: To a stirred solution of the compound obtained in step I above (0.2 g, 0.62 mmol) in EtOAc (2.0 mL) cooled to ice bath temperature was added a solution of dry HCl in EtOAc (3N, 3 mL). The reaction mixture was stirred at the same temperature for 2 h and the volatiles were removed under reduced pressure to obtain the crude product, which was triturated with ether several times to obtain pure hydrochloride salt of 1-(1H-tetrazol-1-ylmethyl)tricyclo[3.3.1.0$^{3,7}$]nonan-3-amine (160 mg) in 100% yield. m/z (M+1) 220; 1H NMR (CD$_3$OD) 300 MHz δ 8.72 (s, 1H), 4.70 (s, 2H), 2.52-2.43 (m, 1H), 2.42-2.37 (m, 1H), 2.0-1.80 (m, 5H), 1.70-1.50 (m, 5H).

Step III: To a stirred solution of the hydrochloride salt obtained in step II (0.162 g, 0.62 mmol) in DMSO (2.5 mL) at room temperature under nitrogen atmosphere was added (2S)-1-(chloroacetyl)pyrrolidine-2-carbonitrile (0.11 g, 0.62 mmol) and K$_2$CO$_3$ (0.34 g, 2.48 mmol). After stirring the reaction mixture for 3 h, it was diluted with EtOAc, and washed with water and brine, dried over Na$_2$SO$_4$, and the solvent was removed under reduced pressure. The crude product was purified by column chromatography to obtain (2S)-1-{N-[2-(1H-tetrazol-1-ylmethyl)hexahydro-2,5-methanopentalen-3a(1H)-yl]glycyl}pyrrolidine-2-carbonitrile as an off-white solid (0.09 g) in 40% yield. m/z (M+1) 355; 1H NMR (CDCl$_3$) 300 MHz δ 8.49 (s, 1H), 4.77 (d, J=6.7 Hz, 1H), 4.56 (s, 2H), 3.64-3.38 (m, 2H), 3.40 (s, 2H), 2.40-2.05 (m, 6H), 1.80-1.65 (m, 5H), 1.60-1.40 (m, 5H).

Example 5A

Hydrochloride salt: To a stirred solution of the compound obtained in example 5 (36 mg, 0.1 mmol) in methanol (2 mL) cooled to 0° C. was added TMS-Cl (25 μl, 0.2 mmol). After 30 minutes, the volatiles were removed under reduced pressure and the residue was triturated several times with ether to obtain off-white hydrochloride salt of (2S)-1-{N-[2-(1H-tetrazol-1-ylmethyl)hexahydro-2,5-methanopentalen-3a(1H)-yl]glycyl}pyrrolidine-2-carbonitrile (38 mg).

Example 6

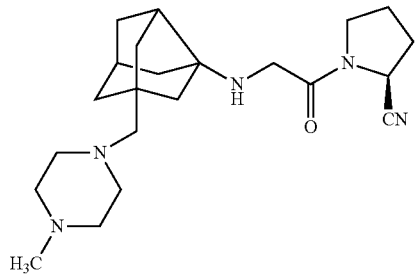

Step I: A mixture of {3-[(tert-butoxy carbonyl)amino]tricyclo[3.3.1.0$^{3,7}$]non-1-yl}methyl methanesulfonates as obtained in preparation 3 (0.85 g, 2.4 mmol), K$_2$CO$_3$ (1.0 g, 7.2 mmol), N-methylpiperazine (0.37 mL, 3.6 mmol) and DMF (10.0 mL) was heated to 110° C. for 12 h. The reaction mixture was cooled to room temperature, diluted with water and extracted in EtOAc. The combined organic layer was washed with brine, dried over Na$_2$SO$_4$ and the solvent was removed under reduced pressure. The crude product was purified by column chromatography to obtain tert-butyl [1-(4-methylpiperazin-1-yl)methyl]tricyclo[3.3.1.0$^{3,7}$]non-3-yl] carbamate as a viscous liquid (0.39 g) in 46% yield. m/z (M+1) 350; $^1$H NMR (CDCl$_3$) 300 MHz δ 4.72 (s (br), 1H), 2.55-2.25 (m, 10H), 2.48 (s, 3H), 2.38 (s, 2H), 2.0-1.85 (m, 4H), 1.80-1.72 (m, 1H), 1.70-1.40 (m, 4H), 1.45 (s, 9H), 1.35-1.22 (m, 1H).

Step II: To a stirred solution of the compound obtained according to step I (0.38 g, 1.09 mmol), in EtOAc (4.0 mL) cooled to ice bath temperature was added a solution of dry HCl in EtOAc (3 N, 6 mL). The reaction mixture was stirred at the same temperature for 2 h and the volatiles were removed under reduced pressure to obtain a crude products, which was triturated with diethyl ether several times to obtain 1-[(4-methylpiperazin-1-yl)methyl]tricyclo[3.3.1.0$^{3,7}$]nonan-3-amine hydrochloride salt (330 mg) in 85% yield.

Step III: To a stirred solution of the hydrochloride (0.33 g, 0.92 mmol) obtained in Step II, in DMSO (3.7 mL) at room temperature under nitrogen atmosphere (2S)-1-(chloroacetyl)pyrrolidine-2-carbonitrile (0.16 g, 0.92 mmol) and K$_2$CO$_3$ (0.76 g, 5.53 mmol) were added. After stirring the reaction mixture for 3 h, it was diluted with EtOAc and washed with water and brine, dried over Na$_2$SO$_4$, and the solvent was removed under reduced pressure. The crude product was purified by column chromatography to obtain (2S)-1-{N-[2-[(4-methylpiperazin-1-yl) methyl]hexahydro-2,5-methanopentalen-3a (1H)-yl]glycyl}pyrrolidine-2-carbonitrile as an off-white solid (0.12 g) in 47% yield. m/z (M+1) 386; $^1$H NMR (CDCl$_3$+CD$_3$OD) 300 MHz δ 4.78 (d, J=5.7 Hz, 1H), 3.85-3.50 (m, 4H), 3.30-3.10 (m, 5H), 2.85-2.70 (m, 8H), 2.52-2.45 (m, 2H), 2.38-2.20 (m, 4H), 2.10-1.90 (m, 4H), 1.70-1.40 (m, 5H), 1.40-1.27 (m, 1H).

Example 6A

Hydrochloride Salt: To a stirred solution of the compound obtained in example 7 (39 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain (2S)-1-{N-[2-[(4-methylpiperazin-1-yl)methyl]hexahydro-2,5-methanopentalen-3a(1H)-yl]glycyl}pyrrolidine-2-carbonitrile hydrochloride salt as an off-white solid (41 mg).

Example 7

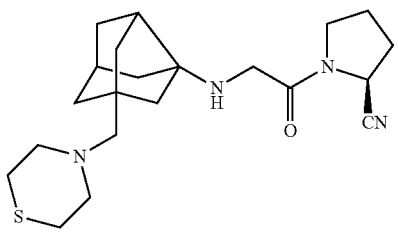

Step I: A mixture of {3-[(tert-butoxy carbonyl)amino]tricyclo[3.3.1.0$^{3,7}$]non-1-yl}methyl methanesulfonates as obtained in preparation 3 (0.85 g, 2.4 mmol), K$_2$CO$_3$ (1.0 g, 7.2 mmol), thiomorpholine (0.4 mL, 3.6 mmol) and DMF (10.0 mL) was heated to 110° C. for 12 h. The reaction mixture was cooled to room temperature, diluted with water and extracted with EtOAc. The combined organic layer was washed with brine, dried over Na$_2$SO$_4$, and the solvent was removed under reduced pressure. The crude product was purified by column chromatography to obtain tert-butyl [1-(thiomorpholin-4-ylmethyl)tricyclo[3.3.1.0$^{3,7}$]non-3-yl]carbamate as a viscous liquid (0.18 g) in 21% yield. m/z (M+1) 353; $^1$H NMR (CDCl$_3$) 300 MHz δ 4.72 (s (br), 2.75-2.66 (m, 4H), 2.65-2.58 (m, 4H), 2.40-2.28 (m, 2H), 2.17 (s, (2H), 2.0-1.85 (m, 4H), 1.80-1.72 (m, 1H), 1.62-1.50 (m, 4H), 1.45 (s, 9H), 1.35-1.20 (m, 1H).

Step II: To a stirred solution of the compound (0.22 g, 0.63 mmol) obtained in step I, in EtOAc (2.0 mL) cooled to ice bath temperature was added a solution of dry HCl in EtOAc (3 N, 4 mL). The reaction mixture was stirred at same temperature for 2 h and the solvent was removed under reduced pressure to obtain a crude product, which was triturated several times with diethyl ether to obtain 1-(thiomorpholin-4-ylmethyl) tricyclo[3.3.1.0$^{3,7}$]nonan-3-amine hydrochloride salt (180 mg) in 88% yield.

Step III: To a stirred solution of the hydrochloride salt (0.17 g, 0.51 mmol) obtained in step II above in DMSO (2.0 mL) at room temperature under nitrogen atmosphere was added (2S)-1-(chloroacetyl)pyrrolidine-2-carbonitrile (0.09 g, 0.52 mmol) and K$_2$CO$_3$ (0.35 g, 2.55 mmol. After stirring the reaction mixture for 3 h, it was diluted with EtOAc and washed with water and brine, dried over Na$_2$SO$_4$ and the solvent was removed under reduced pressure. The crude product was purified by column chromatography to obtain (2S)-1-{N-[2-(thiomorpholin-4-ylmethyl)hexahydro-2,5-methanopentalen-3a(1H)-yl]glycyl}pyrrolidine-2-carbonitrile as an off-white solid (0.07 g) in 35% yield. m/z (M+1) 389; $^1$H NMR (CDCl$_3$) 300 MHz δ 4.83-4.75 (m, 1H), 3.90-3.45 (m, 4H), 2.85-2.70 (m, 4H), 2.70-2.60 (m, 4H), 2.48-2.35 (m, 2H), 2.35-2.15 (m, 4H), 2.0-1.75 (m, 4H), 1.68-1.40 (m, 5H), 1.38-1.25 (m, 1H).

Example 7A

Hydrochloride salt: To a stirred solution of the compound obtained in example 7 (39 mg, 0.1 mmol), in methanol (2 mL) cooled to 0° C. was added TMS-Cl (25 μL, 0.2 mmol). After 30 minutes, the volatiles were removed under reduced pressure and the residue was triturated several times with diethyl ether to obtain the hydrochloride salt of (2S)-1-{N-[2-(thiomorpholin-4-ylmethyl)hexahydro-2,5-methanopentalen-3a (1H)-yl]glycyl}pyrrolidine-2-carbonitrile as off-white solid (41 mg).

Example 8

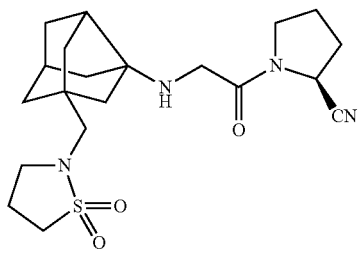

Step I: A stirred mixture of [3-(2-Methyl-1,3-dioxolan-2-yl)tricyclo[3.3.1.0$^{3,7}$]non-1-yl]methyl methanesulfonate as obtained in preparation 2 (1.0 g, 2.9 mmol), K$_2$CO$_3$ (1.16 g, 8.7 mmol) and isothiazolidine-1,1-dioxide (0.53 g, 4.35 mmol) in DMF (12.0 mL) was heated to 110° C. for 16 h. The reaction mixture was cooled to room temperature, diluted with water and extracted with EtOAc. The combined organic layer was washed with brine, dried over $Na_2SO_4$ and the solvent was removed under reduced pressure. The crude product was purified by column chromatography to obtain 2-{[3-(2-methyl-1,3-dioxolan-2-yl)tricyclo[3.3.1.0$^{3,7}$]non-1-yl]methyl}isothiazolidine 1,1-dioxide as a viscous liquid (0.69 g) in 70% yield. m/z (M+1) 342; $^1$H NMR (CDCl$_3$) 300 MHz δ 4.04-3.92 (m, 4H), 3.30 (t, J=6.8 Hz, 2H), 3.10 (t, J=7.4 Hz, 2H), 2.94 (d, J=14.6 Hz, 1H), 2.87 (d, J=14.6 Hz, 1H), 2.40-2.27 (m, 4H), 1.88-1.72 (m, 2H), 1.72-1.55 (m, 4H), 1.55-1.38 (m, 4H), 1.27 (s, 3H).

Step II: A stirred solution of the compound obtained by Step I (0.68 g, 2.0 mmol) and p-toluenesulfonic acid (38 mg, 0.2 mmol) in acetone (8 mL) was refluxed for 4 h. The reaction mixture was diluted with EtOAc and washed with 10% aq. NaHCO$_3$ and brine, dried over Na$_2$SO$_4$, and the solvent was evaporated under reduced pressure to obtain 1-{1-[(1,1-dioxido isothiazolidin-2-yl)methyl]tricyclo[3.3.1.0$^{3,7}$]non-3-yl}ethanone (0.55 g) in 92% yield as a viscous liquid.

Step III: To a stirred mixture of NaOH (1.2 g, 27.8 mmol), H$_2$O (8 mL), and 1,4 dioxane (1 mL) at ice bath temperature was added Br$_2$ (0.56 mL, 10.4 mmol) and the mixture was stirred for 15 minutes. The resulting hypobromite solution was added drop-wise to a stirred solution of the compound obtained in step II (0.55 g, 1.85 mmol) in 1,4-dioxane (3 mL) at ice bath temperature. The reaction mixture was gradually warmed to room temperature and after stirring for 1 h; it was cooled to ice bath temperature and quenched by adding AcOH (1.7 mL, 27.8 mmol). The reaction mixture was diluted with water and extracted with EtOAc. The combined organic layer was washed with brine, dried over Na$_2$SO$_4$, and the solvent was removed under reduced pressure to obtain 1-[(1,1-dioxidoisothiazolidin-2-yl)methyl]tricyclo[3.3.1.0$^{3,7}$]nonane-3-carboxylicacid (0.39 g) in 70% yield. m/z (M−1) 298; $^1$H NMR (CDCl$_3$) 300 MHz δ 3.32 (t, J=6.8 Hz, 2H), 3.10 (t, J=7.4 Hz, 2H), 2.95 (s, 2H), 2.80-2.73 (m, 1H), 2.43-2.41 (m, 1H), 2.40-2.29 (m, 2H), 2.10-2.0 (m, 2H), 1.82-1.72 (m, 3H), 1.67-1.54 (m, 4H), 1.46 (dd, J=3.2, 11.0 Hz, 1H).

Step IV: To a stirred solution of the acid obtained in step III (0.39 g, 1.31 mmol) in CHCl$_3$ (7 mL) was added conc. H$_2$SO$_4$ (1.4 mL, 26 mmol). Solid NaN$_3$ (0.26 g, 3.93 mmol) was added slowly in portions by keeping the reaction temperature below 40° C. The reaction mixture was stirred at r.t for 2, h then it was cooled to ice bath temperature, diluted with water, and extracted with EtOAc. The aqueous layer was basified by adding 50% NaOH solution and extracted with CHCl$_3$. The combined organic layer was washed with brine, dried over Na$_2$SO$_4$, and the solvent was evaporated under reduced pressure to obtain 1-[(1,1-dioxidoisothiazolidin-2-yl) methyl]tricyclo[3.3.1.0$^{3,7}$]nonan-3-amine (0.26 g) as viscous liquid in 74% yield. m/z (M+1) 271; $^1$H NMR (CDCl$_3$) 300 MHz δ 3.32 (t, J=6.8 Hz, 2H), 3.10 (t, J=7.4 Hz, 2H), 2.92 (s, 2H), 2.40-2.28 (m, 3H), 2.01-1.83 (m, 3H), 1.75-1.52 (m, 6H), 1.50-1.43 (m, 1H), 1.39-1.32 (m, 1H).

Step V: To a stirred mixture of the amine obtained in step IV (0.26 g, 0.96 mmol) and K$_2$CO$_3$ (0.42 g, 2.9 mmol) in DMSO (4.0 mL) at ice bath temperature was added under nitrogen atmosphere (S)-1-(2-chloro-acetyl)pyrrolidine-2-carbonitrile (0.17 g, 1.0 mmol). After stirring the reaction mixture for 3 h at r.t, it was diluted with EtOAc, washed with water and brine, dried over Na$_2$SO$_4$, and the solvent was evaporated under reduced pressure. The crude product was purified by column chromatography to obtain (2S)-1-{N-[2-[(1,1-dioxidoisothiazolidin-2-yl)methyl]hexahydro-2,5-methanopentalen-3a(1H)-yl]glycyl}pyrrolidine-2-carbonitrile as an off-white solid (0.17 g) in 43% yield. m/z (M+1) 407; $^1$H NMR (CDCl$_3$) 300 MHz δ 4.87-4.76 (m, 1H), 3.70-3.40 (m, 2H), 3.44 (s, 2H), 3.32 (t, J=6.7 Hz, 2H), 3.10 (t, J=7.5 Hz, 2H), 2.93 (s, 2H), 2.41-2.10 (m, 8H), 1.90-1.46 (m, 7H), 1.43-1.35 (m, 1H).

Example 9

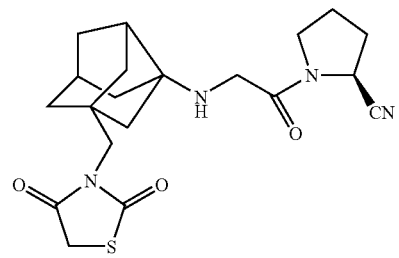

Step I: A mixture of the compound obtained in preparation 3 (0.9 g, 2.6 mmol), K$_2$CO$_3$ (1.1 g, 7.8 mmol) and thiazolidine-2,4-dione (0.47 g, 4.0 mmol) in DMF (10.5 mL) was heated to 110° C. for 12 h. The reaction mixture was cooled to room temperature, diluted with water, and extracted with EtOAc. The combined organic layer was washed with brine, dried over Na$_2$SO$_4$, and the solvent was removed under reduced pressure. The crude product was purified by column chromatography to obtain 3{3-[(tert-butoxycarbonyl)amino]tricyclo[3.3.1.0$^{3,7}$]non-1-yl}methyl-1,3-thiazolidine-2,4-dione as a viscous liquid (0.28 g) in 25% yield. m/z (M+1) 367; $^1$H NMR (CDCl$_3$) 300 MHz δ 4.72 (s (br), 1H), 3.96 (s, 2H), 3.57 (s, 2H), 2.46-2.38 (m, 1H), 2.38-2.30 (m, 1H), 2.02-1.85 (m, 4H), 1.80-1.70 (m, 1H), 1.63 (dd, J=2.9, 10.5 Hz, 1H), 1.52-1.40 (m, 3H), 1.44 (s, 9H), 1.37 (dd, J=3.0, 11.0 Hz, 1H).

Step II: To a stirred solution of the compound obtained in step I (0.2 g, 0.54 mmol) in EtOAc (2.0 mL) cooled to ice bath temperature was added a solution of dry HCl in EtOAc (3N, 3 mL). The reaction mixture was stirred at the same temperature for 2 h and the solvent was removed under reduced pressure to obtain a crude product, which was triturated with diethyl ether several times to obtain the hydrochloride salt (165 mg) in 100% yield. m/z (M+1) 267; $^1$H NMR (CD$_3$OD) 300 MHz δ 4.10 (s, 2H), 3.60 (dd, J=9.0, 11.0 Hz, 2-H), 2.48-2.42 (m, 1H), 2.34 (ddd, J=1.6, 6.9, 8.5 Hz, 1H), 1.88-1.68 (m, 6H), 1.68-1.53 (m, 3H), 1.50 (dd, J=2.0, 11.4 Hz, 1H).

Step III: To a stirred solution of the hydrochloride salt obtained in step II (0.165 g, 0.54 mmol) in DMSO (2.2 mL) at room temperature under nitrogen atmosphere (S)-1-(2-chloro-acetyl)pyrrolidine-2-carbonitrile (0.1 g, 0.54 mmol) and K$_2$CO$_3$ (0.23 g, 1.62 mmol) was added sequentially. After stirring the reaction mixture for 3 h, it was diluted with EtOAc and washed with water and brine, dried over Na$_2$SO$_4$, and the solvent was removed under reduced pressure. The crude product was purified by column chromatography to obtain (2S)-1-{N-[2-[(2,4-dioxo-1,3-thiazolidin-3-yl)methyl] hexahydro-2,5-methanopentalen-3a(1H)-yl] glycyl}pyrrolidine-2-carbonitrile as an off-white solid (0.11 g) in 50% yield. m/z (M+1) 358; 1H NMR (CDCl$_3$) 300 MHz δ 4.77 (d, J=7.4 Hz, 1H), 3.96 (s, 2H), 3.75-3.38 (m, 2H), 3.56 (s, 2H), 3.41 (s, 2-H), 2.40-2.10 (m, 6H), 1.90-1.57 (m, 10H), 1.57-1.33 (m, 4H).

3.72-3.38 (m, 2H), 3.60 (s, 2H), 3.40 (s, 2H), 2.40-2.05 (m, 7H), 1.90-1.78 (m, 2H), 1.70-1.40 (m, 3H).

Example 10

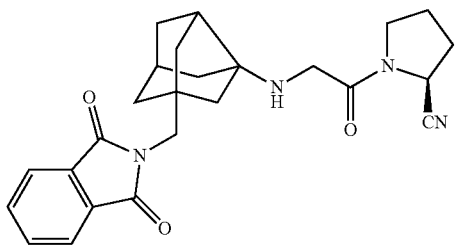

Example 11

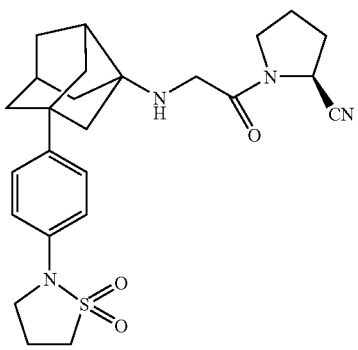

Step I: To a stirred solution of tert-butyl [1-(hydroxymethyl)tricyclo[3.3.1.0$^{3,7}$]non-3-yl]carbamate (as obtained in step VI preparation 3) (0.67 g, 2.5 mmol) in toluene (10 mL) was added phthalimide (0.52 g, 3.5 mmol), triphenylphosphine (1.05 g, 4.0 mmol), and diisopropylazodicarboxylate (0.8 mL, 4.0 mmol). The reaction mixture was heated to 90° C. for 4 h. The volatiles were removed under reduced pressure and the residue was purified by column chromatography to obtain tert-butyl [2-[(1,3-dioxo-1,3-dihydro-2H-isoindol-2-yl)methyl]hexahydro-2,5-methanopentalen-3a(1H)-yl]carbamate (0.45 g) as a viscous liquid in 46% yield. m/z (M+1) 397; $^1$H NMR (CDCl$_3$) 300 MHz δ 7.90-7.80 (m, 2H), 7.77-7.68 (m, 2H), 4.75 (s (br), 1H), 3.60 (s, 2H), 2.47-2.35 (m, 1H), 2.36-2.29 (m, 1H), 2.02-1.84 (m, 4H), 1.77-1.65 (m, 2H), 1.64-1.35 (m, 5H), 1.41 (s, 9H), 1.34-1.24 (m, 1H).

Step II: To a stirred solution of the compound obtained from step I (0.45 g, 1.12 mmol) in dichloromethane (1.1 mL) at 0° C. was added trifluoroacetic acid (1.1 mL). The reaction mixture was gradually warmed to room temperature and stirred for 1 h. The volatiles were removed under vacuum and the residue was triturated several times with diethyl ether to obtain 2-[(3-aminotricyclo[3.3.1.0$^{3,7}$]non-1-yl)methyl]-1H-isoindole-1,3(2H)-dione (0.4 g) as its trifluoroacetic acid salt in 86% yield. m/z (M+1) 297; $^1$H NMR (DMSO-d$_6$) 300 MHz δ 8.05 (s (br), 2H), 7.92-7.80 (m, 4H), 3.51 (s, 2H), 2.38-2.30 (m, 1H), 2.30-2.22 (m, 1H), 1.85-1.66 (m, 6H), 1.60-1.50 (m, 3H), 1.45-1.38 (m, 1H).

Step III: To a stirred mixture of the compound obtained from step II (0.4 g, 0.98 mmol) and K$_2$CO$_3$ (0.54 g, 3.92 mmol) in DMSO (4.0 mL) at ice bath temperature under nitrogen atmosphere was added (S)-1-(2-chloro-acetyl)pyrrolidine-2-carbonitrile (0.17 g, 1.0 mmol). After stirring the reaction mixture at r.t for 3 h, it was diluted with EtOAc and washed with water and brine, dried over Na$_2$SO$_4$, and the solvent was removed under reduced pressure. The crude product was purified by column chromatography to obtain (2S)-1-{N-[2-[(1,3-dioxo-1,3-dihydro-2H-isoindol-2-yl)methyl]hexahydro-2,5-methanopentalen-3a(1H)-yl] glycyl}pyrrolidine-2-carbonitrile as an off-white solid (0.18 g) in 43% yield. m/z (M+1) 433; $^1$H NMR (CDCl$_3$) 300 MHz δ 7.90-7.80 (m, 2H), 7.75-7.65 (m, 2-H), 4.86-4.72 (m, 1H), Step I: To a stirred solution of benzyl[2-(4-aminophenyl) hexahydro-2,5-methanopentalene-3a(1H)-yl]carbamate (1.1 g, 3.03 mmol) obtained from preparation 4, in THF (30 mL) at 0° C. was added Et$_3$N (0.66 mL, 4.6 mmol) and 3-chloropropanesulfonylchloride (0.42 mL, 3.3 mmol). The reaction mixture was warmed to room temperature and stirred for 1 h. An aqueous solution of NaOH (50% w/v, 6 mL) was added followed by addition of n-Bu$_4$NI (56 mg, 0.15 mmol). After stirring the reaction mixture for 16 h, it was diluted with water and extracted in EtOAc. The combined organic layer was washed with brine, dried over Na$_2$SO$_4$, and the solvent was removed under reduced pressure and the crude product was purified by column chromatography to obtain benzyl[2-[4-(1,1-dioxidoisothiazolidin-2-yl)phenyl)hexahydro-2,5-methanopentalene-3a(1H)-yl]carbamate as an off-white solid (0.93 g) in 66% yield. M.R: 215.6-219.2° C. m/z (M+1) 467; IR cm$^{-1}$ 3441, 2953, 1716, 1516, 1314, 1215, 770. $^1$H NMR (CDCl$_3$) 300 MHz δ 7.40-7.16 (m, 9H), 5.13-5.0 (bs, 2H), 3.75 (t, J=6.6 Hz, 2H), 3.35 (t, J=7.5 Hz, 2H), 2.59-2.38 (m, 4H), 2.30-1.60 (m, 10H).

Step II: A mixture of benzyl[2-[4-(1,1-dioxidoisothiazolidin-2-yl)phenyl)hexahydro-2,5-methanopentalene-3a(1H)-yl]carbamate (0.8 g, 1.7 mmol) obtained in step I, Pd/C (10%, 0.4 g) in MeOH (17 mL) was stirred at room temperature under H$_2$ atmosphere for 2 h. The reaction mixture was filtered through a pad of celite and the filtrate was concentrated under reduced pressure to obtain 1-[4-(1,1-dioxidoisothiazolidin-2-yl)phenyl]tricyclo[3.3.1.0$^{3,7}$]nonan-3-amine as an off-white solid (0.49 g) in 85% yield. m/z (M+1) 333; IR cm$^{-1}$ 3418, 1652, 1137, 772. $^1$H NMR (CDCl$_3$) 300 MHz, δ 7.31 (d, J=8.8 Hz, 2H), 7.22 (d, J=8.8 Hz, 2H), 3.78 (t, J=6.6 Hz, 2H), 3.43 (t, J=7.4 Hz, 2H), 2.58-2.47 (m, 3H), 2.40-2.34 (m, 1H), 2.27-2.11 (m, 2H), 2.10-1.95 (m, 4H), 1.93-1.70 (m, 4H).

Step III: To a stirred mixture of 1-[4-(1,1-dioxidoisothiazolidin-2-yl)phenyl]tricyclo[3.3.1.0$^{3,7}$]nonan-3-amine (0.4 g, 1.2 mmol) and K$_2$CO$_3$ (0.48 g, 3.6 mmol) in DMSO (4.8 mL) at ice bath temperature was added (2S)-1-(chloroacetyl) pyrrolidine-2-carbonitrile (0.25 g, 1.44 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S)-1-{N-[2-[4-(1,1-dioxidoisothiazolidin-2-yl)phenyl]hexahydro-2,5-methanopentalen-3a(1H)-yl]glycyl}pyrrolidine-2-carbonitrile as a white solid (0.28 g) in 50% yield. M.R, 214-216° C. m/z (M+1) 469; IR cm$^{-1}$ 3436, 2932, 2240, 1658, 1517, 1414, 1308, 1137, 952, 740. $^1$H NMR (300 MHz, CD$_3$OD) δ: 7.35 (d, J=8.5 Hz, 2H), 7.23 (d, J=8.5 Hz, 2H), 4.85 (t, J=5.4 Hz, 1H), 4.15-3.95 (m, 2H), 3.81-3.70 (m, 3H), 3.60-3.50 (m, 1H), 3.42 (t, J=7.4 Hz, 2H), 2.65-2.45 (m, 4H), 2.40-1.75 (m, 14H).

Example 12

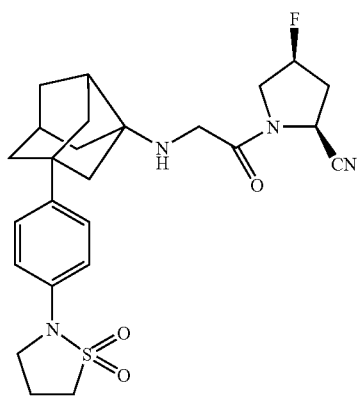

To a stirred mixture of 1-[4-(1,1-dioxidoisothiazolidin-2-yl)phenyl]tricyclo[3.3.1.0$^{3,7}$]nonan-3-amine (as obtained in example 8 Step II) (0.17 g, 0.5 mmol) and K$_2$CO$_3$ (0.21 g, 1.5 mmol) in DMSO (2 mL) at an ice bath temperature was added (2S,4S)-1-(chloroacetyl)-4-fluoropyrrolidine-2-carbonitrile (0.1 g, 0.5 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S,4S)-1-{N-[2-[4-(1,1-dioxido-isothiazolidin-2-yl)phenyl]hexahydro-2,5-methanopen-talen-3a(1H)-yl]glycyl}-4-fluoropyrrolidine-2-carbonitrile as an off-white powder (0.09 g) in 37% yield as a 3:1 mixture of two rotomers. IR cm$^{-1}$ 3438, 2953, 2776, 1673, 1518, 1427, 1301, 1135, 1078, 955; m/z (M+1) 487; $^1$H NMR (CDCl$_3$) 300 MHz δ 7.25 (d, J=6.2 Hz, 2H), 7.20 (d, J=8.6 Hz, 2H), 5.42 (d (br), J=51.0 Hz, 0.8H), 5.34 (d (br), J=50.4 Hz, 0.2H), 5.15 (d, J=10.2 Hz, 0.2H), 4.98 (d, J=7.4 Hz, 0.8H), 4.0-3.50 (m, 4H), 3.76 (t, J=6.5H, 2H), 3.35 (t, J=6.5 Hz, 2H), 2.80-2.28 (m, 6H), 2.15-1.58 (m, 10H).

Example 13

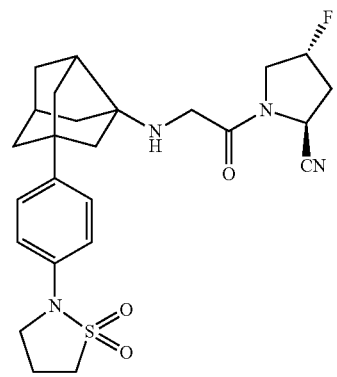

To a stirred mixture of 1-[4-(1,1-dioxidoisothiazolidin-2-yl)phenyl]tricyclo[3.3.1.0$^{3,7}$]nonan-3-amine as obtained in example 8 step II (0.22 g, 0.7 mmol) and K$_2$CO$_3$ (0.3 g, 2.1 mmol) in DMSO (3.4 mL) at ice bath temperature was added (2S,4R)-1-(chloroacetyl)-4-fluoropyrrolidine-2-carbonitrile (0.13 g, 2.1 mmol). The reaction mixture was gradually warmed to room temperature and stirred for 3 h. Upon completion of the reaction (by TLC), the reaction mixture was diluted with EtOAc and washed with water and brine, dried over Na$_2$SO$_4$, and the solvent was removed under reduced pressure. The crude product was purified by column chromatography to obtain (2S,4R)-1-{N-[2-[4-(1,1-dioxido-isothiazolidin-2-yl)phenyl]hexahydro-2,5-methanopen-talen-3a(1H)-yl]glycyl}-4-fluoropyrrolidine-2-carbonitrile as an off-white powder (0.14 g) as a 3:1 mixture of two rotomers in 43% yield. m/z (M+1) 487; $^1$H NMR (CDCl$_3$) 300 MHz δ 7.25 (d, J=7.9 Hz, 2H), 7.20 (d, J=8.7 Hz, 2H), 5.35 (d (br), J=51.4 Hz, 0.8H), 5.28 (d (br), J=50.7 Hz, 0.2H), 5.02 (t, J=7.2 Hz, 0.2H), 4.80 (t, J=8.4 Hz, 0.8H), 4.02-3.41 (m, 4H), 3.76 (t, J=6.6H, 2H), 3.37 (t, J=7.4 Hz, 2H), 2.85-2.25 (m, 6H), 2.15-1.55 (m, 10H).

Example 14

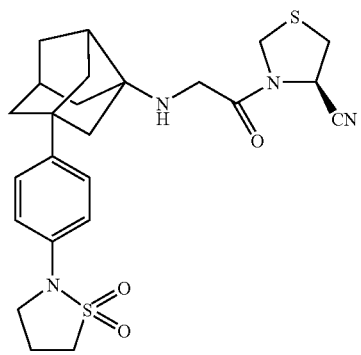

To a stirred mixture of 1-[4-(1,1-dioxidoisothiazolidin-2-yl)phenyl]tricyclo[3.3.1.0$^{3,7}$]nonan-3-amine as obtained in example 8 step II (0.25 g, 1.1 mmol) and K$_2$CO$_3$ (0.46 g, 3.3 mmol) in DMSO (5 mL) at ice bath temperature was added (4R)-3-(chloroacetyl)-1,3-thiazolidine-4-carbonitrile (0.2 g, 1.1 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (4R)-3-{N-[2-[4-(1,1-dioxidoisothiazolidin-2-yl)phenyl]hexahydro-2,5-methanopentalen-3a(1H)-yl]glycyl}-1,3-thiazolidine-4-carbonitrile as an off-white powder (0.1 g) in 40% yield. m/z (M+1) 487; IR cm$^{-1}$ 3444, 2952, 2873, 1672, 1518, 1416, 1301, 1135, 953; $^1$H NMR (CDCl$_3$) 300 MHz δ 7.25 (d, J=6.2 Hz, 2H), 7.20 (d, J=8.6 Hz, 2H), 5.38-5.48 (m, 1H), 4.72-4.51 (m, 2H), 3.75 (t, J=6.6 Hz, 2H), 3.70-3.55 (m, 1H), 3.36 (t, J=7.4 Hz, 2H), 3.32-3.20 (m, 1H), 2.60-2.40 (m, 4H), 2.20-1.58 (m, 10).

Example 15

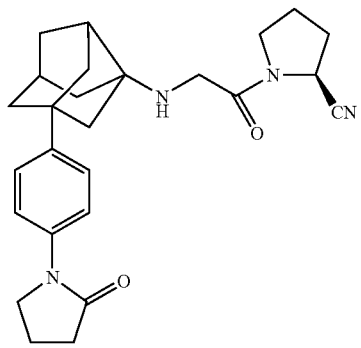

Step I: To a stirred solution of benzyl[2-(4-aminophenyl)hexahydro-2,5-methanopentalen-3a(1H)-yl]carbamate (1.1 g, 3.03 mmol) obtained in preparation 4, in THF (30 mL) at 0° C. was added sequentially Et$_3$N (0.66 mL, 4.6 mmol) and 4-chlorobutyrylchloride (0.37 mL, 3.3 mmol). The reaction mixture was warmed to room temperature and stirred for 1 h. An aqueous solution of NaOH (50% w/v, 6 mL) was added followed by addition of n-Bu$_4$NI (56 mg, 0.15 mmol) and the reaction was stirred for 16 h. The reaction mixture was diluted with water and extracted in EtOAc. The combined organic layer was washed with brine, dried over Na$_2$SO$_4$, the solvent was removed under reduced pressure, and the crude product was purified by column chromatography to obtain benzyl[2-[4-(2-Oxopyrrolidin-1-yl)phenyl)hexahydro-2,5-methanopentalene-3a(1H)-yl]carbamate as an off-white solid (0.9 g, 69% yield). m/z (M+1) 431; $^1$H NMR (CDCl$_3$) 300 MHz δ 7.55 (d, J=8.6 Hz, 2H), 7.42-7.20 (m, 7H), 5.15-5.0 (bs, 2H), 3.87 (t, J=7.0 Hz, 2H), 2.67-2.53 (m, 3H), 2.48-2.42 (m, 1H), 2.35-1.55 (m, 12H).

Step II: A mixture of benzyl[2-[4-(2-Oxopyrrolidin-1-yl)phenyl)hexahydro-2,5-methanopentalene-3a(1H)-yl]carbamate (0.73 g, 1.7 mmol) obtained in step I and Pd/C (10%, 0.4 g) in MeOH (17 mL) was stirred at room temperature under H$_2$ atmosphere for 2 h. The reaction mixture was filtered through a pad of celite and the filtrate was concentrated under reduced pressure to obtain 1-[4-(3-aminotricyclo[3.3.1.0$^{3,7}$]non-1-yl)phenyl]pyrrolidin-2-one as an off-white solid (0.43 g, 85% yield). m/z (M+1) 297; $^1$H NMR (CDCl$_3$) 300 MHz δ 7.52 (d, J=8.6 Hz, 2H), 7.25 (d, J=8.6 Hz, 2H), 3.86 (t, J=6.9 Hz, 2H), 2.62 (t, J=7.9 Hz, 2H), 2.52-2.42 (m, 1H), 2.32-1.60 (m, 13H).

Step III: To a stirred solution of 1-[4-(3-aminotricyclo[3.3.1.0$^{3,7}$]non-1-yl)phenyl]pyrrolidin-2-one obtained in step II (0.36 g, 1.2 mmol) in DMSO (4.8 mL) at an ice bath temperature under nitrogen atmosphere was added K$_2$CO$_3$ (0.48 g, 3.6 mmol) followed by addition of (2S)-1-(chloroacetyl)pyrrolidine-2-carbonitrile (0.21 g, 1.2 mmol). After stirring the reaction mixture at r.t for 3 h, it was diluted with EtOAc and washed with water and brine, dried over Na$_2$SO$_4$, and the solvent was removed under reduced pressure. The crude product was purified by column chromatography to obtain the title compound (2S)-1-{N-[2-[4-(2-oxopyrrolidin-1-yl)phenyl]hexahydro-2,5-methanopentalen-3a(1H)-yl]glycyl}pyrrolidine-2-carbonitrile as a white solid (0.26 g) in 50% yield. M.R: 254-256° C.; m/z (M+1) 433; $^1$H NMR (300 MHz, CDCl$_3$) δ: 7.54 (d, J=8.5 Hz, 2H), 7.23 (d, J=8.5 Hz, 2H), 4.30-4.20 (m, 1H), 4.06-4.18 (m, 2H), 3.87 (t, J=7.0 Hz, 1H), 3.80-3.50 (m, 4H), 2.64 (t, J=7.8 Hz, 2H), 2.58-1.60 (m, 18H).

Example 16

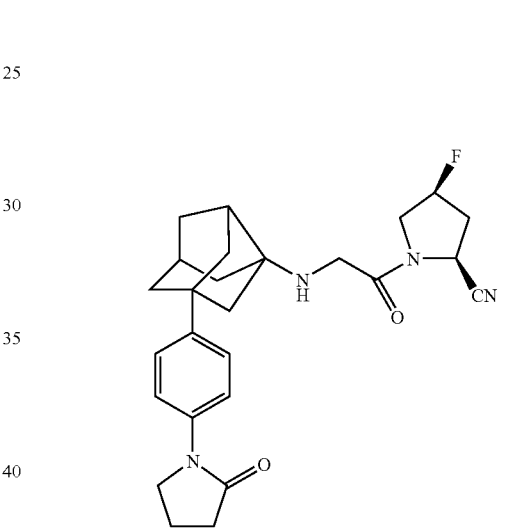

To a stirred mixture of the lactam amine, 1-[4-(3-aminotricyclo[3.3.1.0$^{3,7}$]non-1-yl)phenyl]pyrrolidin-2-one as obtained in example 12, Step II, (0.15 g, 0.5 mmol) and K$_2$CO$_3$ (0.21 g, 1.5 mmol) in DMSO (2 mL) at an ice bath temperature was added (2S,4S)-1-(chloroacetyl)-4-fluoropyrrolidine-2-carbonitrile (0.1 g, 0.5 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S,4S)-4-fluoro-1-{N-[2-[4-(2-oxopyrrolidin-1-1)phenyl]hexahydro-2,5-methanopentalen-3a(1H)-yl]glycyl}pyrrolidine-2-carbonitrile as off-white powder (0.11 g) in 49% yield. m/z (M+1) 451; $^1$H NMR (CDCl$_3$) 300 MHz δ 7.51 (d, J=8.5 Hz, 2H), 7.25 (d, J=8.5 Hz, 2H), 5.43 (ddd, J=3.1, 3.1, 51.3 Hz, 1H), 5.12 (d, J=8.7 Hz, 0.2H), 4.97 (d, J=9.5H), 4.05-3.62 (m, 2H), 3.85 (t, J=6.9 Hz, 2H), 3.55-3.40 (m, 2H), 2.81-2.61 (m, 1H), 2.60 (t, J=8.2 Hz, 2H), 2.49-2.40 (m, 1H), 2.32-2.25 (m, 1H), 2.21-2.05 (m, 4H), 2.0-1.60 (m, 9H).

Example 17

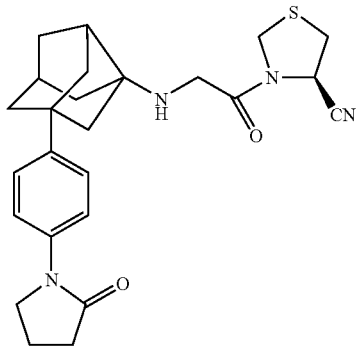

To a stirred mixture of the lactam amine obtained in example 12, step II (0.15 g, 0.5 mmol) and K$_2$CO$_3$ (0.21 g, 1.5 mmol) in DMSO (2 mL) at ice bath temperature was added (4R)-3-(chloroacetyl)-1,3-thiazolidine-4-carbonitrile (0.1 g, 1.1 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$ and the solvent was removed under reduced pressure. The crude product was purified by column chromatography to obtain (4R)-3-{N-[2-[4-(2-oxopyrrolidin-1-yl)phenyl]hexahydro-2,5-methanopentalen-3a(1H)-yl]glycyl}-1,3-thiazolidine-4-carbonitrile as an off-white powder (0.09 g) in 40% yield. m/z (M+1), 451; $^1$H NMR (CDCl$_3$) 300 MHz δ 7.51 (d, J=6.7 Hz, 2H), 7.24 (d, J=7.0 Hz, 2H), 5.34 (t, J=4.1 Hz, 1H), 4.65 (d, J=7.5 Hz, 1H), 4.60 (d, J=7.5 Hz, 1H), 3.85 (t, J=6.9 Hz, 2H), 3.70-3.55 (m, 2H), 3.40-3.25 (m, 2H), 2.60 (t, J=7.8 Hz, 2H), 2.49-2.42 (m, 1H), 2.33-2.25 (m, 1H), 2.21-2.02 (m, 4H), 2.0-1.6 (m, 8H).

Example 18

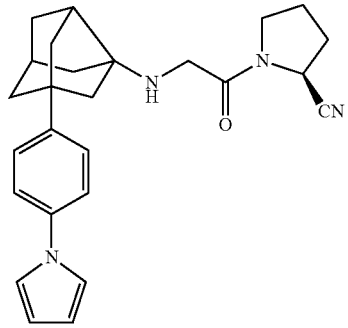

Step I: To a stirred solution of benzyl[2-(4-aminophenyl)hexahydro-2,5-methanopentalene-3a(1H)-yl]carbamate obtained from preparation 4 (1.09 g, 3.0 mmol) in glacial acetic acid (12 mL) was added 2,5-dimethoxytetrahydrofuran (0.44 g, 3.3 mmol). The reaction mixture was heated under reflux for 1 h. The mixture was diluted with ethylacetate, washed with water, 10% aq. NaHCO$_3$ and brine. The combined organic layer was dried over anhydrous Na$_2$SO$_4$ and the solvent was evaporated under reduced pressure. The crude product was purified by column chromatography to obtain benzyl[2-[4-(1H-pyrrol-1-yl)phenyl]hexahydro-2,5-methanopentalen-3a(1H)-yl]carbamate (0.8 g) in 65% yield as a viscous liquid. m/z (M+1) 413; $^1$H NMR (CDCl$_3$) 300 MHz δ 7.50-7.20 (m, 9H), 7.08-7.04 (m, 2H), 6.37-6.30 (m, 2H), 5.10 (s, 2H), 2.65-2.52 (m, 1H), 2.50-2.42 (m, 1H), 2.40-2.12 (m, 2H), 2.10-1.70 (m, 6H), 1.70-1.52 (m, 2H).

Step II: To a stirred solution of the compound obtained from step I (0.8 g, 1.94 mmol) in MeOH (20 mL) Pd/C (10%, 0.1 g) was added. The reaction mixture was stirred at r.t. for 2 h under H$_2$ pressure with a balloon. The reaction mixture was filtered through a pad of celite and the filtrate was concentrated under reduced pressure to obtain 2-[4-(1H-pyrrol-1-yl)phenyl]hexahydro-2,5-methanopentalen-3a(1H)-amine (0.45 g) as a viscous liquid (0.45 g) in 83% yield. m/z (M+1) 279; $^1$H NMR (CD$_3$OD) 300 MHz δ 7.40-7.25 (m, 4H), 7.20-7.05 (m, 2H), 6.30-6.20 (m, 2H), 2.57-2.46 (m, 1H), 2.46-2.38 (m, 1H), 2.30-2.13 (m, 2H), 2.13-1.81 (m, 7H), 1.80-1.70 (m, 1H).

Step III: To a stirred mixture of the compound obtained from step II (0.41 g, 1.5 mmol) and K$_2$CO$_3$ (0.62 g, 4.5 mmol) in DMSO (6 mL) at ice bath temperature under N$_2$ atmosphere was added (S)-1-(2-chloro-acetyl)pyrrolidine-2-carbonitrile (0.26 g, 1.5 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S)-1-{N-[2-[4-(1H-pyrrol-1-yl)phenyl]hexahydro-2,5-methanopentalen-3a (1H)-yl]glycyl}pyrrolidine-2-carbonitrile as a white solid (0.2 g) in 32% yield as off-white solid. m/z (M+1) 415; $^1$H NMR (CDCl$_3$) 300 MHz δ 7.38-7.26 (m, 4H), 7.10-7.05 (m, 2H), 6.36-6.32 (m, 2H), 4.84-4.78 (m, 1H), 3.75-3.40 (m, 2H), 3.50 (s, 2H), 2.50-2.42 (m, 1H), 2.38-2.28 (m, 2H), 2.25-2.0 (m, 6H), 2.0-1.70 (m, 7H).

Example 19

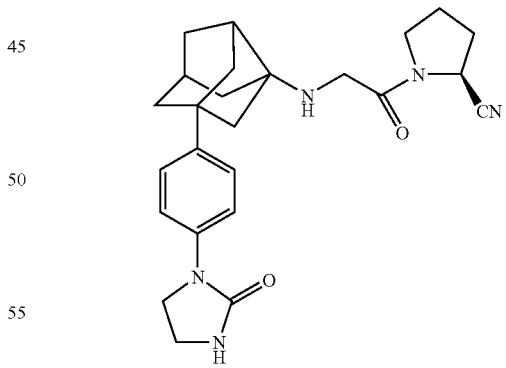

Step I: To a stirred solution of benzyl[2-(4-aminophenyl)hexahydro-2,5-methanopentalene-3a(1H)-yl]carbamate obtained by preparation 4 (1.09 g, 3.0 mmol) in THF (12 mL) at 0° C. was added Et$_3$N (0.65 mL, 4.5 mmol), followed by addition of 2-chloro ethylisocyanate (0.3 mL, 3.3 mmol). The reaction mixture was warmed to room temperature and stirred for 1 h. An aqueous solution of NaOH (50% w/v, 6 mL) was added followed by n-Bu$_4$NI (55 mg, 0.15 mmol) and the reaction mixture was stirred for 16 h. The two layers were separated and the aqueous layer was extracted with EtOAc. The combined organic layer was washed with brine, dried over Na$_2$SO$_4$ and the solvent was evaporated under reduced pressure. The crude product was purified by column chromatography to obtain benzyl[2-[4-(2-oxoimidazolidin-1-yl]hexahydro-2,5-methanopentalene-3a(1H)-yl]carbamate (0.7 g) as an off-white solid in 54% yield. m/z (M+1) 432; $^1$H NMR (CDCl$_3$) 300 MHz δ 7.44 (d, J=8.8 Hz, 2H), 7.40-7.30 (m, 5H), 7.21 (d, J=8.8 Hz, 2H), 5.09 (s, 2H), 3.92 (t, J=7.4 Hz, 2H), 3.55 (t, J=8.5 Hz, 2H), 2.59-2.50 (m, 1H), 2.44-2.38 (m, 1H), 2.30-2.11 (m, 3H), 2.11-1.90 (m, 3H), 1.89-1.66 (m, 2H), 1.64-1.46 (m, 2H).

Step II: To a stirred solution of the compound obtained from step I (0.65 g, 1.5 mmol) in MeOH (15 mL) Pd/C (10%, 0.1 g) was added. The reaction mixture was stirred at room temperature for 2 h under H$_2$ pressure with a balloon. The reaction mixture was filtered through a pad of celite and the filtrate was concentrated under reduced pressure to obtain 1-[4-(3-amino tricyclo[3.3.1.0$^{3,7}$]non-1-yl)phenyl]imidazolidin-2-one (0.4 g) as an off-white solid in 90% yield. M.R: 215-220° C.; m/z (M+1) 298; IR cm$^{-1}$ 3412, 3245, 2955, 1687, 1518, 1485, 1263, 805; $^1$H NMR (CDCl$_3$+DMSO-d$_6$) 300 MHz δ 8.26 (s (br), 2H), 7.46 (d, J=8.7 Hz, 2H), 7.16 (d, J=8.7 Hz, 2H), 6.70 (s (br), 1H), 3.86 (t, J=7.3 Hz, 2H), 3.48 (t, J=7.3 Hz, 2H), 2.50-2.45 (m, 1H), 2.22-2.07 (m, 3H), 2.02-1.63 (m, 8H).

Step III: To a stirred mixture of the compound obtained from step II (0.4 g, 1.35 mmol) and K$_2$CO$_3$ (0.56 g, 4.05 mmol) in DMSO (6 mL) at ice bath temperature under N$_2$ atmosphere was added (S)-1-(2-chloro-acetyl)pyrrolidine-2-carbonitrile (0.23 g, 1.35 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was evaporated under reduced pressure. The crude product was purified by column chromatography to obtain (2S)-1-{N-[2-[4-(2-oxoimidazolidin-1-yl)phenyl]hexahydro-2,5-methanopentalen-3a(1H)-yl]glycyl}pyrrolidine-2-carbonitrile as an off-white solid (0.21 g) in 36% yield. m/z (M+1) 434; $^1$H NMR (CDCl$_3$) 300 MHz δ 7.45 (d, J=8.8 Hz, 2H), 7.23 (d, J=8.8 Hz, 2H), 4.86-4.76 (m, 1H), 4.67 (s (br), 1H), 3.93 (t, J=7.4 Hz, 2H), 3.75-3.40 (m, 4H), 3.48 (s, 2H), 3.46-2.38 (m, 1H), 2.36-2.23 (m, 2H), 2.23-1.70 (m, 12H), 1.65-1.57 (m, 1H).

Example 20

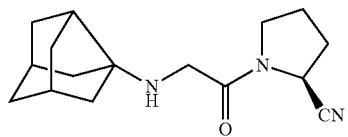

Step I: To a stirred mixture of tricyclo[3.3.1.0$^{3,7}$]nonan-3-amine (0.28 g, 2.0 mmol) and K$_2$CO$_3$ (0.83 g, 6.0 mmol) in DMSO (8 mL) at ice bath temperature under N$_2$ atmosphere was added (S)-1-(2-chloro-acetyl)pyrrolidine-2-carbonitrile (0.34 g, 2.0 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S)-1-[(tricyclo[3.3.1.0$^{3,7}$]non-3-ylamino)acetyl]pyrrolidine-2-carbonitrile as a viscous liquid (0.23 g) in 42% yield. m/z (M+1) 274; 1H NMR (CDCl$_3$) 300 MHz δ 4.87-4.76 (m, 1H), 3.71-3.40 (m, 2H), 3.41 (s, 2H), 2.35-2.05 (m, 7H), 1.92-1.74 (m, 6H), 1.68-1.48 (m, 4H).

Example 19A

Hydrochloride salt: To a stirred solution of the compound obtained in example 18 (27 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain hydrochloride salt of (2S)-1-[(tricyclo[3.3.1.0$^{3,7}$]non-3-ylamino)acetyl]pyrrolidine-2-carbonitrile as an off-white solid (31 mg). m/z (M+1) 274; $^1$H NMR (DMSO-d$_6$) 300 MHz δ 9.44 (s (br), 2H), 4.86 (dd, J=4.4, 7.0 Hz, 1H), 4.10-3.88 (m, 2H), 3.78-3.65 (m, 1H), 3.60-3.47 (m, 1H), 2.48-2.41 (m, 1H), 2.34-2.27 (m, 2H), 2.26-2.17 (m, 2H), 2.10-1.99 (m, 2H), 1.99-1.83 (m, 6H), 1.63-1.43 (m, 4H).

Example 21

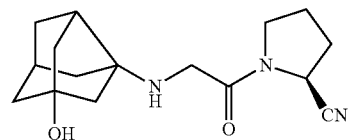

Step I: To a stirred solution of tert-butyl (1-hydroxytricyclo[3.3.1.0$^{3,7}$]non-3-yl)carbamate as obtained in preparation 11 (500 mg, 1.97 mmol) in EtOAc (5 mL) cooled to ice bath temperature was added a solution of dry HCl in EtOAc (4N, 5 mL). After the reaction mixture was stirred for 2 h, the volatiles were removed under reduced pressure. The crude product was triturated with diethyl ether several times to obtain 3-aminotricyclo[3.3.1.0$^{3,7}$]nonan-1-ol hydrochloride (280 mg) in 75% yield. m/z (M+1) 154; 1H NMR (CD$_3$OD) 300 MHz δ 2.51-2.44 (m, 1H), 2.34 (ddd, J=2.0, 7.0, 8.9 Hz, 1H), 2.17-2.04 (m, 2-H), 1.94-1.71 (m, 6H), 1.60-1.53 (m, 2H).

Step II: To a stirred mixture of the compound obtained in step I (280 mg, 1.5 mmol) and K$_2$CO$_3$ (820 mg, 6 mmol) in DMSO (6 mL) at ice bath temperature under N$_2$ atmosphere was added (S)-1-(2-chloro-acetyl)pyrrolidine-2-carbonitrile (205 mg, 1.2 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S)-1-{[(1-hydroxytricyclo[3.3.1.0$^{3,7}$]non-3-yl)amino]acetyl}pyrrolidine-2-carbonitrile as a viscous liquid (150 mg) in 35% yield. m/z (M+1) 291; $^1$H NMR (CDCl$_3$) 300 MHz δ 4.78 (d, J=7.0 Hz, 1H), 3.75-3.38 (m, 2H), 3.43 (s, 2H), 2.45-37 (m 1H), 2.35-1.95 (m, 8H), 1.90-1.60 (m, 6H), 1.53-1.40 (m, 2H).

Example 22

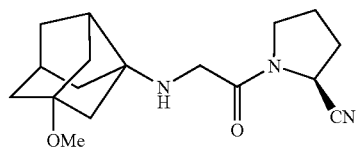

Step I: To a suspension of NaH (60% dispersed in nujol, 0.96 g, 24 mmol) in THF (40 mL) cooled to ice bath temperature was added hydroxyadamantanone (3.32 g, 20 mmol) dissolved in THF (40 mL) via a syringe over a period of 15 minutes. After stirring the reaction mixture for 30 min., iodomethane (1.38 mL, 22 mmol) was added. The reaction mixture was warmed to room temperature and stirred for 16 h until TLC revealed completion of the reaction. Excess NaH was quenched by adding saturated aq. NH$_4$Cl solution to the ice cooled reaction mixture. The two layers were separated and the aqueous layer was extracted with EtOAc. The combined organic layer was washed with brine, dried over anhydrous Na$_2$SO$_4$, and the solvent was evaporated under reduced pressure to obtain crude reaction mass which was purified by column chromatography to yield 5-methoxyadamantan-2-one (3.0 g) in 83% yield. m/z (M+1), 181; $^1$H NMR (CDCl$_3$) 300 MHz δ 3.26 (s, 3H), 2.67-2.61 (m, 2H), 2.39-2.33 (m, 1H), 2.20-1.93 (m, 10H).

Step II: Freshly prepared methyl magnesium iodide in ether (1M, 32 mL), was added through a canula to 5-methoxyadamantan-2-one (3.0 g, 16 mmol) in THF (32 mL) at 0° C. After stirring the mixture at 0° C. for 0.5 h, the reaction mixture was quenched by adding saturated aq. NH$_4$Cl solution. The organic layer was separated and the aqueous layer was extracted with diethyl ether. The combined organic layer was washed with water and brine, dried over anhydrous Na$_2$SO$_4$, and the solvent was evaporated under reduced pressure to obtain 5-methoxy-2-methyladamantan-2-ol as 1:1 anomeric mixture (3.0 g yield, 96%). m/z (M+23), 219; $^1$H NMR (CDCl$_3$) 300 MHz δ 3.24 (s, 1½H), 3.23 ((s, 1½H), 2.68-2.62 (m, 1H), 2.40-1.55 (m, 10H), 1.53-1.35 (m, 2H), 1.38 (s, 3H).

Step III: 5-methoxy-2-methyladamantan-2-ol (3.0 g, 15 mmol), dissolved in a mixture of AcOH (3.0 mL) and THF (15 mL) was added dropwise by a dropping funnel to an ice bath cooled solution of NaOCl (4%, 150 mL) over a period of 15 minutes. n-Bu$_4$NI (0.55 g, 1.5 mmol) was added and the reaction mixture was stirred for 1.5 h. The reaction mixture was separated into two layers. The aqueous layer was extracted with diisopropylether and the combined organic layer was washed with water and brine, dried over Na$_2$SO$_4$, and the solvent was evaporated under reduced pressure to obtain hypochlorite which was diluted with methanol (30 mL) and solid KOH (1.68 g, 30 mmol) was added. The reaction mixture was refluxed for 1 h. The volatiles were removed and the crude product was diluted with ether, washed with water, brine, dried over anhydrous Na$_2$SO$_4$, and the solvent was evaporated under vacuum. The crude product was purified by column chromatography to obtain 1-(1-methoxytricyclo[3.3.1.0$^{3,7}$]non-3-yl)ethanone (1.92 g) in 66% yield. m/z (M+1) 195; $^1$H NMR (CDCl$_3$) 300 MHz δ 3.29 (s, 3H), 2.69-2.62 (m, 1H), 2.57-2.50 (m, 1H), 2.26-2.16 (m, 1H), 2.18 (s, 3H), 2.10-1.61 (m, 7H), 1.59-1.52 (m, 2H).

Step IV: To a mixture of NaOH (5.8 g, 147 mmol), H$_2$O (40.0 mL) and 1,4 dioxane (10 mL) at ice bath temperature was added Br$_2$ (2.8 mL, 55.0 mmol) and stirred for 5 minutes. The resulting hypobromite solution was added drop-wise to a stirred solution of 1-(1-methoxytricyclo[3.3.1.0$^{3,7}$]non-3-yl)ethanone obtained from step III (1.9 g, 9.8 mmol), in 1,4-dioxane (10 mL) at ice bath temperature. The reaction mixture was gradually warmed to room temperature and stirred for 1 h. The reaction mixture was cooled to ice bath temperature and AcOH (3.9 mL, 65.7 mmol) were added. The reaction mixture was diluted with water and extracted with EtOAc. The combined organic layer was washed with brine, dried over Na$_2$SO$_4$, and the solvent was removed under reduced pressure to obtain 1-methoxytricyclo[3.3.1.0$^{3,7}$]nonane-3-carboxylic acid (1.3 g) in 72% yield. m/z (M+1), 197; 1H NMR (CDCl$_3$) 300 MHz δ 3.30 (s, 3H), 2.78-2.70 (m, 1H), 2.57-2.48 (m, 1H), 2.38-2.28 (m, 1H), 2.11-2.0 (m, 2H), 1.86-1.69 (m, 5H), 1.59-1.51 (m, 2H).

Step V: To the suspension of 1-methoxytricyclo[3.3.1.0$^{3,7}$]nonane-3-carboxylic acid obtained from step IV (0.39 g, 2.0 mmol) in CHCl$_3$ (10 mL) was added conc. H$_2$SO$_4$ (1.0 mL, 20 mmol). Solid NaN$_3$ (0.39 g, 6.0 mmol) was added in portions by keeping the reaction temperature below 40° C. After stirring at room temperature for 2 hrs, the reaction mixture was cooled to ice bath temperature, diluted with water and extracted with EtOAc. The aqueous layer was basified by adding 50% NaOH solution and extracted with CHCl$_3$. The combined organic layer was washed with brine, dried over Na$_2$SO$_4$, and the solvent was removed under reduced pressure to obtain 1-methoxytricyclo[3.3.1.0$^{3,7}$]nonan-3-amine (0.23 g) in 69% yield. m/z (M+1) 168; $^1$H NMR (CDCl$_3$) 300 MHz δ 3.27 (s, 3H), 2.40-2.34 (m, 1H), 2.16-2.08 (m, 1H), 1.97 (ddd, J=2.0, 6.8, 8.7 Hz, 1H), 1.92-1.53 (m, 7H), 1.51-1.38 (m, 2H).

Step VI: To a stirred solution of the amino compound obtained by step V (0.16 g, 0.95 mmol) in DMSO (4.0 mL) was added (S)-1-(2-chloro-acetyl)pyrrolidine-2-carbonitrile (0.17 g, 0.96 mmol) and K$_2$CO$_3$ (0.4 g, 2.9 mmol). The reaction mixture was gradually warmed to room temperature and stirred for 3 h. The reaction mixture was diluted with EtOAc and washed with water ad brine, dried over Na$_2$SO$_4$, and the solvent was removed under reduced pressure. The crude product was purified by column chromatography to obtain (2S)-1-{[(1-methoxytricyclo[3.3.1.0$^{3,7}$]non-3-yl)amino]acetyl}pyrrolidine-2-carbonitrile (0.12 g) in 41% yield. m/z (M+1) 304; 1H NMR (CDCl$_3$) 300 MHz δ 4.82-4.75 (m, 1H), 3.75-3.40-m, 4H), 3.27 (s, 3-H), 2.47-2.40 (m, 1H), 2.35-1.68 (13H), 1.57-1.41 (m, 2H).

Example 16A

Hydrochloride salt: To a stirred solution of the compound prepared in example 16 (30 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain (2S)-1-{[(1-methoxytricyclo[3.3.1.0$^{3,}$ 7]non-3-yl)amino]acetyl}pyrrolidine-2-carbonitrile hydrochloride salt as off-white solid (30 mg).

Example 23

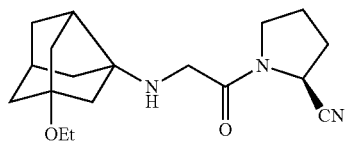

The process is as given for the methoxy compound prepared in Example 16, with the difference that in the first step ethylating agent n-Bu$_4$NI and ethylbromide are used; the remaining process is similar.

Step I: To a suspension of NaH (60% dispersed in nujol, 0.96 g, 24 mmol) in THF (40 mL) cooled to ice bath temperature was added hydroxyadamantanone (3.32 g, 20 mmol) dissolved in THF (40 mL) via a syringe over a period of 15 minutes. The reaction mixture was stirred for 30 min then n-Bu$_4$NI (0.74 g, 2 mmol) and ethyl bromide (1.6 mL, 22 mmol) were added. The reaction mixture was warmed to room temperature and stirred for 16 h. After cooling the reaction mixture to 0° C., the excess NaH was quenched by adding sat. aq. NH$_4$Cl solution. The two layers were separated and the aqueous layer was extracted with EtOAc. The combined organic layer was washed with brine, dried over anhydrous Na$_2$SO$_4$, and the solvent was evaporated under reduced pressure to obtain a crude reaction mass, which was purified by column chromatography to yield 5-ethoxyadamantan-2-one (3.0 g) in 77% yield. m/z (M+1) 195; 1H NMR (CDCl$_3$) 300 MHz δ 3.47 (q, J=7.0 Hz, 2H), 2.67-2.60 (m, 2H), 2.38-2.30 (m, 1H), 2.13-1.78 (m, 10H), 1.17 (t, J=7.0 Hz, 3H).

Step II: 5-Ethoxy-2-methyladamantan-2-ol from 5-Ethoxyadamantan-2-one, as 1:1 anomeric mixture (1.6 g) in 99% yield. m/z (M+23) 233; $^1$H NMR (CDCl$_3$) 300 MHz δ 3.51-3.41 (m, 2H), 2.31-2.23 (m, 1H), 2.18-2.05 (m, 2H), 2.02-1.80 (m, 4H), 1.79-1.47 (m, 7H), 1.46-1.32 (m, 4H), 1.16 (t, J=6.5 Hz, 3H).

Step III: 1-(1-ethoxytricyclo[3.3.1.0$^{3,7}$]non-3-yl)ethanone from 5-Ethoxy-2-methyladamantan-2-ol in 66% yield. m/z (M+1) 209; $^1$H NMR (CDCl$_3$) 300 MHz δ 3.49 (q, J=7.1 Hz, 2H), 2.69-2.61 (m, 1H), 2.56-2.48 (m, 1H), 2.22-2.18 (m, 1H), 2.17 (s, 3H), 2.02-1.84 (m, 4H), 1.78-1.50 (m, 5H), 1.18 (t, J=7.1 Hz, 3H).

Step IV: 1-ethoxytricyclo[3.3.1.0$^{3,7}$]nonane-3-carboxylic acid prepared from 1-(1-ethoxytricyclo[3.3.1.0$^{3,7}$]non-3-yl)ethanone in 68% yield. m/z (M+1) 195; $^1$H NMR (CDCl$_3$) 300 MHz δ 3.49 (q, J=6.7 Hz, 2H), 2.75-2.68 (m, 1H), 2.52-2.47 (m, 1H), 2.36-2.28 (m, 1H), 2.10-1.95 (m, 2H), 1.83 (s, 1.86-1.68 (m, 5H), 1.54 (ddd, J=3.0, 10.9, 13.6 Hz 2H), 1.18 (t, J=6.7 Hz, 3H).

Step V: 1-Ethoxytricyclo[3.3.1.0$^{3,7}$]nonan-3-amine from 1-ethoxytricyclo[3.3.1.0$^{3,7}$]nonane-3-carboxylic acid in 53% yield. m/z (M+1) 182; $^1$H NMR (CDCl$_3$) 300 MHz δ 3.49 (q, J=7.0 Hz, 2H), 2.39-2.32 (m, 1H), 2.16-2.07 (m, 1H), 1.99-1.92 (m, 1H), 1.92-1.75 (m, 5H), 1.71-1.38 (m, 4H), 1.17 (t, J=7.0 Hz, 3H).

Step VI: Coupling reaction between amine from step V and cyano pyrrolidine compound to form (2S)-1-{[(1-ethoxytricyclo[3.3.1.0$^{3,7}$]non-3-yl)amino]acetyl}pyrrolidine-2-carbonitrile in 41% yield. m/z (M+1) 318; $^1$H NMR (CDCl$_3$) 300 MHz δ 4.81-4.75 (m, 1H), 3.75-3.40 (m, 6H), 2.45-2.37 (m, 1H), 2.36-2.13 (m, 4H), 2.12-1.95 (m, 2H), 1.88-1.68 (m, 6H), 1.56 (ddd, J=3.0, 3.0, 10.5 Hz 1H), 1.49-1.41 (m, 1H), 1.17 (t, J=7.0 Hz, 3H).

Example 17A

Hydrochloride salt: To a stirred solution of the compound obtained from example 17 (32 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain the hydrochloride salt of (2S)-1-{[(1-ethoxy tricyclo[3.3.1.0$^{3,7}$]non-3-yl)amino] acetyl}pyrrolidine-2-carbonitrile as an off-white solid (30 mg). m/z (M+1) 318; $^1$H NMR (DMSO-d$_6$) 300 MHz δ 9.41 (s (br), 2H), 4.86 (dd, J=4.6, 6.8 Hz, 1H), 4.10-3.90 (m, 2H), 3.75-3.65 (m, 1H), 3.57-3.25 (m, 3H), 2.48-2.38 (m, 2H), 2.30-2.17 (m, 2H), 2.16-2.0 (m, 4H), 1.90-1.14 (m, 6H), 1.53-1.40 (m, 2H), 1.06 (t, J=7.0 Hz, 3H).

Example 24

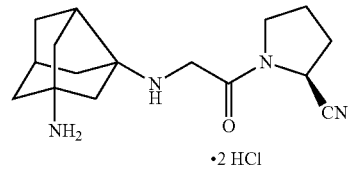

•2 HCl

Step I: To a stirred mixture of the compound obtained in preparation 8 (0.3 g, 1.2 mmol) and K$_2$CO$_3$ (0.5 g, 3.6 mmol) in DMSO (5 mL) at ice bath temperature under N$_2$ atmosphere was added (S)-1-(2-chloro-acetyl)pyrrolidine-2-carbonitrile (0.14 g, 0.83 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain tert-Butyl-(2S)-1-{[(1-aminotricyclo[3.3.1.0$^{3,7}$]non-3-yl)carbamate] acetyl}pyrrolidine-2-carbonitrile as a viscous liquid (0.18 g) in 40% yield. m/z (M+1) 389; $^1$H NMR (CDCl$_3$) 300 MHz δ 4.79 (d, J=7.5 Hz, 1H), 4.70 (s (br), 1H), 3.70-3.40 (m, 2H), 3.46 (s, 2H), 2.40-2.32 (m, 1H), 2.32-1.90 (m, 6H), 1.90-1.63 (m, 5H), 1.55-1.43 (m, 1H).

Step II: To a stirred solution of the compound obtained in step I (0.04 g, 0.1 mmol) in EtOAc (2 mL) cooled to ice bath temperature was added a solution of dry HCl in EtOAc (3N, 2 mL). The reaction mixture was stirred for 2 h and the solvent was removed under reduced pressure to obtain a crude product which was triturated with diethyl ether several times to obtain dihydrochloride salt of (2S)-1-{[(1-aminotricyclo[3.3.1.0$^{3,7}$]non-3-yl)amino]acetyl}pyrrolidine-2-carbonitrile (0.02 g) in 69% yield. m/z (M+1) 289; $^1$H NMR (DMSO-d$_6$) 300 MHz δ 9.69 (s (br), 2H), 8.57 (s (br), 3H), 4.86 (dd, J=4.4, 7.0 Hz, 1H), 4.16-3.90 (m, 2H), 3.78-3.65 (m, 1H), 3.65-3.50 (m, 1H), 2.60-2.55 (m, 1H), 2.50-2.43 (m, 1H), 2.35-2.18 (m, 4H), 2.13-1.98 (m, 2H), 2.10-2.0 (m, 3H), 1.96-1.70 (m, 5H), 1.68-1.60 (m, 1H), 1.50-1.43 (m, 2H).

Example 25

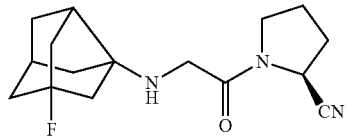

Step I: To a stirred solution of tert-butyl (1-hydroxytricyclo[3.3.1.0$^{3,7}$]non-3-yl)carbamate obtained from preparation 11 (1.1 g, 4.34 mmol) in dichloromethane cooled to −15° C., under N$_2$ atmosphere was added diethylaminosulfur trifluoride (0.85 mL, 6.51 mmol). The reaction mixture was stirred at this temperature for 1 h and subsequently stirred at room temperature for 16 h. The reaction mixture was cooled to ice bath temperature and quenched by adding a mixture of crushed ice and solid NaHCO$_3$ (1.1 g, 13 mmol). Two layers were separated and the aqueous layer was extracted with chloroform. The combined organic layer was washed with brine, dried over anhydrous Na$_2$SO$_4$, and the solvent was evaporated under reduced pressure. The crude product was purified by column chromatography to obtain tert-butyl (1-fluorotricyclo[3.3.1.0$^{3,7}$]non-3-yl)carbamate (0.26 g) as viscous liquid in 24% yield. m/z (M−1) 254; $^1$H NMR (CDCl$_3$) 300 MHz δ 2.55-2.40 (m, 1H), 2.01.75 (m, 2H), 1.70-1.40 (m, 9H), 1.57 (s, 6-H), 1.45 (s, 3H).

Step II: To a stirred solution of the compound obtained from step I (0.25 g, 0.98 mmol) in EtOAc (1 mL) cooled to ice bath temperature was added a solution of dry HCl in EtOAc (3N, 3 mL). After stirring the reaction mixture for 2 h, the volatiles were removed under reduced pressure. The crude product was triturated with ether several times to obtain 1-fluorotricyclo[3.3.1.0$^{3,7}$]nonan-3-amine, hydrochloride salt (0.19 g) in 99% yield. m/z (M+1) 156; $^1$H NMR (DMSO-d$_6$) 300 MHz δ 8.45 (s br), 2H), 2.47-2.18 (m, 4H), 1.96-1.72 (m, 6-H), 1.63 (dd, J=2.6, 9.5 Hz, 1H), 1.50-1.42 (m, 1H).

Step III: To a stirred mixture of the hydrochloride salt obtained from step II (0.19 g, 0.98 mmol) and K$_2$CO$_3$ (0.53 g, 4.0 mmol) in DMSO (4.0 mL) at ice bath temperature under nitrogen atmosphere (S)-1-(2-chloro-acetyl)pyrrolidine-2-carbonitrile (0.17 g, 1.0 mmol) was added. After stirring the reaction mixture at r.t. for 3 h, the reaction mixture was diluted with EtOAc and washed with water and brine, dried over Na$_2$SO$_4$, and the solvent was removed under reduced pressure. The crude product was purified by column chromatography to obtain (2S)-1-[N-(2-fluorohexahydro-2,5-methanopentalen-3a(1H)-yl) glycyl]pyrrolidine-2-carbonitrile as an off-white solid (0.11 g) in 38% yield. m/z (M+1) 292; 1H NMR (CDCl$_3$) 300 MHz δ 4.80-4.73 (m, 1H), 3.77-3.32 (m, 2H), 3.52 (s, 2H), 2.50-2.42 (m, 1H), 2.87-2.08 (m, 6H), 2.0-1.60 (m, 6H), 1.50-1.42 (m, 1H).

Example 23A

Hydrochloride salt: To a stirred solution of the compound obtained from example 23 (29 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with ether to obtain hydrochloride salt of (2S)-1-[N-(2-fluorohexahydro-2,5-methanopentalen-3a(1H)-yl)glycyl]pyrrolidine-2-carbonitrile as an off-white solid (30 mg).

Example 26

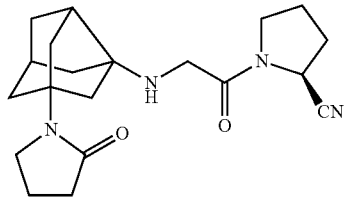

Step I: To a stirred mixture of 1-(3-aminotricyclo[3.3.1.0$^{3,7}$]non-1-yl)pyrrolidin-2-one prepared as in preparation 9 (0.25 g, 1.1 mmol) and K$_2$CO$_3$ (0.46 g, 3.3 mmol) in DMSO (5 mL) at an ice bath temperature was added (S)-1-(2-chloro-acetyl)pyrrolidine-2-carbonitrile (0.2 g, 1.1 mmol). The reaction mixture was gradually warmed to room temperature and stirred for 3 h. Upon completion of the reaction (checked by TLC), the reaction mixture was diluted with EtOAc and washed with water and brine, dried over Na$_2$SO$_4$, and the solvent was removed under reduced pressure. The crude product was purified by column chromatography to obtain (2S)-1-{N-[2-(2-oxopyrrolidin-1-yl)hexahydro-2,5-methanopentalen-3a(1H)-yl]glycyl}pyrrolidine-2-carbonitrile as a viscous liquid (0.16 g) in 40% yield. m/z (M+1) 357; $^1$H NMR (CDCl$_3$) 300 MHz δ 4.78 (d, J=7.4 Hz, 1H), 3.70-3.38 (m, 2H), 3.46 (s, 2H), 3.41 (t, J=7.0 Hz, 2H), 2.60 (dd, J=4.0, 10.2 Hz, 1H), 2.40-1.75 (m, 17H), 1.72-1.62 (m, 1H), 1.58-1.50 (m, 1H).

Example 20A

Hydrochloride salt: To a stirred solution of the compound obtained from example 19 (36 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with ether to obtain the hydrochloride salt of (2S)-1-{N-[2-(2-oxopyrrolidin-1-yl)hexahydro-2,5-methanopentalen-3a (1H)-yl]glycyl}pyrrolidine-2-carbonitrile as off-white solid (38 mg).

Example 27

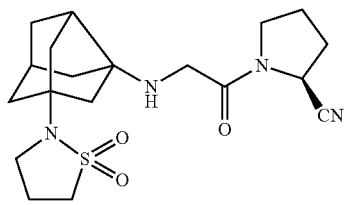

Step I: To a stirred mixture of 1-(1,1-dioxidoisothiazolidin-2-yl)tricyclo[3.3.1.0$^{3,7}$]nonan-3-amine prepared as in preparation 10 (0.17 g, 0.66 mmol), and K$_2$CO$_3$ (0.28 g, 2.0 mmol) in DMSO (2.6 mL) at ice bath temperature was added (S)-1-(2-chloro-acetyl)pyrrolidine-2-carbonitrile (0.13 g, 0.66 mmol). The reaction mixture was gradually warmed to room temperature and stirred for 3 h. Upon completion of the reaction (by TLC), the reaction mixture was diluted with EtOAc and washed with water and brine, dried over $Na_2SO_4$, and the solvent was removed under reduced pressure. The crude product was purified by column chromatography to obtain (2S)-1-{N-[2-(1,1-dioxidoisothiazolidin-2-yl)hexahydro-2,5-methanopentalen-3a(1H)-yl]glycyl}pyrrolidine-2-carbonitrile as a viscous liquid (0.1 g) in 40% yield. m/z (M+1) 393; $^1$H NMR ($CDCl_3$) 300 MHz δ 4.80-4.75 (m, 1H), 3.70-3.37 (m, 4H), 3.36 (t, J=6.6 Hz, 2H), 3.16 (t, J=7.4 Hz, 2H), 2.43-2.37 (m, 1H), 2.35-2.13 (m, 9H), 2.05-1.99 (m, 1H), 1.95-1.75 (m, 5H), 1.70-1.63 (m, 1H), 1.54-1.47 (m, 1H).

Example 21A

Hydrochloride salt: To a stirred solution of the compound obtained in example 20 (39 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain the hydrochloride salt of (2S)-1-{N-[2-(1,1-dioxidoisothiazolidin-2-yl)hexahydro-2,5-methanopentalen-3a(1H)-yl]glycyl}pyrrolidine-2-carbonitrile as an off-white solid (41 mg). m/z (M+1) 393; $^1$H NMR (DMSO-$d_6$) 300 MHz δ 9.60 (s (br), 2H), 4.86 (dd, J=4.4, 7.0 Hz, 1H), 4.12-3.96 (m, 2H), 3.59-3.47 (m, 2H), 3.28 (t, J=6.8 Hz, 2H), 3.19 (t, J=7.5 Hz, 2H), 2.43-2.37 (m, 1H), 2.31-2.13 (m, 8H), 2.10-1.97 (m, 3H), 1.96-1.76 (m, 5H), 1.50-1.43 (m, 1H).

Example 28

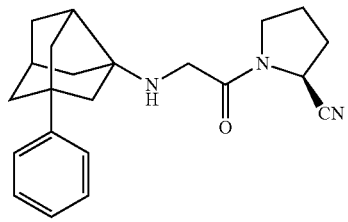

Step I: To a stirred mixture of NaOH (2.4 g, 60.0 mmol), $H_2O$ (16 mL), and 1,4 dioxane (2 mL) at ice bath temperature was added $Br_2$ (0.56 mL, 10.4 mmol) and stirred for 15 minutes. The resulting hypobromite solution was added dropwise to a stirred solution of 1-(1-phenyltricyclo[3.3.1.0$^{3,7}$]non-3-yl)ethanone obtained from preparation I (1.0 g, 4.0 mmol) in 1,4-dioxane (6 mL) at ice bath temperature. After stirring the reaction mixture at r.t. for 1 h, it was again cooled to ice bath temperature and quenched by adding AcOH (3.6 mL, 60 mmol). The reaction mixture was diluted with water and extracted with EtOAc. The combined organic layer was washed with brine, dried over $Na_2SO_4$, and the solvent was removed under reduced pressure to obtain 1-phenyltricyclo[3.3.1.0$^{3,7}$]nonane-3-carboxylic acid (0.62 g) in 64% yield. m/z (M+1) 243; $^1$H NMR ($CDCl_3$) 300 MHz δ 7.40-7.25 (m, 4H), 7.25-7.18 (m, 1H), 2.90-2.86 (m, 1H), 2.54-2.48 (m, 1H), 2.38 (ddd, J=2.0, 2.0, 11.0 Hz, 1H), 2.20-2.05 (m, 4H), 1.98-1.78 (m, 5H), 1.70 (dd, J=2.8, 11.5 Hz, 1H).

Step II: To a stirred solution of 1-phenyltricyclo[3.3.1.0$^{3,7}$]nonane-3-carboxylic acid (0.6 g, 2.48 mmol) obtained from step I and triethylamine (1.0 mL, 7.44 mmol) in toluene (10 mL) under $N_2$ atmosphere at ice bath temperature was added diphenylphosphoryl azide (0.64 mL, 3.0 mmol). The reaction mixture was warmed to room temperature and stirred for 1 h, then it was refluxed for 4 h. The reaction mixture was cooled to r.t., washed with water and stirred with aq. KOH solution (50% w/v, 5.0 mL) and $nBu_4NI$ (92 mg, 0.25 mmol) for 2 h at r.t. The reaction mixture was cooled to ice bath temperature, acidified with conc. HCl to pH 2, extracted with diethyl ether. The aqueous layer was basified with aq. NaOH solution (50% w/v) and extracted with chloroform. The combined organic layer was dried over anhydrous $Na_2SO_4$ and the solvent was evaporated under reduced pressure to obtain 1-phenyltricyclo[3.3.1.0$^{3,7}$]nonan-3-amine (0.33 g) as viscous liquid in 62% yield. m/z (M+1) 214; 1H NMR ($CDCl_3$) 300 MHz δ 7.40-7.22 (m, 4H), 7.22-7.15 (m, 1H), 2.42-2.35 (m, 1H), 2.20-2.05 (m, 2H), 2.02-1.52 (m, 9H).

Step III: To a stirred mixture of the compound obtained from step II (0.2 g, 0.94 mmol) and $K_2CO_3$ (0.39 g, 2.8 mmol) in DMSO (4.0 mL) at ice bath temperature under nitrogen atmosphere (S)-1-(2-chloro-acetyl)pyrrolidine-2-carbonitrile (0.16 g, 0.94 mmol) was added. After stirring the reaction mixture for 3 h at r.t., it was diluted with EtOAc and washed with water and brine, dried over $Na_2SO_4$, and the solvent was removed under reduced pressure. The crude product was purified by column chromatography to obtain (2S)-1-[N-(2-phenylhexahydro-2,5-methanopentalen-3a(1H)-yl)glycyl]pyrrolidine-2-carbonitrile as off-white solid (0.16 g) in 48% yield. m/z (M+1) 350; $^1$H NMR ($CDCl_3$) 300 MHz δ 7.35-7.16 (m, 5H), 4.4.85-4.76 (m, 1H), 3.76-3.40 (m, 2H), 3.50 (s, 2H), 2.48-2.41 (m, 1H), 2.36-2.27 (m, 2H), 2.23-2.0 (m, 6H), 1.94-1.68 (m, 4H), 1.66-1.60 (m, 1H).

Example 26A

Hydrochloride salt: To a stirred solution of the compound obtained from example 26 (35 mg, 0.1 mmol) in methanol (2 mL) cooled to 0° C. was added TMS-Cl (25 μL, 0.2 mmol). After 30 minutes, the volatiles were removed under reduced pressure and the residue was triturated several times with diethyl ether to obtain the hydrochloride salt of (2S)-1-[N-(2-phenylhexahydro-2,5-methanopentalen-3a(1H)-yl)glycyl]pyrrolidine-2-carbonitrile as an off-white solid (38 mg).

Example 29

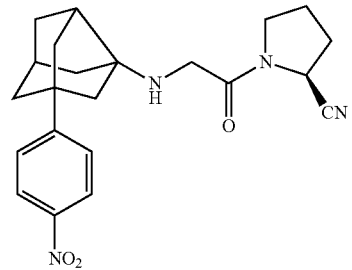

To a stirred mixture of 1-(4-nitrophenyl)tricyclo[3.3.1.0$^{3,7}$]nonan-3-amine as obtained in Step III preparation 4 (0.77 g, 3.0 mmol) and $K_2CO_3$ (1.25 g, 9.0 mmol) in DMSO (12 mL) at ice bath temperature under $N_2$ atmosphere was added (S)-1-(2-chloro-acetyl)pyrrolidine-2-carbonitrile (0.51 g, 3.0 mmol). The reaction mixture was gradually warmed to room temperature and stirred for 3 h. Upon completion of the reaction, the reaction mixture was diluted with EtOAc and washed with water and brine, dried over $Na_2SO_4$ and the solvent was removed under reduced pressure. The crude product was purified by column chromatography to obtain (2S)-1-{N-[2-(4-nitrophenyl) hexahydro-2,5-methanopentalen-3a(1H)-yl]glycyl}pyrrolidine-2-carbonitrile as an off-white solid (0.5 g) in 42% yield. m/z (M+1) 395; $^1$H NMR (CDCl$_3$) 300 MHz δ 8.14 (d, J=8.9 Hz, 2H), 7.41 ((d, J=8.9 Hz, 2H), 4.83-4.73 (m, 1H), 3.78-3.40 (m, 2H), 3.48 (s, 2H), 2.51-2.45 (m, 1H), 2.37-2.06 (m, 6H), 2.02-1.60 (m, 9H).

Example 30

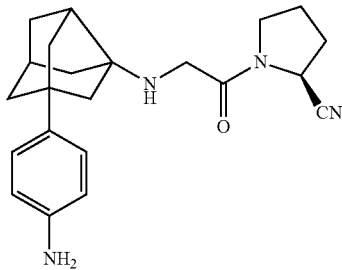

To a stirred solution of the compound obtained from example 29 (0.2 g, 0.51 mmol) in a 1:2:4 mixture of water, THF, and ethanol (7 mL) respectively was sequentially added solid NH$_4$Cl (0.1 g, 1.87 mmol) and Fe powder (0.1 g, 1.78 mmol). The reaction mixture was heated to reflux for 2 h. After cooling the reaction mixture to room temperature, it was filtered through a small pad of celite and washed the bed with EtOAc. The filtrate was evaporated under reduced pressure and the residue was diluted with water and extracted with EtOAc. The combined organic layer was washed with water, dried over anhydrous Na$_2$SO$_4$, and the solvent was evaporated under reduced pressure to obtain (2S)-1-{N-[2-(4-aminophenyl)hexahydro-2,5-methanopentalen-3a(1H)-yl] glycyl}pyrrolidine-2-carbonitrile as off-white solid (0.09 g) in 50% yield. m/z (M+1) 365; $^1$H NMR (CDCl$_3$) 300 MHz δ 7.05 (d, J=8.5 Hz, 2H), 6.63 (d, J=8.5 Hz, 2H), 4.90-4.75 (m, 1H), 3.80-3.40 (m, 4H), 2.45-1.70 (m, 15H), 1.65-1.57 (m, 1H).

Example 31

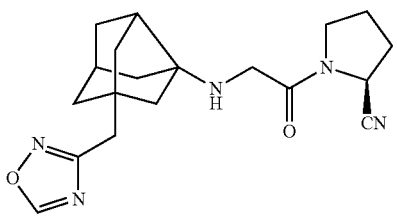

Step I: A stirred mixture of the compound obtained in preparation 3 (1.1 g, 3.18 mmol), sodium cyanide (0.164 g, 3.5 mmol) in DMF (7.0 mL) was heated to 110° C. for 12 h. The reaction mixture was cooled to room temperature, diluted with water, and extracted with EtOAc. The combined organic layer was washed with brine, dried over anhydrous Na$_2$SO$_4$, and the solvent was removed under reduced pressure. The crude product was purified by column chromatography to obtain tert-butyl [1-(cyanomethyl)tricyclo[3.3.1.0$^{3,7}$]non-3-yl]carbamate as viscous liquid (0.3 g) in 34% yield. m/z (M+1), 277; $^1$H NMR (CDCl$_3$) 300 MHz δ 4.73 (bs, 1H), 2.60-2.35 (m, 2H), 2.31 (s, 2H), 2.20-1.40 (s, 10H), 1.45 (s, 9H).

Step II: To a stirred solution of the compound obtained from step I (0.25 g, 0.9 mmol) in a 1:1-mixture of ethanol and water (9 mL) at room temperature was added hydroxylamine hydrochloride (0.32 g, 4.5 mmol) followed by solid Na$_2$CO$_3$ (0.57 g, 5.4 mmol). The reaction mixture was refluxed for 12 h. The volatiles were removed under reduced pressure and the residue was dissolved in ethylacetate and washed with water. The organic layer was dried over anhydrous Na$_2$SO$_4$ and evaporated under reduced pressure. The residue was dissolved in trimethyl orthoformate (0.2 mL) and a catalytic amount of camphor sulfonic acid was added. The reaction mixture was refluxed for 4 h. The volatiles were removed under reduced pressure and the crude product was purified by column chromatography to obtain tert-butyl [1-(1,2,4-oxadiazol-3-ylmethyl)tricyclo[3.3.1.0$^{3,7}$]non-3-yl]carbamate (0.15 g) in 51% yield as viscous liquid. m/z (M+1), 320; $^1$H NMR (CDCl$_3$) 300 MHz δ 8.62 (s, 1H), 4.71 (bs, 1H), 2.79 (s, 2H), 2.48-2.38 (m, 1H), 2.35-2.28 (m, 1H), 2.10-1.88 (m, 4H), 1.74 (dd, J=2.8, 10.5 Hz, 2H), 1.65-1.38 (m, 4H), 1.43 (s, (H).

Step III: To a stirred solution of the compound obtained from step II (0.15 g, 0.47 mmol) in CH$_2$Cl$_2$ (2 mL) cooled to 0° C. was added trifluoroacetic acid (0.5 mL). The reaction mixture was gradually warmed to room temperature and stirred for 1 h. The volatiles were removed under reduced pressure and the residue was triturated several times with ether to obtain 1-(1,2,4-oxadiazol-3-ylmethyl)tricyclo [3.3.1.0$^{3,7}$]nonan-3-amine, trifluoroacetic acid salt as a white powder (0.12 g) in 77% yield. m/z (M+1), 220; $^1$H NMR (DMSO-d$_6$) 300 MHz δ 9.53 (s, 1H), 8.09 (bs, 3H), 2.78 (s, 2H), 2.38-2.25 (m, 2H), 1.88-1.70 (m, 6H), 1.60-1.42 (m, 4H).

Step IV: To a stirred solution of the compound obtained from step III (0.12 g, 0.36 mmol) in DMSO (1.5 mL) at room temperature under nitrogen atmosphere was added, (S)-1-(2-chloro-acetyl)pyrrolidine-2-carbonitrile (0.06 g, 0.0.36 mmol) and K$_2$CO$_3$ (0.2 g, 1.44 mmol). After stirring the reaction mixture for 3 h, it was diluted with EtOAc and washed with water and brine, dried over Na$_2$SO$_4$, and the solvent was removed under reduced pressure. The crude product was purified by column chromatography to obtain ((2S)-1-{N-[2-(1,2,4-oxadiazol-3-ylmethyl)hexahydro-2,5-methanopentalen-3a(1H)-yl]glycyl}pyrrolidin-2-yl)acetonitrile as an off-white solid (0.05 g) in 40% yield. m/z (M+1), 356; 1H NMR (CDCl$_3$) 300 MHz δ 8.64 (s, 1H), 4.84-4.75 (m, 1H), 3.75-3.40 (m, 2H), 3.49 (s, 2H), 2.81 (s, 2H), 2.40-2.10 (m, 6H), 1.92-1.70 (m, 6-H), 1.68-1.48 (m, 4H).

Example 31A

Hydrochloride salt: To a stirred solution of the compound obtained from example 31 (20 mg, 0.056 mmol) in methanol (1 mL) cooled to 0° C. was added TMS-Cl (15 μL, 0.12 mmol). After 30 minutes, the volatiles were removed under reduced pressure and the residue was triturated several times with ether to obtain the hydrochloride salt of the compound as an off-white solid (21 mg).

Example 32

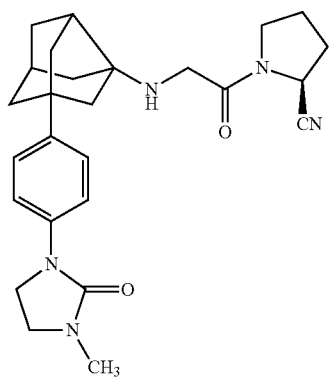

Step I: To a stirred suspension of NaH (50% dispersed in nujol, 50 mg, 1.05 mmol) in THF (3 mL) cooled to 0° C., under $N_2$ atmosphere was added drop-wise with a syringe a solution of the compound obtained in Example 19, step I (0.3 g, 0.7 mmol) in THF (4 mL). After stirring the reaction mixture at room temperature for 30 minutes, it was cooled again to ice-bath temperature and MeI (0.1 mL, 1.5 mmol) was added. The reaction mixture was slowly warmed to room temperature and stirred for 2 h. Excess NaH was quenched by adding aq. $NH_4Cl$ solution after cooling the reaction mixture to ice-bath temperature. The two layers were separated and the aqueous layer was extracted with EtOAc. The combined organic layer was washed with brine, dried over anhydrous $Na_2SO_4$, and the solvent was removed under reduced pressure. The crude product was purified by column chromatography to obtain tert-butyl [2-[4-(3-methyl-2-oxoimidazolidin-1-yl)phenyl]hexahydro-2,5-methanopentalen-3a(1H)-yl]carbamate (250 mg) as an off-white solid in 80% yield. m/z (M+1), 446; $^1$H NMR ($CDCl_3$) 300 MHz δ 7.48 (d, J=8.7 Hz, 2H), 7.43-7.30 (m, 5H), 7.28-7.18 (m, 2H), 5.17-5.03 (m, 3H), 3.80 (t, J=7.2 Hz, 2H), 3.47 (t, J=7.2 Hz, 2H), 2.91 (s, 3H), 2.61-2.52 (m, 1H), 2.48-2.40 (m, 1H), 2.32-1.55 (m, 10H).

Step II: To a stirred solution of the compound obtained from step I (0.25 g, 0.56 mmol) in a 1:1-mixture of $CH_2Cl_2$ and MeOH (10 mL) was added Pd/C (10% w/w, 0.1 g) and stirred at room temperature under $H_2$ atmosphere for 2 h. The reaction mixture was filtered through a pad of celite and the filtrate was concentrated under reduced pressure to obtain 1-[4-(3a-aminohexahydro-2,5-methanopentalen-2(1H)-yl)phenyl]-3-methylimidazolidin-2-one (0.15 g) as an off-white solid in 86% yield. M.R. 227-230° C.; m/z (M+1), 312; IR cm-1 3416, 3249, 2964, 1682, 1519, 1485, 1261, 810; 1H NMR ($CDCl_3$+DMSO-$d_6$) 300 MHz δ 8.38 (bs, 2H), 7.47 (d, J=8.6 Hz, 2H), 7.19 (d, J=8.6 Hz, 2H), 3.76 (t, J=7.4 Hz, 2H), 3.43 (t, J=7.4 Hz, 2H), 2.77 (s, 3H), 2.48-2.40 (m, 2H), 2.22-2.14 (m, 1H), 2.10-2.0 (m, 2H), 2.0-1.86 (m, 4H), 1.80-1.60 (m, 3H).

Step III: To a stirred mixture of the compound obtained from step II (0.15 g, 0.48 mmol) and $K_2CO_3$ (0.21 g, 1.5 mmol) in DMSO (2 mL) at ice bath temperature was added compound (S)-1-(2-chloro-acetyl)pyrrolidine-2-carbonitrile (0.09 g, 0.5 mmol). The reaction mixture was gradually warmed to room temperature and stirred for 3 h. Upon completion of the reaction (checked by TLC), the reaction mixture was diluted with EtOAc and washed with water and brine, dried over $Na_2SO_4$, and the solvent was removed under reduced pressure. The crude product was purified by column chromatography to obtain ((2S)-1-{N-[2-[4-(3-methyl-2-oxoimidazolidin-1-yl)phenyl]hexahydro-2,5-methanopentalen-3a(1H)-yl]glycyl}pyrrolidin-2-yl)acetonitrile as an off-white solid (0.09 g) in 42% yield. m/z (M+1) 449; $^1$H NMR ($CDCl_3$) 300 MHz δ 7.47 (d, J=8.6 Hz, 2H), 7.22 (t, J=8.6 Hz, 2H), 4.85-4.76 (m, 1H), 3.79 (t, J=7.3 Hz, 2H), 3.75-3.40 (m, 4H), 3.48 (s, 2H), 2.89 (s, 3H), 2.46-2.39 (m, 1H), 2.36-2.15 (m, 3H), 2.12-1.58 (m, 12H).

The invention claimed is:

1. A compound of formula I,

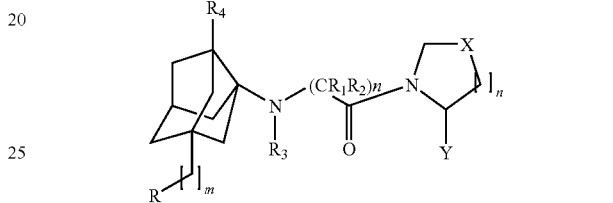

its tautomeric forms, stereoisomers, diastereomers, and pharmaceutically acceptable salts, wherein:

$X=CH_2$, CHF, $CF_2$, CHCl, CHOH, $CHOCH_3$, CHPh;
Y=CN;
$R_1$ and $R_5$ are selected from hydrogen, $C_1$-$C_4$ alkyl, and hydroxy;
$R_2$ is selected from hydrogen, $C_1$-$C_4$ alkyl, substituted alkyl, $C_{1-4}$ alkoxy $C_{1-4}$ alkyl, $C_{1-4}$ hydroxyalkyl, $R_5NHC_{1-4}$ alkyl, and $R_5NHC(NH)NHC_{1-4}$ alkyl;
$R_3$ is selected from hydrogen and $C_1$-$C_4$ alkyl;
$R_4$ is selected from hydrogen, $C_1$-$C_4$ alkyl, substituted alkyl, $C_1$-$C_4$ alkoxy, $C_1$-$C_4$ alkanoyloxy, hydroxy, amino, nitro, $C_2$-$C_6$ alkenyl, acyl, and halogen;
n=1 or 2;
m=0, 1, or 2;
R=$R_{11}$, $R_{12}$, or $R_{13}$, in which $R_{11}$ is at least one group selected from the below a), b), or c), whereupon the at least one group is linked to the nor-adamantyl moiety either directly or via a methylene or ethylene adjacent, either by C—C linkage or by C—N linkage:
a) cycloalkyl group, which is optionally substituted by $C_1$-$C_4$ alkyl, dialkyl, or oxo,
b) optionally substituted heteroaryl group, wherein the substituents of the heteroaryl group are selected from a group consisting of $R_6$ and $R_7$, wherein
$R_6$ is hydrogen, $C_1$-$C_4$ alkyl, $C_2$-$C_4$ alkenyl, hydroxy, hydroxy alkyl, alkylamino, haloalkyl, amino, acyl, $COOR_9$, or $COR_9$, and $R_7$ is selected from a group consisting of hydrogen, hydroxy, halogen, amino, nitro, $C_1$-$C_8$ alkyl, $C_2$-$C_4$ alkenyl, $COOR_9$, $CONR_8R_9$, $COR_9$, $NHCOOR_8$, $NHS(O)_2R_8$, $NHS(O)R_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $OSO_2R_8$, $OCONR_8R_9$, $SO_2R_8$, $SOR_8$, $SR_8$, $SO_2NR_8R_9$, $S(O)_2OR_8$, and when $R_6$ and $R_7$ are present on adjacent carbons of the ring system, they may together form a six membered aromatic ring or a heterocyclic ring with further substitutions;

c) heterocyclyl group optionally substituted by $C_1$-$C_3$ alkyl, dialkyl and oxo groups,
wherein the heterocyclic ring system is a 4- to 10-membered mono- or bicyclic ring system with one or more heteroatoms selected from the group consisting of nitrogen, sulfur, and oxygen and functional groups thereof wherein the heterocyclic ring system contains no, one, or two double bonds, $R_{12}$ is selected from hydrogen, halogen, haloalkyl, hydroxy, carboxy, nitro, amino, cyano, alkyl sulfinyl, alkylsulfonyl, alkylthio, amidinyl, alkoxy, alkoxy carbonylamino, ureido, thiureido, alkanoyl, alkanoyloxy, alkanoyl amino, carbamoyl, guanidyl, optionally substituted $C_1$-$C_8$ alkyl, and $C_2$-$C_6$ alkenyl;

$R_{13}$ is optionally substituted aryl, wherein at least one of the substituents thereof comprises at least one group selected from
a) hydrogen;
b) $C_1$-$C_8$ alkyl, $C_2$-$C_6$ alkenyl, halo, alkylhalo, alkoxy, alkylsulfonyl, alkylsulfinyl, alkoxy, alkanoyl, alkanoyloxy, acylamino, carbonylamino, guanidyl, nitro, amino, $COOR_9$, $R_8NHC(O)R_9$, $COR_9$, $CONR_8R_9$, $NHC(O)OR_8$, $NHC(O)R_8$, $NHC(O)NR_8R_9$, $NHC(O)NR_8R_9$, $NHS(O)_2R_8$, $NHS(O)R_8$, $NHS(O)_2NHR_8$, $NHS(O)_2NHC(O)R_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $S(O)_2R_8$, $SOR_8$, $SR_8$, $S(O)_2NR_8R_9$, $OCF_3$, $OS(O)_2R_8$, or $OC(O)NR_8R_9$;
c) saturated, partially saturated, or unsaturated, mono- or bicyclic heterocyclic ring system optionally substituted by one or more groups selected from $C_1$-$C_3$ alkyl, $C_2$-$C_6$ alkenyl, dialkyl, and oxo, wherein the heterocyclic ring system is a 4- to 10-membered ring with one or more heteroatoms selected from the group consisting of nitrogen, sulfur, and oxygen and functional groups thereof;
wherein $R_8$, $R_9$, and $R_{10}$, which are optionally substituted by halogen, hydroxy, alkoxy, cyano, nitro, alkyl, acyl, acyloxy, hydroxyalkyl, amino, alkylthio, or thioalkyl groups, are individually selected from hydrogen, optionally substituted $C_1$-$C_8$ alkyl, aryl, arylalkyl, alkoxy carbonyl, and arylalkoxy carbonyl and when $R_8$ and $R_9$ are present together on a nitrogen atom they form a 5- or 6-membered saturated, partially unsaturated, or unsaturated cyclic system containing carbon atoms, at least one nitrogen atom and optionally one or more other heteroatoms selected from oxygen, sulfur, and nitrogen.

2. A compound of formula I according to claim 1, wherein $R=R_{11}$ and $R_{11}$ is at least one $C_4$-$C_7$ cycloalkyl group, which is optionally substituted by $C_1$-$C_4$ alkyl, dialkyl, or oxo.

3. A compound of formula I according to claim 1, wherein $R=R_{11}$ and $R_{11}$ is at least one $C_5$-$C_6$ cycloalkyl group, which is optionally substituted by $C_1$-$C_4$ alkyl, dialkyl, or oxo.

4. A compound of formula I according to claim 1, wherein $R=R_{11}$ and $R_{11}$ is at least one 4 to 6-membered, mono-heterocyclic ring system with one or more heteroatoms selected from the group consisting of nitrogen, sulfur, and oxygen and functional groups thereof, wherein the heterocyclic ring system is optionally substituted by $C_1$-$C_3$ alkyl, dialkyl and oxo groups and contains no, one, or two double bonds.

5. A compound of formula I according to claim 1, wherein $R=R_{11}$ and $R_{11}$ is at least one optionally substituted 5 to 10 membered heteroaryl ring system, in which the heteroaryl ring system is a monocyclic aromatic ring system or a bicyclic aromatic ring system comprising one, two, or more heteroatoms selected from nitrogen, sulfur, and oxygen, and wherein the substituents of the heteroaryl ring system are selected from a group consisting of $R_6$ and $R_7$, wherein $R_6$ is hydrogen, $C_1$-$C_4$ alkyl, $C_2$-$C_4$ alkenyl, hydroxy, hydroxy alkyl, alkylamino, haloalkyl, amino, acyl, $COOR_9$, or $COR_9$, and $R_7$ is selected from a group consisting of hydrogen, hydroxy, halogen, amino, nitro, $C_1$-$C_8$ alkyl, $C_2$-$C_4$ alkenyl, $COOR_9$, $CONR_8R_9$, $COR_9$, $NHCOOR_8$, $NHS(O)_2R_8$, $NHS(O)R_8$, $NHS(O)_2NHR_8$, $NR_8COOR_9$, $NR_8COR_9$, $NR_8S(O)_2R_9$, $NR_8CONR_8R_9$, $NR_8C(S)NR_8R_9$, $NHC(O)NHS(O)_2R_8$, $OSO_2R_8$, $OCONR_8R_9$, $SO_2R_8$, $SOR_8$, $SR_8$, $SO_2NR_8R_9$, $S(O)_2OR_8$, and when $R_6$ and $R_7$ are present on adjacent carbons of the ring system, they may together form a six membered aromatic ring or a heterocyclic ring with further substitutions.

6. A compound of formula Ia as claimed in claim 1

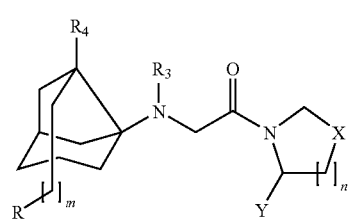

its tautomeric forms, stereoisomers, diastereomers, and pharmaceutically acceptable salts, wherein $X=CH_2$, CHF;
$Y=CN$;
$R_3$ is independently selected from hydrogen and $C_1$-$C_4$ alkyl;
$R_4$ is selected from hydrogen, $C_1$-$C_4$ alkyl, substituted alkyl, $C_1$-$C_4$ alkoxy, $C_1$-$C_4$ alkanoyloxy, hydroxy, amino, nitro, $C_2$-$C_6$ alkenyl, acyl, and halogen;
n=1 or 2;
m=0, 1, or 2;
R is $R_{11}$, $R_{12}$, or $R_{13}$; and
wherein $R_{11}$, $R_{12}$, and $R_{13}$ are as defined in claim 1.

7. A compound according to claim 1, wherein
R is $R_{11}$;
m is 1;
$R_3$ is hydrogen;
$R_4$ is hydrogen;
n is 1;
Y is CN;
X is $CH_2$, CHF; and
$R_{11}$ is as defined in claim 1.

8. A compound according to claim 1, wherein
R is $R_{11}$ or $R_{12}$;
m is 0;
$R_1$, $R_2$, $R_3$, and $R_4$ are hydrogen;
n is 1;
Y is CN;
X is $CH_2$, CHF; and
$R_{11}$ and $R_{12}$ are as defined in claim 1.

9. A compound according to claim 1, wherein
R is $R_{13}$;
m is 0;

R₁, R₂, R₃, and R₄ are hydrogen;
n is 1;
Y is CN;
X is CH₂, CHF; and
R₁₃ is as defined in claim 1.

10. A compound according to claim 1, wherein the compound is selected from
- (2S)-1-[1H-1,2,4-triazol-1-ylmethyl-(tricyclo[3.3.1.0$^{3,7}$]non-3-ylamino)acetyl]pyrrolidine-2-carbonitrile or its salts in its single enantiomeric form or as a racemate;
- (2S,4S)-4-fluoro-1-{N-[2-(1H-1,2,4-triazol-1-ylmethyl)hexahydro-2,5-methanopentalen-3a(1H)-yl]glycyl}pyrrolidine-2-carbonitrile or its salts in its single enantiomeric form or as a racemate;
- (2S,4R)-4-fluoro-1-{N-[2-(1H-1,2,4-triazol-1-ylmethyl)hexahydro-2,5-methanopentalen-3a(1H)-yl]glycyl}pyrrolidine-2-carbonitrile or its salts in its single enantiomeric form or as a racemate;
- (2S)-1-{N-[2-(1H-tetrazol-1-ylmethyl)hexahydro-2,5-methanopentalen-3a(1H)-yl]glycyl}pyrrolidine-2-carbonitrile or its salts in its single enantiomeric form or as a racemate;
- (2S)-1-{N-[2-[(4-methylpiperazin-1-yl)methyl]hexahydro-2,5-methanopentalen-3a(1H)-yl]glycyl}pyrrolidine-2-carbonitrile or its salts in its single enantiomeric form or as a racemate;
- (2S)-1-{N-[2-(thiomorpholin-4-ylmethyl)hexahydro-2,5-methanopentalen-3a(1H)-yl]glycyl}pyrrolidine-2-carbonitrile or its salts in its single enantiomeric form or as a racemate;
- (2S)-1-{N-[2-[(1,1-dioxidoisothiazolidin-2-yl)methyl]hexahydro-2,5-methanopentalen-3a(1H)-yl]glycyl}pyrrolidine-2-carbonitrile or its salts in its single enantiomeric form or as a racemate;
- (2S)-1-{N-[2-[(2,4-dioxo-1,3-thiazolidin-3-yl)methyl]hexahydro-2,5-methanopentalen-3a(1H)-yl]glycyl}pyrrolidine-2-carbonitrile or its salts in its single enantiomeric form or as a racemate;
- (2S)-1-{N-[2-[(1,3-dioxo-1,3-dihydro-2H-isoindol-2-yl)methyl]hexahydro-2,5-methanopentalen-3a(1H)-yl]glycyl}pyrrolidine-2-carbonitrile or its salts in its single enantiomeric form or as a racemate;
- ((2S)-1-{N-[2-(1,2,4-oxadiazol-3-ylmethyl)hexahydro-2,5-methanopentalen-3a(1H)-yl]glycyl}pyrrolidin-2-yl)acetonitrile or its salts in its single enantiomeric form or as a racemate;
- (2S)-1-{N-[2-[4-(1,1-dioxidoisothiazolidin-2-yl)phenyl]hexahydro-2,5-methanopentalen-3a(1H)-yl]glycyl}pyrrolidine-2-carbonitrile or its salts in its single enantiomeric form or as a racemate;
- (2S,4S)-1-{N-[2-[4-(1,1-dioxidoisothiazolidin-2-yl)phenyl]hexahydro-2,5-methanopentalen-3a(1H)-yl]glycyl}-4-fluoropyrrolidine-2-carbonitrile or its salts in its single enantiomeric form or as a racemate;
- (2S,4R)-1-{N-[2-[4-(1,1-dioxidoisothiazolidin-2-yl)phenyl]hexahydro-2,5-methanopentalen-3a(1H)-yl]glycyl}-4-fluoropyrrolidine-2-carbonitrile or its salts in its single enantiomeric form or as a racemate;
- (2S)-1-{N-[2-[4-(2-oxopyrrolidin-1-yl)phenyl]hexahydro-2,5-methanopentalen-3a(1H)-yl]glycyl}pyrrolidine-2-carbonitrile or its salts in its single enantiomeric form or as a racemate;
- (2S,4S)-4-fluoro-1-{N-[2-[4-(2-oxopyrrolidin-1-1)phenyl]hexahydro-2,5-methanopentalen-3a(1H)-yl]glycyl}pyrrolidine-2-carbonitrile or its salts in its single enantiomeric form or as a racemate;
- (2S)-1-{N-[2-[4-(1H-pyrrol-1-yl)phenyl]hexahydro-2,5-methanopentalen-3a(1H)-yl]glycyl}pyrrolidine-2-carbonitrile or its salts in its single enantiomeric form or as a racemate;
- (2S)-1-{N-[2-[4-(2-oxoimidazolidin-1-yl)phenyl]hexahydro-2,5-methanopentalen-3a(1H)-yl]glycyl}pyrrolidine-2-carbonitrile or its salts in its single enantiomeric form or as a racemate;
- ((2S)-1-{N-[2-[4-(3-methyl-2-oxoimidazolidin-1-yl)phenyl]hexahydro-2,5-methanopentalen-3a(1H)-yl]glycyl}pyrrolidin-2-yl)acetonitrile or its salts in its single enantiomeric form or as a racemate;
- (2S)-1-[(tricyclo[3.3.1.0$^{3,7}$]non-3-ylamino)acetyl]pyrrolidine-2-carbonitrile or its salts in its single enantiomeric form or as a racemate;
- (2S)-1-{[(1-hydroxytricyclo[3.3.1.0$^{3,7}$]non-3-yl)amino]acetyl}pyrrolidine-2-carbonitrile or its salts in its single enantiomeric form or as a racemate;
- (2S)-1-{[(1-methoxytricyclo[3.3.1.0$^{3,7}$]non-3-yl)amino]acetyl}pyrrolidine-2-carbonitrile or its salts in its single enantiomeric form or as a racemate;
- (2S)-1-{[(1-ethoxytricyclo[3.3.1.0$^{3,7}$]non-3-yl)amino]acetyl}pyrrolidine-2-carbonitrile or its salts in its single enantiomeric form or as a racemate;
- (2S)-1-{[(1-aminotricyclo[3.3.1.0$^{3,7}$]non-3-yl)amino]acetyl}pyrrolidine-2-carbonitrile or its salts in its single enantiomeric form or as a racemate;
- (2S)-1-[N-(2-fluorohexahydro-2,5-methanopentalen-3a(1H)-yl)glycyl]pyrrolidine-2-carbonitrile or its salts in its single enantiomeric form or as a racemate;
- (2S)-1-{N-[2-(2-oxopyrrolidin-1-yl)hexahydro-2,5-methanopentalen-3a(1H)-yl]glycyl}pyrrolidine-2-carbonitrile or its salts in its single enantiomeric form or as a racemate;
- (2S)-1-{N-[2-(1,1-dioxidoisothiazolidin-2-yl)hexahydro-2,5-methanopentalen-3a(1H)-yl]glycyl}pyrrolidine-2-carbonitrile or its salts in its single enantiomeric form or as a racemate;
- (2S)-1-[N-(2-phenylhexahydro-2,5-methanopentalen-3a(1H)-yl)glycyl]pyrrolidine-2-carbonitrile or its salts in its single enantiomeric form or as a racemate;
- (2S)-1-{N-[2-(4-nitrophenyl)hexahydro-2,5-methanopentalen-3a(1H)-yl]glycyl}pyrrolidine-2-carbonitrile or its salts in its single enantiomeric form or as a racemate; and
- (2S)-1-{N-[2-(4-aminophenyl)hexahydro-2,5-methanopentalen-3a(1H)-yl]glycyl}pyrrolidine-2-carbonitrile or its salts in its single enantiomeric form or as a racemate.

11. A process for the preparation of a compound of claim 1, which process comprises the steps of:
coupling a compound of formula II, which is in its free form, in a form of a salt, or in a protected form, with a compound of formula III

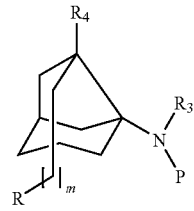

II

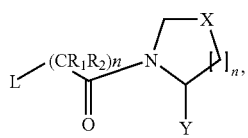

wherein P is hydrogen or a protecting group, L is a leaving group, and R, $R_1$, $R_2$, $R_3$, $R_4$, X, Y, n, and m are as defined in claim 1.

12. A pharmaceutical composition comprising a compound of claim 1 and at least one pharmaceutically acceptable carrier, diluent, or excipient.

13. A method for the treatment of diseases which are associated with DPP-IV, selected from the group consisting of type II diabetes, diabetic complications as well as for the treatment of dislipidemia, hypercholesterolemia, obesity and hyperglycemia which method comprises administering to a host suffering therefrom a therapeutically effective amount of a compound according to claim 1.

14. A compound of formula I according to claim 1 wherein, when $R_6$ and $R_7$ are present on adjacent carbons of the ring system, they together form a phenyl ring.

15. A compound of formula I according to claim 1 wherein, when $R_6$ and $R_7$ are present on adjacent carbons of the ring system they form a pyridine heterocyclic ring.

* * * * *